(12) United States Patent
Das et al.

(10) Patent No.: US 12,241,104 B2
(45) Date of Patent: Mar. 4, 2025

(54) USE OF METAL SALTS AND DEEP EUTECTIC SOLVENTS IN A PROCESS TO SOLUBILIZE A BIOMASS

(71) Applicants: THE REGENTS OF THE UNIVERSITY OF CALIFORNIA, Oakland, CA (US); NATIONAL TECHNOLOGY AND ENGINEERING SOLUTIONS OF SANDIA, LLC, Albuquerque, NM (US)

(72) Inventors: Lalitendu Das, Emeryville, CA (US); Hemant Choudhary, Emeryville, CA (US); John M. Gladden, Alameda, CA (US); Blake A. Simmons, San Francisco, CA (US)

(73) Assignees: THE REGENTS OF THE UNIVERSITY OF CALIFORNIA, Oakland, CA (US); NATIONAL TECHNOLOGY & ENGINEERING SOLUTIONS OF SANDIA, LLC, Albuquerque, NM (US)

( * ) Notice: Subject to any disclaimer, the term of this patent is extended or adjusted under 35 U.S.C. 154(b) by 0 days.

(21) Appl. No.: 17/220,846

(22) Filed: Apr. 1, 2021

(65) Prior Publication Data

US 2021/0317481 A1 Oct. 14, 2021

Related U.S. Application Data

(60) Provisional application No. 63/003,791, filed on Apr. 1, 2020.

(51) Int. Cl.
*C12P 19/14* (2006.01)
*C12P 7/10* (2006.01)
*C12P 19/02* (2006.01)

(52) U.S. Cl.
CPC ............... *C12P 19/14* (2013.01); *C12P 7/10* (2013.01); *C12P 19/02* (2013.01); *C12P 2201/00* (2013.01)

(58) Field of Classification Search
CPC ............ C12P 7/10; C12P 19/02; C12P 19/14; C12P 2201/00; C12P 7/06; C12P 7/649; Y02E 50/10; Y02P 20/54
See application file for complete search history.

(56) References Cited

U.S. PATENT DOCUMENTS

| | | | |
|---|---|---|---|
| 6,177,575 B1 | 1/2001 | Arduengo, III et al. | |
| 7,985,567 B2 | 7/2011 | Chou et al. | |
| 8,420,833 B2 | 4/2013 | Katz et al. | |
| 8,852,902 B2 | 10/2014 | Katz et al. | |
| 9,109,175 B2 | 8/2015 | Lee et al. | |
| 9,200,298 B2 | 12/2015 | Lee et al. | |
| 9,322,042 B2 | 4/2016 | Sapra et al. | |
| 9,334,514 B2 | 5/2016 | Fortman et al. | |
| 9,376,691 B2 | 6/2016 | Peralta-Yahy et al. | |
| 9,376,728 B2 | 6/2016 | Zhang et al. | |
| 9,382,553 B2 | 7/2016 | Kirby et al. | |
| 9,624,482 B2 | 4/2017 | Sapra et al. | |
| 9,631,210 B2 | 4/2017 | Chou et al. | |
| 9,725,749 B2 | 8/2017 | Chen et al. | |
| 9,765,044 B2 | 9/2017 | Socha et al. | |
| 9,803,182 B2 | 10/2017 | Gladden et al. | |
| 9,862,982 B2 | 1/2018 | Zhang et al. | |
| 9,951,345 B2 | 4/2018 | Steen et al. | |
| 10,155,735 B2 | 12/2018 | Socha et al. | |
| 10,167,488 B2 | 1/2019 | Keasling et al. | |
| 10,723,859 B2 * | 7/2020 | Shi ........................ | C08J 11/16 |
| 2004/0097755 A1 | 5/2004 | Abbott et al. | |
| 2010/0196967 A1 | 8/2010 | Edye et al. | |
| 2021/0155995 A1 * | 5/2021 | Bartek ................... | C13K 13/00 |

FOREIGN PATENT DOCUMENTS

| | | |
|---|---|---|
| WO | 2009/006386 A2 | 1/2009 |
| WO | 2009/006429 A1 | 1/2009 |
| WO | 2009/006430 A1 | 1/2009 |
| WO | 2009/134899 A2 | 11/2009 |
| WO | 2010/124266 A1 | 10/2010 |
| WO | 2010/127318 A2 | 11/2010 |
| WO | 2012/050931 A2 | 4/2012 |
| WO | 2012/058686 A2 | 5/2012 |
| WO | 2012/064740 A1 | 5/2012 |
| WO | 2012/071439 A1 | 5/2012 |
| WO | 2012/135389 A2 | 10/2012 |

(Continued)

OTHER PUBLICATIONS

AlOmar et al., Glycerol-based deep eutectic solvents: Physical properties. J. Mol. Liquids., 2016, vol. 215: 98-10. (Year: 2016).*
Chen et al., Surface Tension of 50 Deep Eutectic Solvents: Effect of Hydrogen-Bonding Donors, Hydrogen-Bonding Acceptors, Other Solvents, and Temperature. Ind. Eng. Chem. Res., 2019, vol. 58: 12741-12750 (Year: 2016).*
Marcus Y., Unconventional Deep Eutectic Solvents: Aqueous Salt Hydrates. ACS Sust. Chem. Eng., 2017, vol. 5: 11780-11787. (Year: 2017).*
Mota-Morales et al., Free-radical polymerizations of and in deep eutectic solvents: Green synthesis of functional materials. Prog. Polymer Sci., 2018, vol. 78: 139-153. (Year: 2018).*
Dai et al., Enhancing the enzymatic saccharification of bamboo shoot shell by sequential biological pretreatment with *Galactomyces* sp.CCZU11-1 and deep eutectic solvent extraction. Bioprocess Biosyst Eng., 2017, vol. 40: 1427-1436. (Year: 2017).*

(Continued)

*Primary Examiner* — Ganapathirama Raghu
(74) *Attorney, Agent, or Firm* — Robin C. Chiang; LAWRENCE BERKELEY NATIONAL LABORATORY

(57) ABSTRACT

The present invention also provides for a method to deconstruct a biomass: the method comprising: (a) introducing a solvent to a biomass to dissolve at least part of solid biomass in the solvent, wherein the solvent comprises (i) a metal salt, and (ii) an ionic liquid (IL) or deep eutectic solvent (DES), or mixture thereof, to form a solubilized biomass mixture; (b) optionally introducing an enzyme and/or a microbe to the composition such that the enzyme and/or microbe produce a biofuel and/or chemical compound from the solubilized biomass; and, (c) optionally the biofuel and/or chemical compound is separated from the composition.

16 Claims, 38 Drawing Sheets

(56) References Cited

FOREIGN PATENT DOCUMENTS

| WO | 2012/151214 A1 | 11/2012 |
|---|---|---|
| WO | 2014/093402 A2 | 6/2014 |
| WO | 2015/013674 A1 | 1/2015 |
| WO | 2016070125 A1 | 5/2016 |
| WO | 2016/105538 A1 | 6/2016 |
| WO | 2017/087982 A2 | 5/2017 |
| WO | 2017091781 A1 | 6/2017 |
| WO | 2017/214159 A1 | 12/2017 |
| WO | 2017/214332 A1 | 12/2017 |
| WO | 2018119152 A1 | 6/2018 |
| WO | 2018/200888 A1 | 11/2018 |
| WO | 2018/204424 A1 | 11/2018 |
| WO | 2019/050990 A1 | 3/2019 |

OTHER PUBLICATIONS

Chen et al., High-Solid Lignocellulose Processing Enabled by Natural Deep Eutectic Solvent for Lignin Extraction and Industrially Relevant Production of Renewable Chemicals. ACS Sust. Chem. Eng., 2018, vol. 6: 12205-12216. (Year: 2018).*

Chen et al., Ternary deep eutectic solvents for effective biomass deconstruction at high solids and low enzyme loadings. Bioresource Technol., 2019, vol. 279: 281-286. (Year: 2019).*

Greaves et al. "Protic Ionic Liquids: Properties and Applications" Chem. Rev. 108(1):206-237 (2008).

Chen et al. "Distillable Ionic Liquids: reversible Amide O Alkylation", Angewandte Comm. 52:13392-13396 (2013).

King et al. "Distillable Acid-Base Conjugate Ionic Liquids for Cellulose Dissolution and Processing", Angewandte Comm. 50:6301-6305 (2011).

Vijayaraghavan et al. "CO2-based Alkyl Carbamate Ionic Liquids as Distillable Extraction Solvents", ACS Sustainable Chem. Engin. 2:31724-1728 (2014).

Idris et al. "Distillable Protic Ionic Liquids for Keratin Dissolution and Recovery", ACS Sustainable Chem. Engin. 2:1888-1894 (2014).

Sun et al. "One-pot integrated biofuel production using low-cost biocompatible protic ionic liquids", Green Chem. 19 (13):3152-3163 (2017).

* cited by examiner

USE OF METAL SALTS AND DEEP EUTECTIC SOLVENTS IN A PROCESS TO SOLUBILIZE A BIOMASS

CROSS-REFERENCE TO RELATED APPLICATIONS

This application claims priority to U.S. Provisional Patent Application Ser. No. 63/003,791, filed on Apr. 1, 2020, which is hereby incorporated by reference.

STATEMENT OF GOVERNMENTAL SUPPORT

The invention was made with government support under Contract Nos. DE-AC02-05CH11231 awarded by the U.S. Department of Energy. The government has certain rights in the invention.

FIELD OF THE INVENTION

The present invention is in the field of using deep eutectic solvents for biomass pretreatment.

BACKGROUND OF THE INVENTION

Lignocellulosic biomass typically constitutes of lignin, cellulose and hemicellulose, which accounts for 85% mass of the plant biomass. Lignin is a highly complex aromatic heteropolymer whose biological role in plants is to increase cell wall integrity and resistance to attack by pathogens. Lignin comprises of 15-30% of biomass is one of the major components apart from cellulose and hemicelluloses in the lignocellulosic complex. The heterogeneity of lignin, however, is the primary hurdle to its targeted upgrading and reuse as a feedstock for chemicals and advanced materials. Hence the lignin from biorefineries and pulp and paper manufacturers are combusted as a low value fuel to generate heat and power. Thus, simultaneous conversion of carbohydrates and lignin into high-value products augment the economic viability of biorefiners and pulp or paper manufacturers. Several thermochemical lignin depolymerization methods are being explored; among these are high temperature pyrolysis, hydrogenolysis and catalytic oxidation, etc. Enormous efforts have been focused on improving the catalyst efficiency and selectivity in a thermochemical conversion process. However, the effectiveness and selectivity of the catalyst as developed on lignin model compounds often get compromised when applied to plant derived lignin due to the intrinsic structural and compositional complexity of lignin. An emerging technology that has the potential to contribute to biomass fractionation and lignin depolymerization is the use of deep eutectic solvents. DES is a mixture of two or more hydrogen-bond donors (HBD) and hydrogen-bond acceptors (HBA), certain DESs facilitates the controlled cleavage of aryl ether linkages in the phenylpropane units, leading to the delignification of biomass. Hence, imbedding a metal catalyst in DESs could offer a new strategy for selective lignin depolymerization meanwhile helps to tackle the challenges associated with DES recycle and product recovery.

SUMMARY OF THE INVENTION

The present invention provides for a method to produce a biofuel and/or chemical compound from a biomass, the method comprising: (a) introducing a biomass and a metal-based deep eutectic solvent (mDES), or mixture thereof, into a vessel to form a composition, wherein the mDES, or mixture thereof, solubilizes the biomass; (b) optionally introducing an enzyme and/or a microbe to the composition such that the enzyme and/or microbe produce a biofuel and/or chemical compound from the solubilized biomass; and, (c) optionally the biofuel and/or chemical compound is separated from the composition. In some embodiments, the introducing step (a) and the optional steps (b) and (c) are continuous. In some embodiments, the mDES comprises a metal salt and a deep eutectic solvent (DES). In some embodiments, the mDES comprises The present invention also provides for compositions described herein.

The present invention also provides for a mixture of mDESs produced by the method described herein.

The present invention provides for a method for producing renewable fuel or chemical using a process approach from cellulosic biomass.

The present invention also provides for a mDES mixture comprising zinc chloride and glycerol with a molar ratio of about 1:4, a mDES mixture that comprises zinc chloride and ethylene glycol with a molar ratio of about 1:4, or a mixture thereof.

The present invention also provides for a method to deconstruct a biomass: the method comprising: (a) introducing a solvent to a biomass to dissolve at least part of solid biomass in the solvent, wherein the solvent comprises (i) a metal salt, and (ii) an ionic liquid (IL) or deep eutectic solvent (DES), or mixture thereof, to form a solubilized biomass mixture.

In some embodiments, the metal salt is a mixture of metal salts. In some embodiments, the metal salt is a metal phosphate. In some embodiments, the metal is an aluminum, niobium, or zirconium. In some embodiments, the metal phosphate is an aluminum phosphate, niobium phosphate, zirconium phosphate, or a mixture thereof. In some embodiments, the IL is mixture of ILs. In some embodiments, the DES is mixture of DESs.

In some embodiments, the method further comprises (b) introducing an enzyme and/or a microbe to the solubilized biomass mixture such that the enzyme and/or microbe produces a sugar from the solubilized biomass mixture. In some embodiments, the solvent has limited or no inhibition of the enzyme and/or limited or no toxicity to the microbe.

In some embodiments, the method further comprises (c) separating the sugar from the solubilized biomass mixture. In some embodiments, the introducing step (a), the introducing step (b), and/or the separating step (c) do not comprise or lack introducing or adding any water to the biomass or biomass mixture.

In some embodiments, the method further comprises separating the solubilized biomass mixture into an aqueous layer or portion (comprising most or all of the sugars or saccharides produced from the introducing step (b)) and a DES layer or portion (comprising most or all of the lignin and or biomass). In some embodiments, the aqueous layer or portion is placed in a fermentation chamber. In some embodiments, the DES layer or portion is placed in a lignin fermentation chamber.

In some embodiments, the method further comprises washing the solubilized biomass mixture with ethanol, water, or a mixture thereof, to produce a post-wash solution. In some embodiments, the post-wash solution comprises one or more, or all, of the compounds depicted in FIG. 18.

In some embodiments, the result of saccharification comprises a yield of glucose and/or xylose, or both, having a yield of any value depicted in FIGS. 21-25, or within a range of two values depicted thereof.

In some embodiments, the percent solid recovery is of any percent depicted in Table 4, or within a range of two values depicted thereof.

In some embodiments, the microbe is *Rhodosporidium toruloides* or *Pseudomonas putida*.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
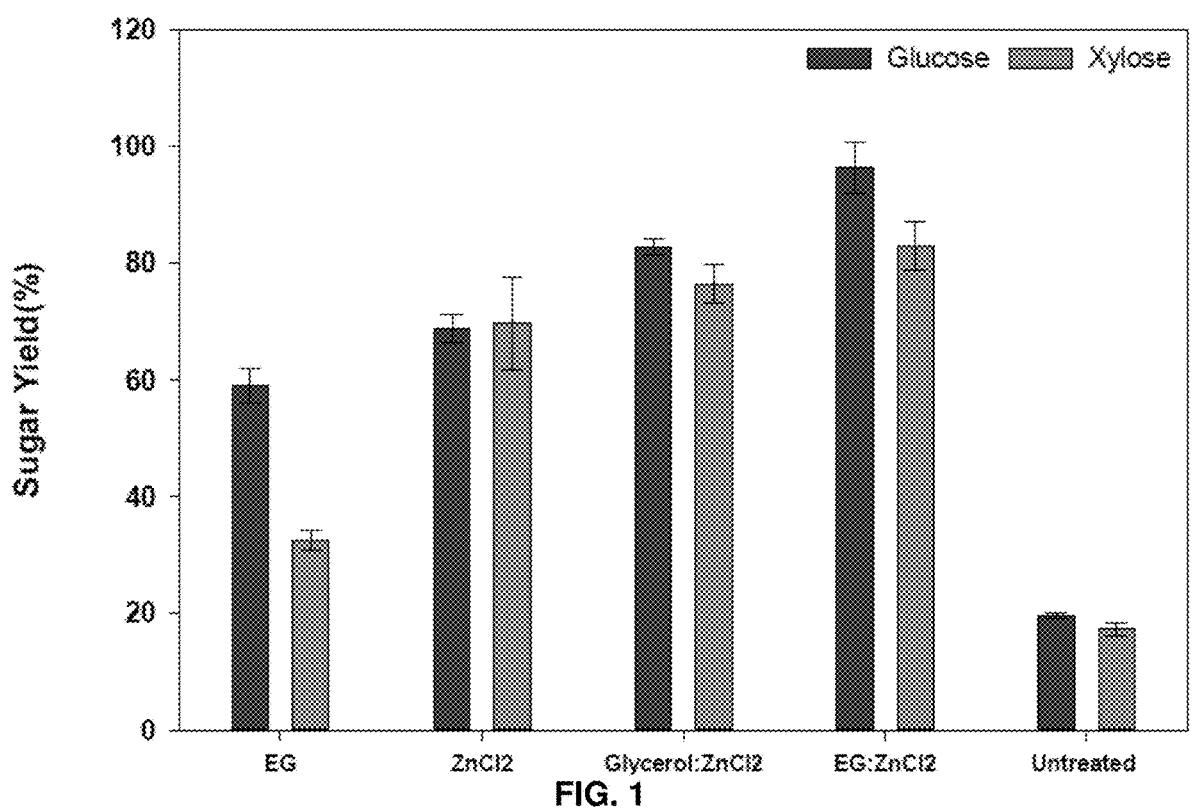
FIG. 1: Glucose and xylose yield from mDES, individual mDES components, and untreated biomass at temperature of 140° C., 3 h reaction time, and 10% solid loading.
Figure 2A:
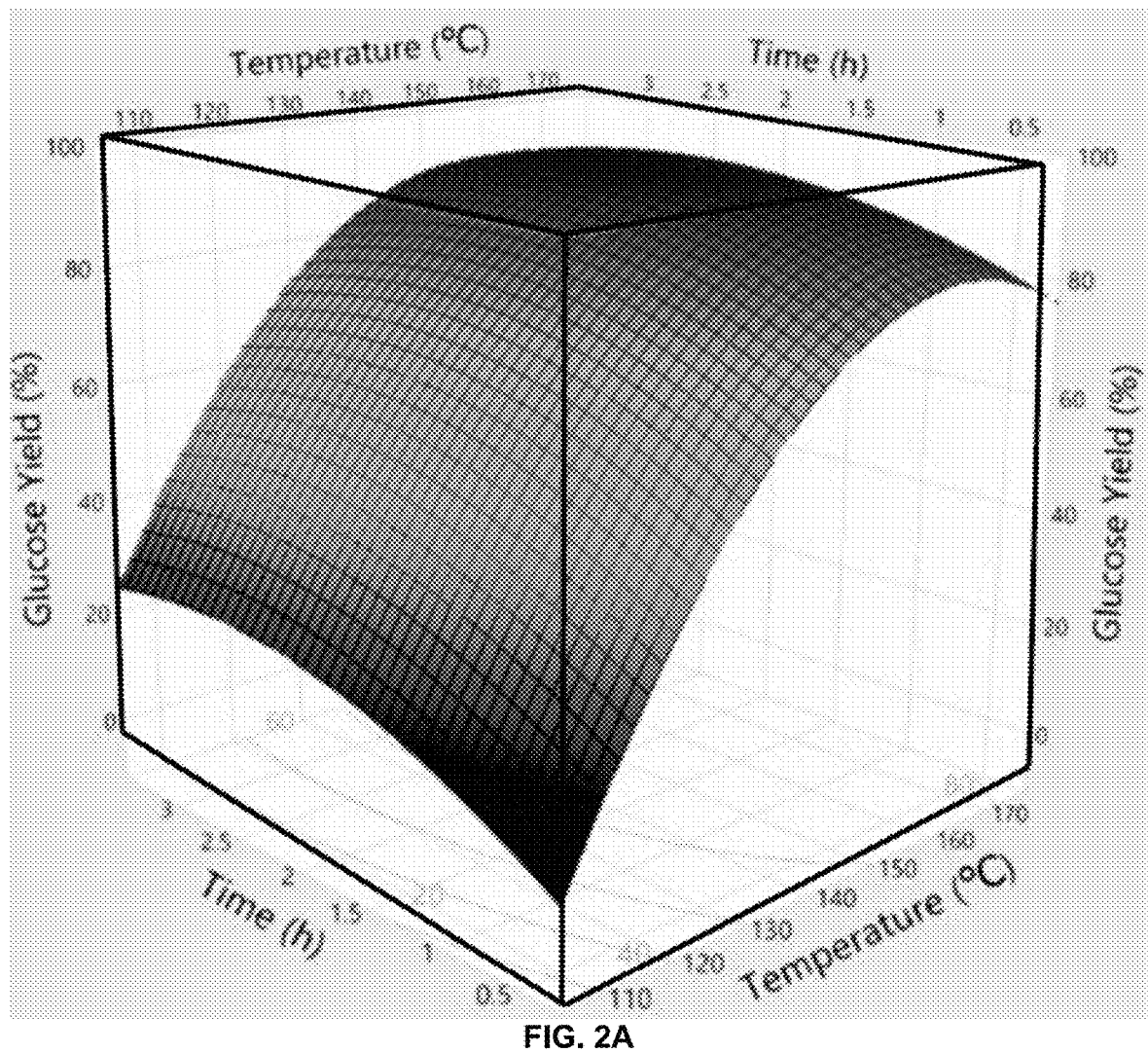
FIG. 2A. Surface response plots showing the effect of reaction time and temperature on glucose yield.
Figure 2B:
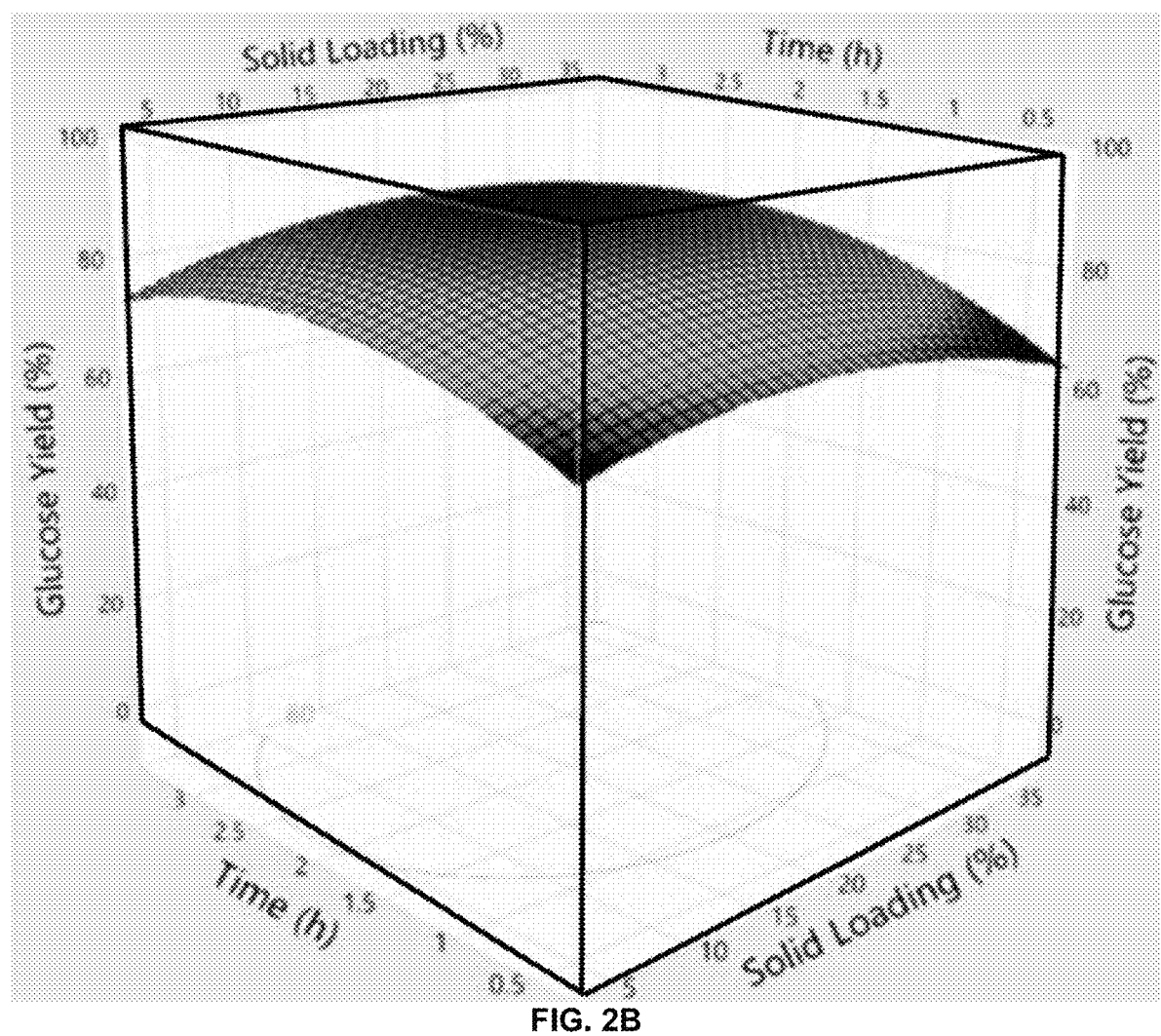
FIG. 2B. Surface response plots showing the effect of reaction time and solid loading on glucose yield.
Figure 2C:
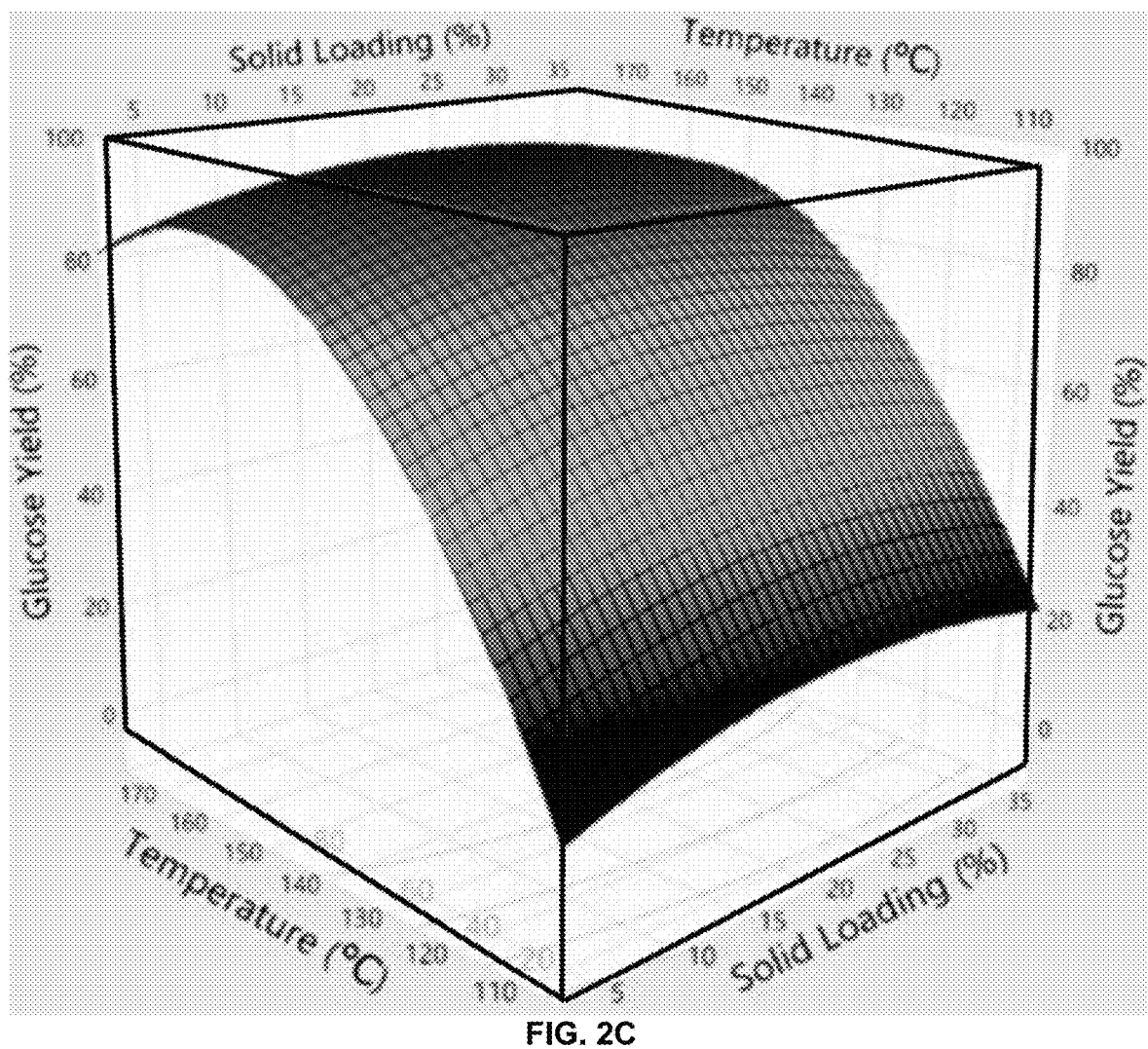
FIG. 2C. Surface response plots showing the effect of temperature and solid loading on glucose yield.
Figure 3A:
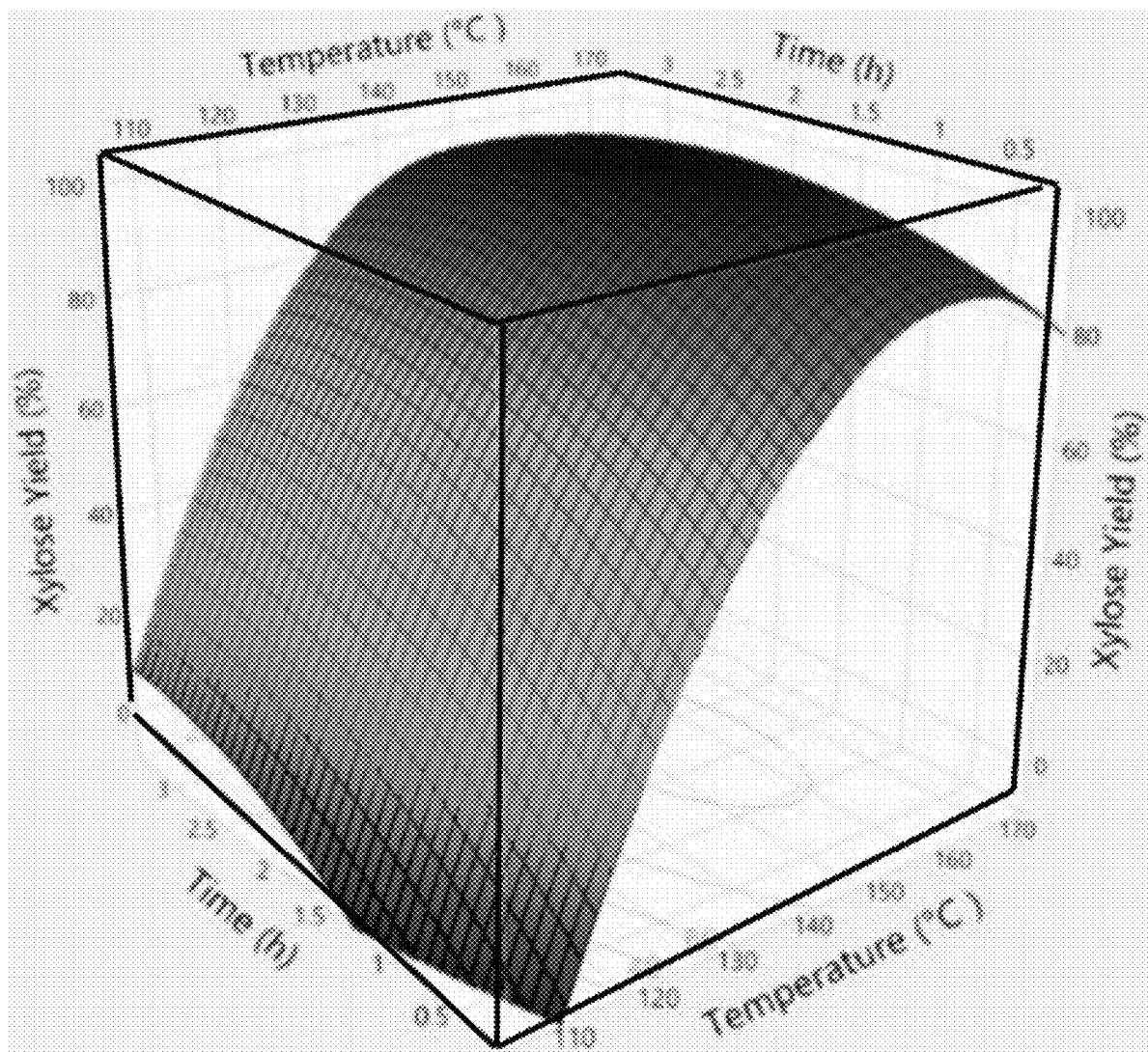
FIG. 3A. Surface response plots showing the effect of reaction time and temperature on xylose yield.
Figure 3B:
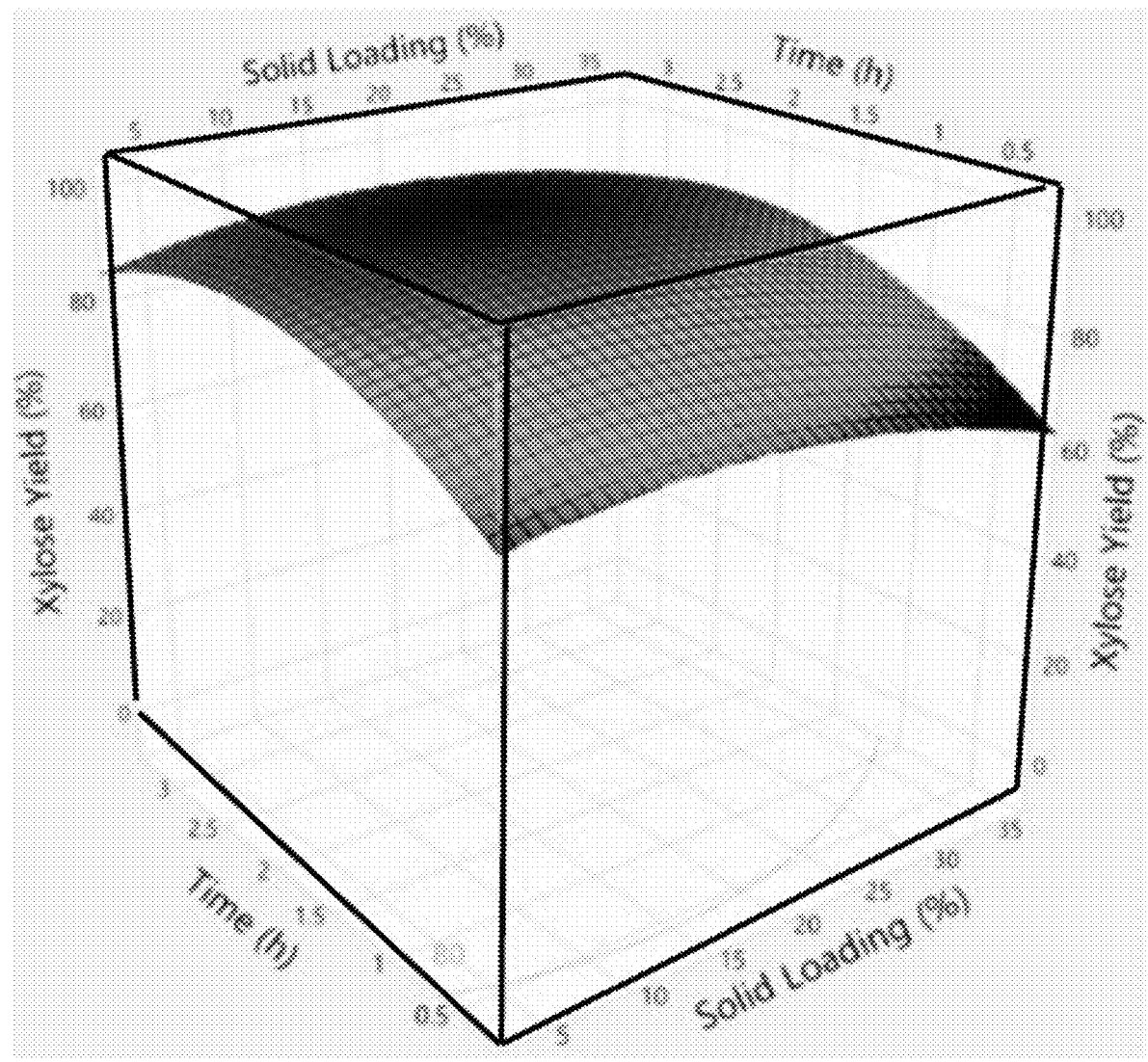
FIG. 3B. Surface response plots showing the effect of reaction time and solid loading on xylose yield.
Figure 3C:
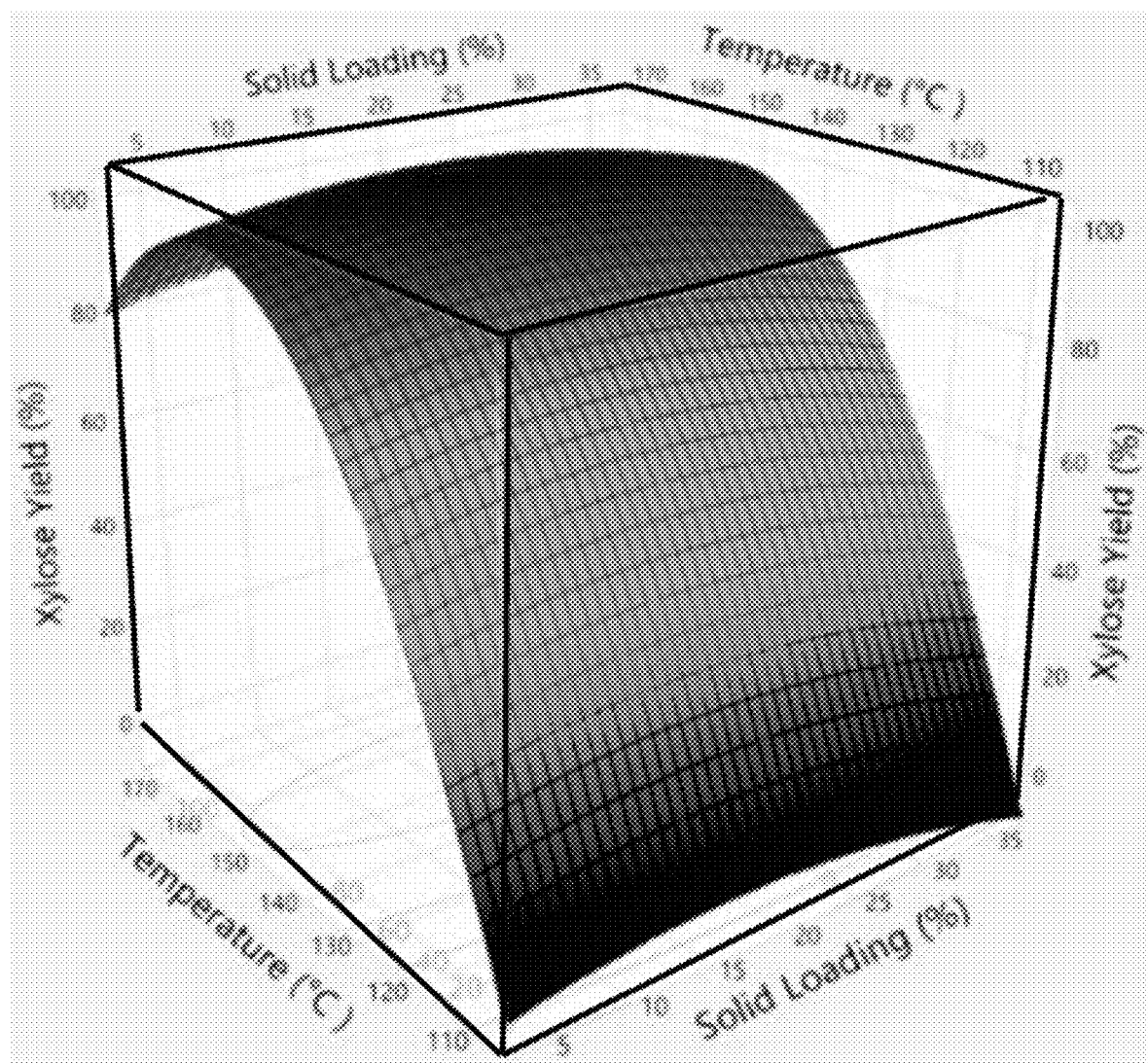
FIG. 3C. Surface response plots showing the effect of temperature and solid loading on xylose yield.
Figure 4A:
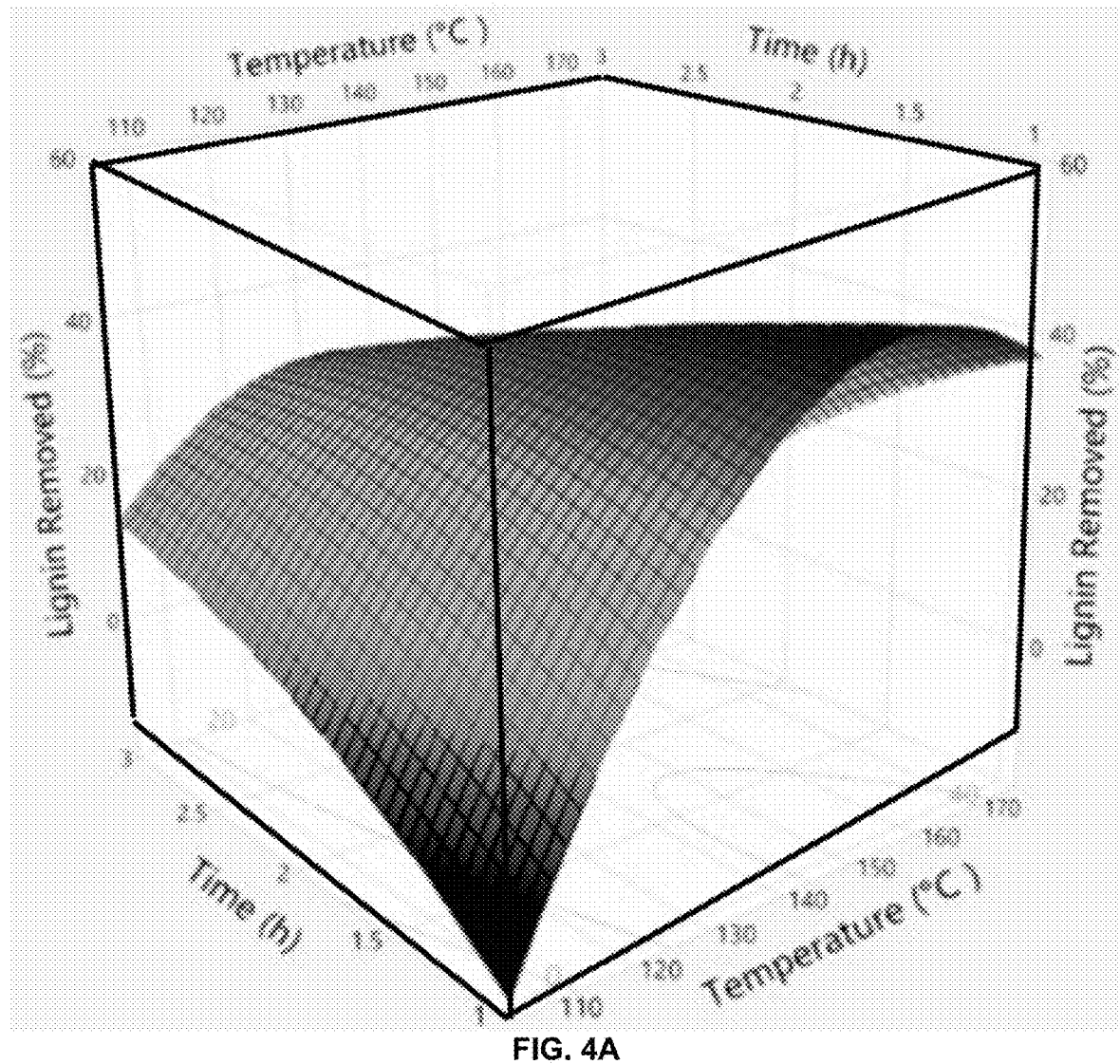
FIG. 4A. Surface response plots showing the effect of (a) reaction time and temperature (b) reaction time and solid loading (c) temperature and solid loading on lignin removal.
Figure 4B:
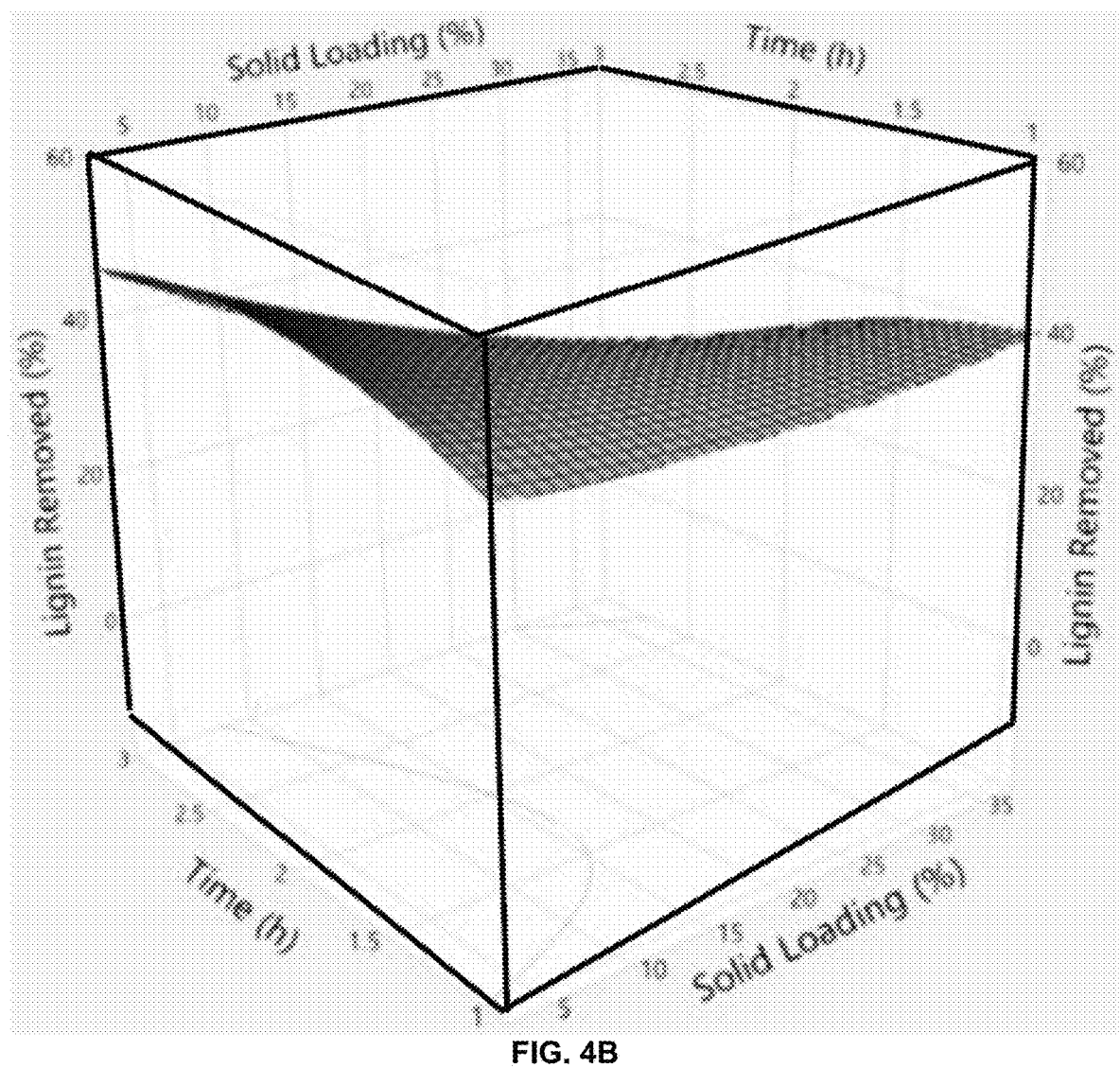
FIG. 4B. Surface response plots showing the effect of reaction time and solid loading on lignin removal.
Figure 4C:
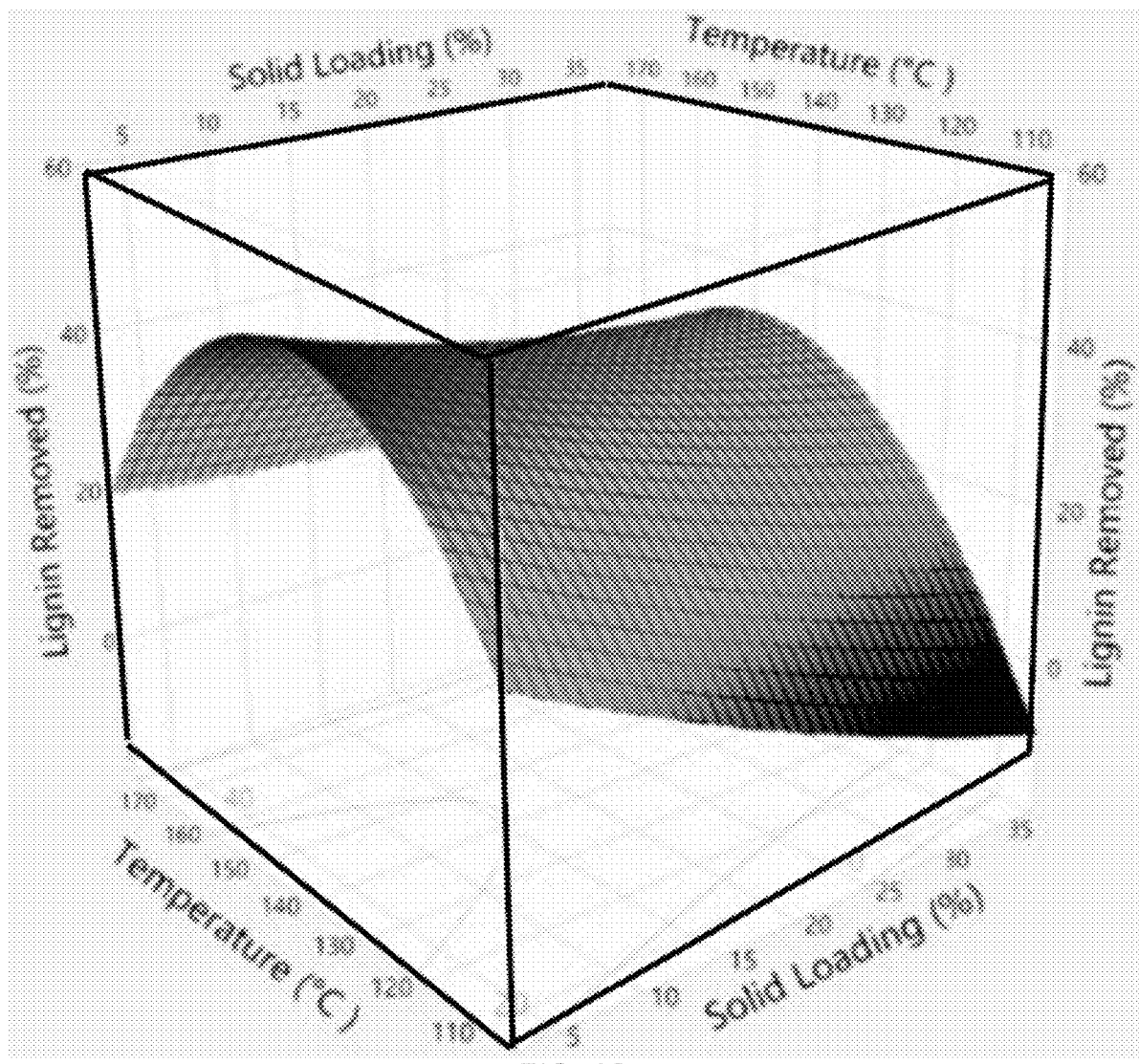
FIG. 4C. Surface response plots showing the effect of temperature and solid loading on lignin removal.
Figure 5A:
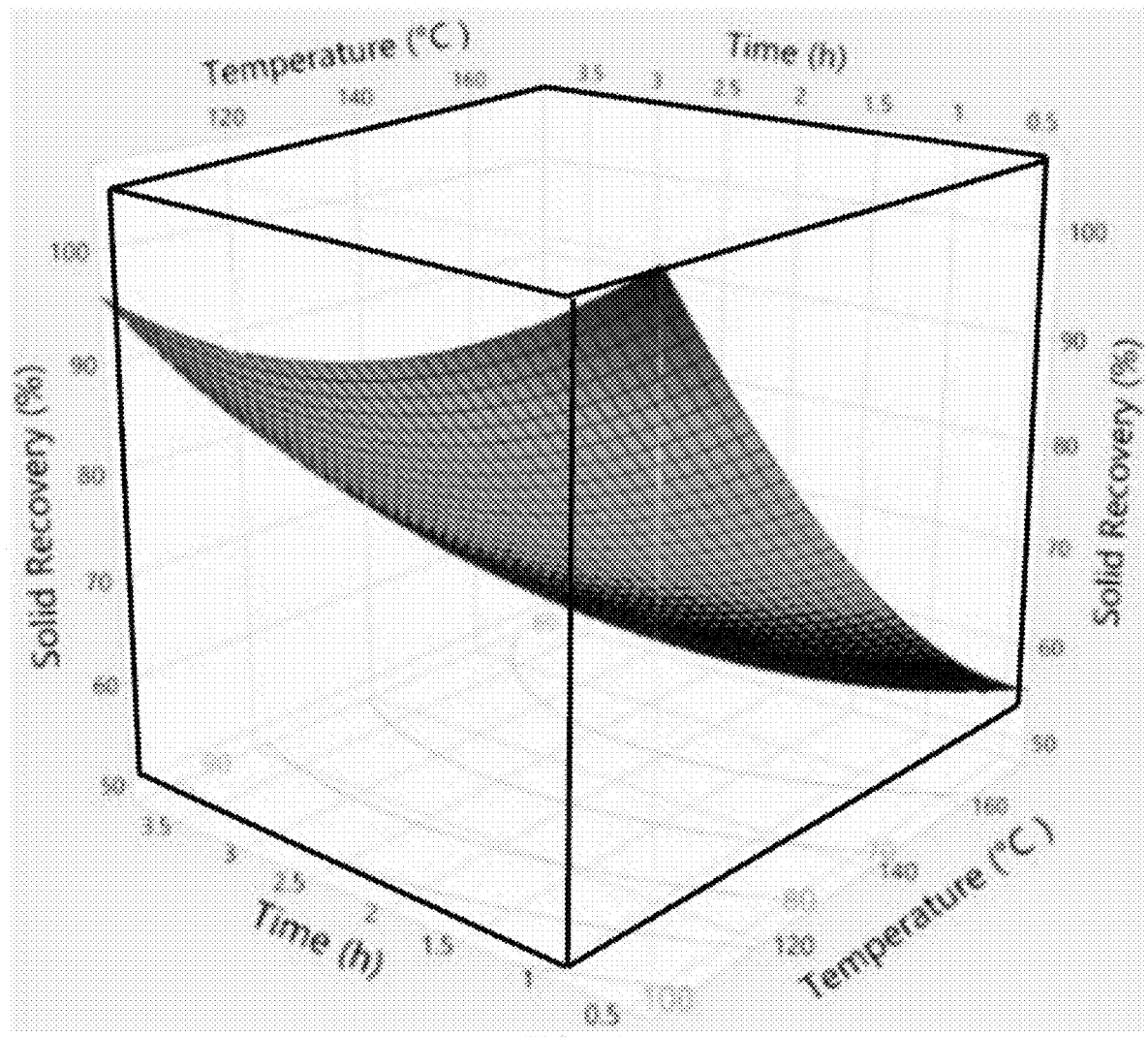
FIG. 5A. Surface response plots showing the effect of reaction time and temperature on solid recovery.
Figure 5B:
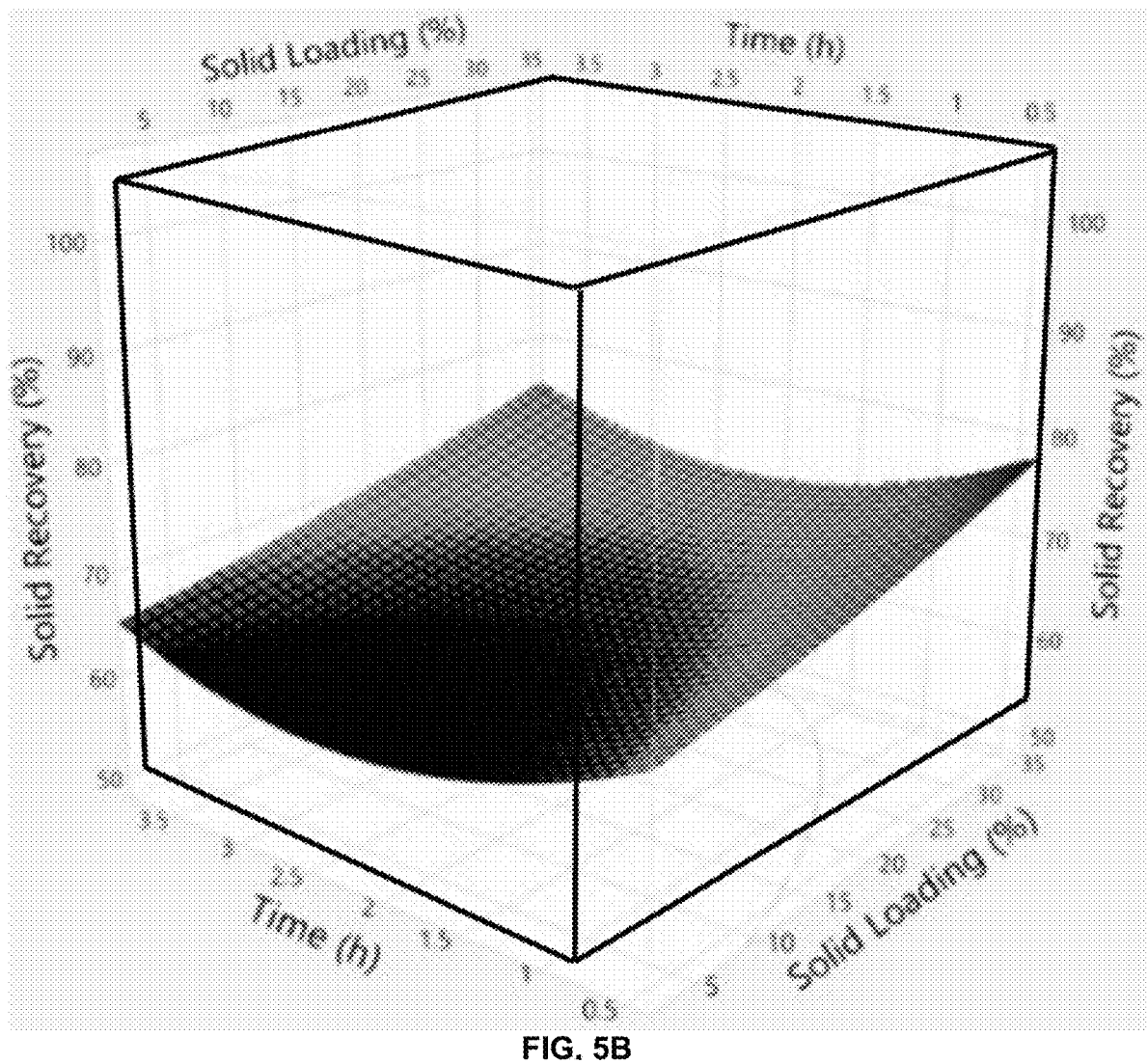
FIG. 5B. Surface response plots showing the effect of reaction time and solid loading on solid recovery.
Figure 5C:
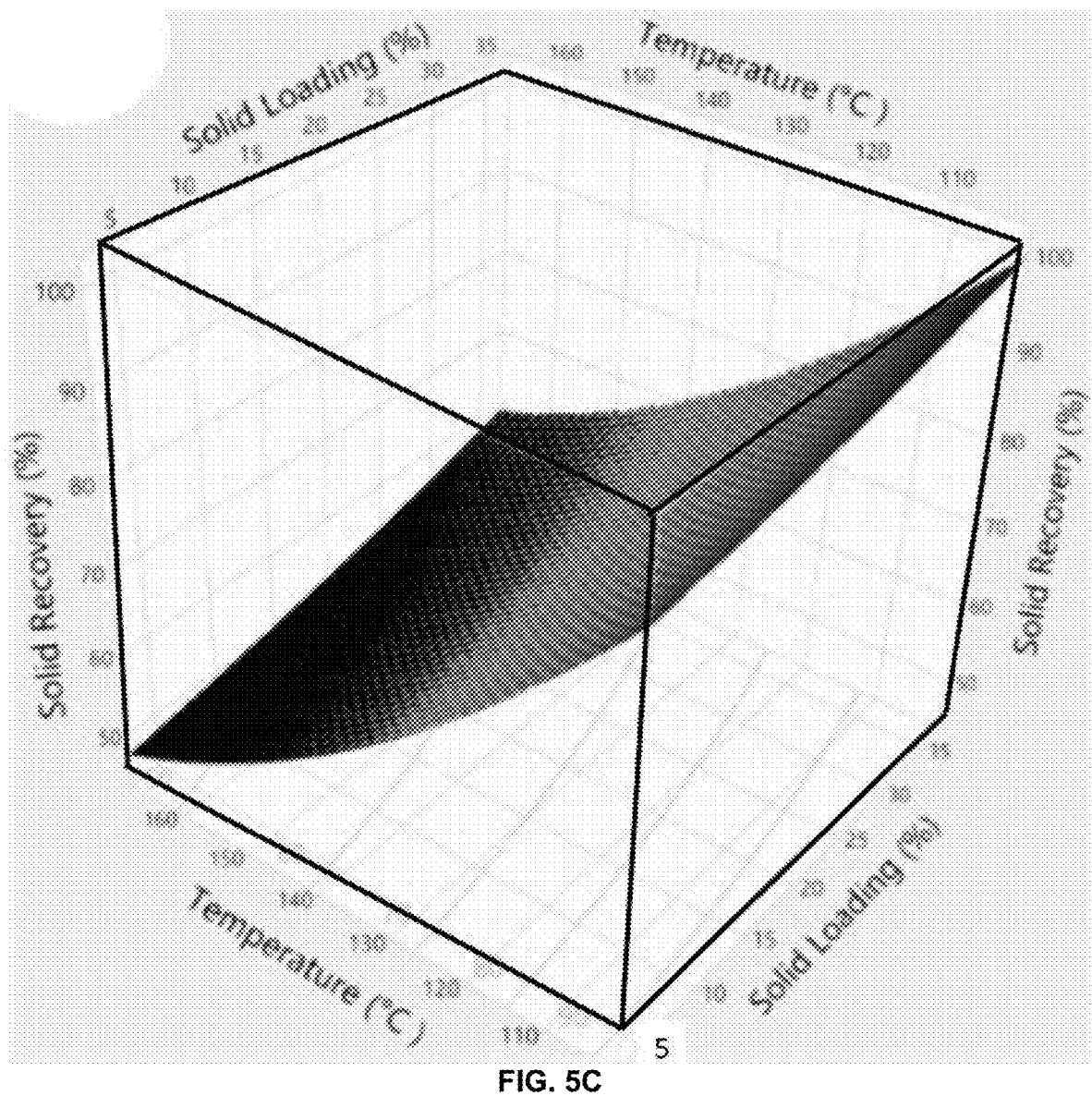
FIG. 5C. Surface response plots showing the effect of temperature and solid loading on solid recovery.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The term "about" describes a value that encompasses a value 10% less than and 10% more than the value described.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

DESs are systems formed from a eutectic mixture of Lewis or Brønsted acids and bases which can contain a variety of anionic and/or cationic species. DESs can form a eutectic point in a two-component phase system (or a more than two-component system, i.e., a three-, four-, five, six-, seven-, eight-, nine-, ten-, or more than ten-component system). DESs are formed by complexation of quaternary ammonium salts (such as, choline chloride) with hydrogen bond donors (HBD) such as amines, amides, alcohols, or carboxylic acids. The interaction of the HBD with the quaternary salt reduces the anion-cation electrostatic force, thus decreasing the melting point of the mixture. DESs share many features of conventional ionic liquid (IL), and promising applications would be in biomass processing, electrochemistry, and the like. In some embodiments, the molar ratio of the AlP to ChCl is a molar ratio depicted in FIG. 15, or within a range of any of the values depicted thereof. In some embodiments, the ratio of components of a mDES are depicted in Table 2, or within a range of any of the values depicted thereof.

Simultaneous conversion of carbohydrates and lignin to fermentable sugars and high value chemicals, respectively, hold key to the success of biorefinery and adds revenue to the pulp/paper industry. Deep eutectic solvents (DESs) have received increasing interest because of their ability in fractionation and depolymerization of lignocellulosic biomass. The metal salts accelerate the selective depolymerization of lignin.

Additionally, DESs are intrinsically cheaper than many ionic liquids (ILs) due to low precursor cost, and simple synthesis, while retaining the chemical properties of ILs. The present invention provides for a new metal based DESs (mDESs) useful for biomass pretreatment and lignin depolymerization. A portfolio of mDESs are synthesized, characterized, and screened for biomass fractionation, lignin solubility, and selectivity on lignin depolymerization. Results indicate that certain mDESs are capable of producing more than 90% of fermentable sugars. Molecular weight distribution of lignin fraction is determined via gel permeation chromatography while the extracted products were identified and quantified using GC-MS. Cleavage of the lignin structures was further investigated by NMR to better understand the alterations to lignin. One of aspect of this invention is a new approach toward biomass pretreatment with higher sugar yield and lignin depolymerization compared to other chemical and biological biomass conversion methods. In situ lignin conversion in mDESs helps to overcome the challenges associated with DES recycle and recovery.

The potential user for this invention would include paper/pulping and cellulosic biofuel industry. This technology helps achieve a higher fermentable sugar yield and transforming lignin from waste streams to valuable chemicals, and facilitates the simultaneous conversion of carbohydrates and lignin into high-value products augment the economic viability for users.

The present invention has one or more of the following advantages: (1) achieving higher (~90%) sugar yields; (2) in situ lignin conversion in mDESs helps to overcome the challenges associated with DES recycle and recovery; (3) mDES will act both as solvent and catalyst; (4) mDES is intrinsically cheaper compared other solvents; (5) limited enzyme inhibition and/or microbial toxicity, and (6) utilization of lignocellulosic biomass to its maximum potential.

In some embodiments, mDES is prepared using an alcohol (such as glycerol or ethylene glycol) and a metal halide (such as $ZnCl_2$) and heating to a temperature of from about 100° C. to about 212° C., such as about 110° C.

In some embodiments, mDES is prepared using choline chloride and a metal phosphate (such as aluminum phosphate) and heating to a temperature of from about 100° C. to about 212° C., such as about 120° C.

In some embodiments, mDES is prepared using choline chloride, alcohol or phenol or polyol and a metal phosphate and heating to a temperature of from about 100° C. to about 212° C., such as about 120° C.

mDES is capable of dissolving biomass or lignin and can be utilized in biomass pretreatment and other applications. Using mDES produced from biomass could lower the cost of biomass processing and enable greener routes for a variety of industrially relevant processes.

In some embodiments, the DES, or mixture thereof, is bio-compatible: meaning the DES, or mixture thereof, does not reduce or does not significantly reduce the enzymatic activity of the enzyme, and/or is not toxic, and/or does not reduce or significantly reduce, the growth of the microbe. A "significant" reduction is a reduction to 50, 60, 70, 80, 90, or 95% or less of the enzyme's enzymatic activity and/or the microbe's growth (or doubling time), if the DES, or mixture thereof, was not present.

The present invention provides an mDES, or mixture thereof, the mDES comprising: (a) metal salts; (b) an alcohol, or phenol or resorcinol, or polyol (such as glycol or glycerol), or amine; and (c) an organic salt such as choline chloride. In some embodiments, the metal of the metal salt is a transition metal. In some embodiments, the metal of the metal salt has a valence of +2, +3, +4, +5, or +6.

In some embodiments, the metal salt is a metal halide, metal phosphate, or metal nitrate. In some embodiments, the metal is Zn, Cu, Fe, Co, Nb, Al, Ni, Cr, or Zr.

In some embodiments, the halide is fluoride, chloride, bromide, or iodide. In some embodiments, the metal halide is $ZnCl_2$, $CuCl_2$, $CoCl_2$, $NbCl_5$, $AlCl_3$, $NiCl_2$, or $CrCl_3$.

In some embodiments, the metal phosphate is aluminum phosphate (AlP), zinc phosphate (ZnP), niobium phosphate (NbP), or zirconium phosphate (ZrP).

In some embodiments, the alcohol or polyol is a branched or straight chain alkane with one, or two or more hydroxyl groups. In some embodiments, the polyol comprises a hydroxyl group at both ends of the main carbon chain. In some embodiments, the alkane has a main carbon chain of 1 to 10 carbon atoms, or the alkane has a total of 1 to 20, or 1 to 10, carbon atoms. In some embodiments, the alkane or the main carbon chain comprises 1, 2, 3, 4, 5, 6, 7, 8, 9, or 10 carbon atoms. In some embodiments, the alkane, or the main carbon chain thereof, is substituted with one or more amino group. In some embodiments, the glycol is ethylene glycol.

In some embodiments, the amine is a branched or straight chain alkane with (i) two or more amino groups, or (ii) a hydroxyl group and one or more amine groups. In some embodiments, the amine comprises an amino group at both ends of the main carbon chain. In some embodiments, the alkane has a main carbon chain of 1 to 10 carbon atoms, or the alkane has a total of 1 to 20, or 1 to 10, carbon atoms. In some embodiments, the alkane or the main carbon chain comprises 1, 2, 3, 4, 5, 6, 7, 8, 9, or 10 carbon atoms. In some embodiments, the alkane, or the main carbon thereof, is substituted with one or more hydroxyl group. In some embodiments, the amine is a secondary or tertiary amine comprising two or more organic substituents. In some embodiments, the secondary or tertiary amine comprises a cyclic amine. In some embodiments, each organic substituent independently, or together, or every organic substituent, comprises one or more hydroxyl groups and/or one or more amine groups. In some embodiments, each organic substituent comprises 1, 2, 3, 4, 5, 6, 7, 8, 9, or 10 hydroxyl groups and/or amine groups, or a mixture thereof. In some embodiments, the cyclic amine comprises one or more ether groups.

In some embodiments, the polyol or amine comprises the following chemical structure:

R—(CH$_2$)$_n$—R (I);

wherein n is 1, 2, 3, 4, 5, 6, 7, 8, 9, or 10, and each R is independently —NH$_2$ or —OH. In some embodiments, both R's are —NH$_2$. In some embodiments, both R's are —OH.

In some embodiments, the amine comprises chemical structure (I) and further comprising one or more alkyl substituent.

In some embodiments, the amine comprises the following chemical structure:

(II)

wherein R$^1$ is H, or an alkyl group comprising 1, 2, 3, 4, 5, 6, 7, 8, 9, or 10 carbon atoms, R$^2$ and R$^3$ are each independently an alkyl group comprising 1, 2, 3, 4, 5, 6, 7, 8, 9, or 10 carbon atoms, wherein each alkyl group optionally comprises one more substituents, such as an alkyl group, NH$_2$, and/or —OH.

In some embodiments, the amine is 1,2-diaminopropane, 1,3-diaminopropane, diethylenetriamine, putrescine, cadaverine, ethylenediamine, 2-methylethanolamine, 1-amino-2-propanol, bis(3-aminopropyl)amine, morpholine, or ethanolamine.

In some embodiments, the mDES comprises a 1:4 molar ratio of ZnCl$_2$:ethylene glycol.

In some embodiments, the mDES comprises a 1:4 molar ratio of ZnCl$_2$:gylcerol.

In some embodiments, the mDES comprises a ZnCl$_2$ molar concentration having a range from 2.44% to 70%.

In some embodiments, the biomass and mDES composition of step (a) comprises a ZnCl$_2$ molar concentration having a range from 2% to 16%.

In some embodiments, the solvent comprises a DES wherein the DES is a two-component system, a three-component system, or a more than three-component system.

In some embodiments, a lignin in the biomass is converted into a monomer, a dimer, a trimer, or a mixture thereof. In some embodiments, a lignin in the biomass is depolymerized.

In some embodiments, the method comprises a separating the solid and the liquid step and/or a washing step between step (a) and step (b). In some embodiments, the separating step comprises decanting, filtering, and/or centrifuging the composition. In some embodiments, the washing step comprises washing with an alcohol:water solution, such as ethanol:water, having an alcohol to water ratio of about 0:10, 1:10, 2:10, 3:10, 4:10, 5:10, 6:10, 7:10, 8:10, 9:10, 10:10, 10:9, 10:8, 10:7, 10:6, 10:5, 10:4, 10:3, 10:2, 10:1, or 10:0. In some embodiments, the alcohol is any alkanol. In some embodiments, the alkanol has between 1 to 10 carbon atoms.

After pretreatment, there is a solid/liquid separation and ethanol:water (1:1) washing.

In some embodiments, the composition of step (a) has a temperature of from about 100° C. to about 212° C. In some embodiment, the composition has a temperature of from about 100° C. to about 200° C. In some embodiment, the composition has a temperature of from about 120° C. to about 180° C.

In some embodiments, the method further comprising a heating step after step (a), wherein the heating step is heating the composition to a temperature of from about 100° C. to about 212° C. in some embodiment, the heating step is heating the composition to a temperature of from about 100° C. to about 200° C. in some embodiment, the heating step is heating the composition to a temperature of from about 120° C. to about 180° C.

In some embodiments, the method further comprises heating the composition, optionally also comprising the enzyme and/or microbe, to a temperature that is equal to, about, or near the optimum temperature for the enzymatic activity of the enzyme and/or growth of the microbe. In some embodiments, the enzyme is a genetically modified host cell capable of converting the cellulose in the biomass into a sugar. In some embodiments, there is a plurality of enzymes. In some embodiments, the microbe is a genetically modified host cell capable of converting a sugar produced from the biomass into a biofuel and/or chemical compound. In some embodiments, there is a plurality of microbes. In some embodiments, the introducing steps (a) and (b) together produce a sugar and a lignin from the biomass. The sugar is used for growth by the microbe.

In some embodiments, the enzyme is a cellulase. In some embodiments, the enzyme is a cellulase. In some embodiments, the enzyme is thermophilic or hyperthermophilic. In some embodiments, the enzyme is any enzyme taught in U.S. Pat. Nos. 9,322,042; 9,376,728; 9,624,482; 9,725,749; 9,803,182; and 9,862,982; and PCT International Patent Application Nos. PCT/US2015/000320, PCT/US2016/063198, PCT/US2017/036438, PCT/US2010/032320, and PCT/US2012/036007 (all of which are incorporated in their entireties by reference).

In some embodiments, the microbe is any prokaryotic or eukaryotic cell, with any genetic modifications, taught in U.S. Pat. Nos. 7,985,567; 8,420,833; 8,852,902; 9,109,175; 9,200,298; 9,334,514; 9,376,691; 9,382,553; 9,631,210; 9,951,345; and 10,167,488; and PCT International Patent Application Nos. PCT/US14/48293, PCT/US2018/049609, PCT/US2017/036168, PCT/US2018/029668, PCT/US2008/068833, PCT/US2008/068756, PCT/US2008/068831, PCT/US2009/042132, PCT/US2010/033299, PCT/US2011/053787, PCT/US2011/058660, PCT/US2011/059784, PCT/US2011/061900, PCT/US2012/031025, and PCT/US2013/074214 (all of which are incorporated in their entireties by reference).

In some embodiments, the biofuel produced is ethanol, or any other organic molecule, described produced in a cell taught in U.S. Pat. Nos. 7,985,567; 8,420,833; 8,852,902; 9,109,175; 9,200,298; 9,334,514; 9,376,691; 9,382,553; 9,631,210; 9,951,345; and 10,167,488; and PCT International Patent Application Nos. PCT/US14/48293, PCT/US2018/049609, PCT/US2017/036168, PCT/US2018/029668, PCT/US2008/068833, PCT/US2008/068756, PCT/US2008/068831, PCT/US2009/042132, PCT/US2010/033299, PCT/US2011/053787, PCT/US2011/058660, PCT/US2011/059784, PCT/US2011/061900, PCT/US2012/031025, and PCT/US2013/074214 (all of which are incorporated in their entireties by reference).

Lignin is the second most abundant naturally occurring polymer next to cellulose, which represents a significant component of carbon on earth. Large amount of technical lignins such as Kraft lignin and lignosulfonate is produced as by-products in the pulp and paper industries. It is also expected that more lignin will become available in coming years as the production capability of second generation of biofuels increases. As a renewable and resource, lignin and lignin derived products (phenolic) are an important material.

In some embodiments, the biomass is a lignocellulosic biomass. In some embodiments, the vessel is made of a material that is inert, such as stainless steel or glass, which does not react or interfere with the reactions in the composition.

In some embodiments, the pretreatment comprises biomass (such as corn stover) within a range of 1 g to 3 g mixed thoroughly with mDES ($ZnCl_2$:glycerol) within a range of 7 g to 9 g in a suitable inert vessel, such as a glass vessel, followed by heating up to a temperature within the range of 100° C. to 212° C. The temperature is maintained for a suitable period of time, such as about 2 hours. After pretreatment, approximately 25 mL of ethanol is added to the resulting slurry and the composition is centrifuged to about 45000 rpm. The saccharification is carried out with a suitable enzyme, such as a commercial enzyme mixture (for example, a 9:1 v/v ratio of HTec3 and CTec3 from Novozymes A/S (Bagsverd, Denmark), at about 50° C. at about 48 rpm in an incubator with shaking function. After a suitable period of time, such as about 48 or 72 hours, of saccharification, the generated sugar stream can be used for microbial conversion. For example, a wild-type yeast, such as *Saccharomyces cerevisiae*, is inoculated at temperature (about 30° C. to about 37° C.) for anaerobic ethanol fermentation.

In some embodiments, the method does not require recycling any catalyst and/or enzyme. In some embodiments, the method requires less water usage than current biomass pretreatment.

In some embodiments, the method provides for a cooperative catalysis of metal salts and hybrid solvents for full utilization of lignocellulosic biomass. In some embodiments, the method comprises a full utilization of lignocellulosic biomass through the combination of metal salts and hybrid solvents, such as ionic liquids (ILs) or deep eutectic solvents (DESs). This method provides a facile and biocompatible fractionation pathway to afford fermentable sugars along with oligomeric lignin simultaneously.

In some embodiments, the lignocellulosic biomass (such as comprising cellulose, hemicellulose, and/or lignin) offers many advantages as a renewable feedstock for the production of fuels and chemicals. Current methods have focused on the utilization of more readily processed carbohydrates leaving behind lignin either as a waste or to be burnt. The partial utilization of biomass and burning of lignin raises significant economic and environmental concerns. In some embodiments, the method fractionates the biopolymers and convert lignin to oligomers (such as, by cleaving dominant ether linkages within the lignin). In some embodiments, the method comprises using controlled upgradation under milder conditions. Lignin produced by traditional methods is technical grade lignin, i.e., a condensed form of lignin that is hard to upgrade into chemicals and therefore is a waste and eventually can only burnt. The present invention provides for a method to utilize all components, including the lignin. A lignin-first method concept is introduced where hydrogenolysis at higher temperatures has been employed restricting control over reaction products. Nevertheless, the use of high temperatures and harsher conditions results in lower sugar yields and allow a limited control on aromatic profile.

Pretreatment of biomass using modern solvents such as ionic liquids (ILs) or deep eutectic solvents (DESs) is known as an efficient method to fractionate biomass components.

In some embodiment, the method uses a metal salt in combination with ILs or DESs in order to enable the full utilization of lignocellulosic biomass under mild conditions. Examples of DES are obtained by mixing choline chloride with either glycerol or resorcinol, whereas ILs tested in combination are cholinium lysinate and cholinium lysinate palmitate. Each IL or DES, or a mixture thereof, is combined with a metal phosphates, such as aluminum, niobium and zirconium phosphates for biomass pretreatment. Using such methods, the product profiles of depolymerized biopolymers (qualitatively and quantitatively) along with the molecular weight distribution profile as a function of reaction coordinates are obtained. Notably, the employed system not only achieves oligomeric lignin fractions and about 85% glucose (at 20 wt % biomass loading), but also had negligible or no microbial toxicity, thereby opening the possibility for a subsequent biological conversion of the depolymerized stream or streams. The process configuration can further be optimized in terms of temperature, ratio or amounts of individual components, sugar yields, recycling, or the like. The potential uses for this method include the full utilization biomass into chemicals, biomaterials, biofuels, and bioproducts.

In some embodiments, the method provides for a metal phosphates-based deep eutectic solvents for biomass pretreatment. This method comprises preparing a metal phosphate-based deep eutectic solvent (DES) and employing the prepared DES to pretreat lignocellulosic biomass. In some embodiments, the metal phosphate DES system achieves an about 70% glucose and about 25% lignin monomer yields at 20 wt % solid loading, and it also had a limited enzyme inhibition and microbial toxicity (more than about 5 wt %), opening the possibility for a subsequent biological conversion of the depolymerized stream(s). In some embodiments, the limited enzyme inhibition means the inhibition of enzymatic activity of the enzyme by the solvent is less than or equal to 50%, 10%, 5% or 1% compared to when the solvent is absent. In some embodiments, the limited microbial toxicity means the toxicity or inhibition on the growth or viability of the microbe by the solvent is less than or equal to 50%, 10%, 5% or 1% compared to when the solvent is absent.

Lignocellulosic biomass offers many advantages as a renewable feedstock for the production of fuels and chemicals. A major constraint in the efficient utilization of biomass is the structural arrangement of its constituent biopolymers (cellulose, hemicellulose, and lignin) and their limited solubility in traditional solvents.

The discovery of alternative solvents such as deep eutectic solvents (DESs, eutectic mixtures of two or more hydrogen bond donors/acceptors) have mitigated the processing of biomass to some extent. Most of the existing DESs have shown excellent biopolymer solubility, but a restricted focus on sugar release by delignification rather than depolymerization of lignin dominates the literature. From an economic viewpoint, the coupling of dissolution and depolymerization/conversion of both cellulose and lignin is an ideal route for minimizing energy and cost. On another note, metal catalysts have been widely incorporated in various organic transformations, including conversion of lignin model compounds.

In some embodiments, the method is capable of coupling dissolution and depolymerization/conversion of these biopolymers using metal-based DESs. In some embodiments, the method uses a metal chlorides-based DES that is efficacious for the release of sugars from the biomass. A disadvantage of using a metal halide is that the metal halide is not fully compatible with certain downstream processes and/or causes certain recycling limitations. Metal phosphates, on the other hand, are completely insoluble in water facilitating downstream processes and provide possibilities of recyclability. Metal phosphates are also known for containing both Lewis and Bronsted acidic sites, ideal for ether bond cleavage (dominant linkages in lignin).

In some embodiments, the method uses aluminum phosphate containing two or three component DES in various unique ratios. In some embodiments, the method uses a two- or three-component DES comprises The chemical compounds employed as second or third components are urea, choline chloride, glycerol, and ethylene glycol. Solid loadings are attempted up to 50 wt %. The product profiles of depolymerized biopolymers (qualitatively and quantitatively) are studied along with the molecular weight distribution profile as a function of reaction coordinates. Notably, the employed DES system not only achieve about 70% glucose and about 25% lignin monomer yields, but also have limited enzyme inhibition and microbial toxicity (more than 5 wt %), opening the possibility for a subsequent biological conversion of the depolymerized stream or streams. Optimized pretreatment process in terms of component combinations, ratio or amounts of individual components, reaction coordinates, sugar yields, lignin profile, recycling, etc. can be carried out and determined.

In some embodiments, the method is useful for converting waste biomass (such as agricultural residues, wood/paper/pulping, and/or grasses) into biofuels and/or bioproducts. In some embodiments, the method achieves high concentration of fermentable sugars while leaving the residual oligomeric lignin for valuable chemicals.

This method offers one or more economic advantages over the current state-of-art including one or more of the following: (1) Simultaneous lignin processing during pretreatment of lignocellulosic biomass. (2) Reduced amounts of metal salts. (3) Compatible with downstream processes. (4) Possible recycling of metals catalysts. (5) Precise control over aromatic and hydrocarbon product profile. (6) Biomass type versatility.

Ionic Liquid

Ionic liquids (ILs) are salts that are liquids rather than crystals at room temperatures. It will be readily apparent to those of skill that numerous ILs can be used in the present invention. In some embodiments of the invention, the IL is suitable for pretreatment of the biomass and for the hydrolysis of cellulose by thermostable cellulase. Suitable ILs are taught in ChemFiles (2006) 6 (9) (which are commercially available from Sigma-Aldrich, Milwaukee, Wis.). Such suitable ILs include, but are not limited to, 1-alkyl-3-alkylimidazolium alkanate, 1-alkyl-3-alkylimidazolium alkylsulfate, 1-alkyl-3-alkylimidazolium methylsulfonate, 1-alkyl-3-alkylimidazolium hydrogensulfate, 1-alkyl-3-alkylimidazolium thiocyanate, and 1-alkyl-3-alkylimidazolium halide, wherein an "alkyl" is an alkyl group comprising from 1 to 10 carbon atoms, and an "alkanate" is an alkanate comprising from 1 to 10 carbon atoms. In some embodiments, the "alkyl" is an alkyl group comprising from 1 to 4 carbon atoms. In some embodiments, the "alkyl" is a methyl group, ethyl group or butyl group. In some embodiments, the "alkanate" is an alkanate comprising from 1 to 4 carbon atoms. In some embodiments, the "alkanate" is an acetate. In some embodiments, the halide is chloride.

In some embodiments, the IL includes, but is not limited to, 1-ethyl-3-methylimidazolium acetate (EMIN Acetate), 1-ethyl-3-methylimidazolium chloride (EMIN Cl), 1-ethyl-3-methylimidazolium hydrogensulfate (EMIM $HOSO_3$), 1-ethyl-3-methylimidazolium methylsulfate (EMIM $MeOSO_3$), 1-ethyl-3-methylimidazolium ethylsulfate (EMIM $EtOSO_3$), 1-ethyl-3-methylimidazolium methanesulfonate (EMIM $MeSO_3$), 1-ethyl-3-methylimidazolium tetrachloroaluminate (EMIM $AlCl_4$), 1-ethyl-3-methylimidazolium thiocyanate (EMIM SCN), 1-butyl-3-methylimidazolium acetate (BMIM Acetate), 1-butyl-3-methylimidazolium chloride (BMIM Cl), 1-butyl-3-methylimidazolium hydrogensulfate (BMIM $HOSO_3$), 1-butyl-3-methylimidazolium methanesulfonate (BMIM $MeSO_3$), 1-butyl-3-methylimidazolium methylsulfate (BMIM $MeOSO_3$), 1-butyl-3-methylimidazolium tetrachloroaluminate (BMIM $AlCl_4$), 1-butyl-3-methylimidazolium thiocyanate (BMIM SCN), 1-ethyl-2,3-dimethylimidazolium ethylsulfate (EDIM $EtOSO_3$), Tris(2-hydroxyethyl)methylammonium methylsulfate (MTEOA $MeOSO_3$), 1-methylimidazolium chloride (MIM Cl), 1-methylimidazolium hydrogensulfate (MIM $HOSO_3$), 1,2,4-trimethylpyrazolium methylsulfate, tributylmethylammonium methylsulfate, choline acetate, choline salicylate, and the like.

In some embodiments, the ionic liquid is a chloride ionic liquid. In other embodiments, the ionic liquid is an imidazolium salt. In still other embodiments, the ionic liquid is a 1-alkyl-3-imidazolium chloride, such as 1-ethyl-3-methylimidazolium chloride or 1-butyl-3-methylimidazolium chloride.

In some embodiments, the ionic liquids used in the invention are pyridinium salts, pyridazinium salts, pyrimidium salts, pyrazinium salts, imidazolium salts, pyrazolium salts, oxazolium salts, 1,2,3-triazolium salts, 1,2,4-triazolium salts, thiazolium salts, isoquinolium salts, quinolinium salts isoquinolinium salts, piperidinium salts and pyrrolidinium salts. Exemplary anions of the ionic liquid include, but are not limited to halogens (e.g., chloride, fluoride, bromide and iodide), pseudohalogens (e.g., azide and isocyanate), alkyl carboxylate, sulfonate, acetate and alkyl phosphate.

Additional ILs suitable for use in the present invention are described in U.S. Pat. Nos. 6,177,575; 9,765,044; and, 10,155,735; U.S. Patent Application Publication Nos. 2004/0097755 and 2010/0196967; and, PCT International Patent Application Nos. PCT/US2015/058472, PCT/US2016/063694, PCT/US2017/067737, and PCT/US2017/036438 (all of which are incorporated in their entireties by reference). It will be appreciated by those of skill in the art that others ILs that will be useful in the process of the present invention are currently being developed or will be developed in the future, and the present invention contemplates their future use. The ionic liquid can comprise one or a mixture of the compounds.

In some embodiments, the IL is a protic ionic liquid (PIL). Suitable protic ionic liquids (PILs) include fused salts with a melting point less than 100° C. with salts that have higher melting points referred to as molten salts. Suitable PPILs are disclosed in Greaves et al. "Protic Ionic Liquids: Properties and Applications" *Chem. Rev.* 108(1):206-237 (2008). PILs can be prepared by the neutralization reaction of certain Brønsted acids and Brønsted bases (generally from primary, secondary or tertiary amines, which are alkaline) and the fundamental feature of these kinds of ILs is that their cations have at least one available proton to form hydrogen bond with anions. In some embodiments, the protic ionic liquids (PILs) are formed from the combination of organic ammonium-based cations and organic carboxylic acid-based anions. PILs are acid-base conjugate ILs that can be synthesized via the direct addition of their acid and base precursors. In some embodiments, the PIL is a hydroxyalkylammonium carboxylate. In some embodiments, the hydroxyalkylammonium comprises a straight or branched C1, C2, C3, C4, C5, C6, C7, C8, C9, or C10 chain. In some embodiments, the carboxylate comprises a straight or branched C1, C2, C3, C4, C5, C6, C7, C8, C9, or C10 chain. In some embodiments, the carboxylate is substituted with one or more hydroxyl groups. In some embodiments, the PIL is a hydroxyethylammonium acetate.

In some embodiments, the protic ionic liquid (PIL) is disclosed by U.S. Patent Application Publication No. 2004/0097755, hereby incorporated by reference.

Suitable salts for the method include combinations of organic ammonium-based cations (such as ammonium, hydroxyalkylammonium, or dimethylalkylammonium) with organic carboxylic acid-based anions (such as acetic acid derivatives (C1-C8), lactic acid, glycolic acid, and DESs such as ammonium acetate/lactic acid).

Suitable IL, such as distillable IL, are disclosed in Chen et al. "Distillable Ionic Liquids: reversible Amide O Alkylation", *Angewandte Comm.* 52:13392-13396 (2013), King et al. "Distillable Acid-Base Conjugate Ionic Liquids for Cellulose Dissolution and Processing", *Angewandte Comm.* 50:6301-6305 (2011), and Vijayaraghavan et al. "$CO_2$-based Alkyl Carbamate Ionic Liquids as Distillable Extraction Solvents", *ACS Sustainable Chem. Engin.* 2:31724-1728 (2014), all of which are hereby incorporated by reference.

Suitable PIL, such as distillable PIL, are disclosed in Idris et al. "Distillable Protic Ionic Liquids for Keratin Dissolution and Recovery", *ACS Sustainable Chem. Engin.* 2:1888-1894 (2014) and Sun et al. "One-pot integrated biofuel production using low-cost biocompatible protic ionic liquids", *Green Chem.* 19(13):3152-3163 (2017), all of which are hereby incorporated by reference.

In some embodiments, the PILs are formed with the combination of organic ammonium-based cations and organic carboxylic acid-based anions. PILs are acid-base conjugate ILs that can be synthesized via the direct addition of their acid and base precursors. Additionally, when sufficient energy is employed, they can dissociate back into their neutral acid and base precursors, while the PILs are reformed upon cooling. This presents a suitable way to recover and recycle the ILs after their application. In some embodiments, the PIL (such as hydroxyethylammonium acetate—[Eth][OAc]) is an effective solvent for biomass pretreatment and is also relatively cheap due to its ease of synthesis (Sun et al., *Green Chem.* 19(13):3152-3163 (2017)).

Deep Eutectic Solvent (DES)

DESs are systems formed from a eutectic mixture of Lewis or Brønsted acids and bases which can contain a variety of anionic and/or cationic species. DESs can form a eutectic point in a two-component phase system. DESs are formed by complexation of quaternary ammonium salts (such as, choline chloride) with hydrogen bond donors (HBD) such as amines, amides, alcohols, or carboxylic acids. The interaction of the HBD with the quaternary salt reduces the anion-cation electrostatic force, thus decreasing the melting point of the mixture. DESs share many features of conventional ionic liquid (IL), and promising applications would be in biomass processing, electrochemistry, and the like. In some embodiments, the DES is any combination of Lewis or Brønsted acid and base. In some embodiments, the Lewis or Brønsted acid and base combination used is distillable.

In some embodiments, DES is prepared using an alcohol (such as glycerol or ethylene glycol), amines (such as urea), and an acid (such as oxalic acid or lactic acid). The present invention can use renewable DESs with lignin-derived phenols as HBDs. Both phenolic monomers and phenol mixture readily form DES upon heating at 100° C. with specific molar ratio with choline chloride. This class of DES does not require a multistep synthesis. The DES is synthesized from lignin which is a renewable source.

Both monomeric phenols and phenol mixture can be used to prepare DES. DES is capable of dissolving biomass or lignin, and can be utilized in biomass pretreatment and other applications. Using DES produced from biomass could lower the cost of biomass processing and enable greener routes for a variety of industrially relevant processes.

The DES, or mixture thereof, is bio-compatible: meaning the DES, or mixture thereof, does not reduce or does not significantly reduce the enzymatic activity of the enzyme, and/or is not toxic, and/or does not reduce or significantly reduce, the growth of the microbe. A "significant" reduction is a reduction to 70, 80, 90, or 95% or less of the enzyme's enzymatic activity and/or the microbe's growth (or doubling time), if the DES, or mixture thereof, was not present.

In some embodiments, the DES, or mixture thereof, comprises a quaternary ammonium salt and/or glycerol. In some embodiments, the DES, or mixture thereof, comprises a quaternary ammonium salt and/or glycerol. In some embodiments, the quaternary ammonium salt and/or glycerol have a molar ratio of about 1:1 to about 1:3. In some embodiments, the quaternary ammonium salt and/or glycerol have a molar ratio of about 1:1.5 to about 1:2.5. In some embodiments, the quaternary ammonium salt and/or glycerol have a molar ratio of about 1:1.8 or 1:1.9 to about 1:2.1 or 1:2.2. In some embodiments, the quaternary ammonium salt and/or glycerol have a molar ratio of about 1:2. In some embodiments, the quaternary ammonium salt is a choline halide, such choline chloride.

In some embodiments, the DES is distillable if the DES can be recovered at least equal to or more than about 50%, 55%, 60%, 65%, 70%, 75%, 80%, or 85% yield by distilling over vacuum at a temperature at about 100° C., 110° C., 120° C., 130° C., 140° C., 150° C., or 160° C., or any temperature between any two of the preceding temperatures.

In some embodiments, the DES can be one taught in WO 2018/204424 (Seema Singh et al.), which is hereby incorporated in its entirety by reference.

In some embodiments, the method further comprises heating the one-pot composition, optionally also comprising the enzyme and/or microbe, to a temperature that is equal to, about, or near the optimum temperature for the enzymatic activity of the enzyme and/or growth of the microbe. In some embodiments, the enzyme is a genetically modified host cell capable of converting the cellulose in the biomass into a sugar. In some embodiments, there is a plurality of enzymes. In some embodiments, the microbe is a genetically modified host cell capable of converting a sugar produced from the biomass into a biofuel and/or chemical compound. In some embodiments, there is a plurality of microbes. In some embodiments, the introducing step(s) produce a sugar and a lignin from the biomass. The lignin can further be processed to produce a DES. The sugar is used for growth by the microbe.

In some embodiments, the solubilizing is full, near full (such as at least about 70, 80, or 90%), or partial (such as at least about 10, 20, 30, 40, 50, or 60%). In some embodiments, the one-pot composition is a slurry. When the steps described herein are continuous, the one-pot composition is in a steady state.

In some embodiments, the introducing step comprises heating the mixture comprises increasing the temperature of the solution to a value within a range of about 75° C. to about 125° C. In some embodiments, the heating step comprises increasing the temperature of the solution to a value within a range of about 80° C. to about 120° C. In some embodiments, the heating step comprises increasing the temperature of the solution to a value within a range of about 90° C. to about 110° C. In some embodiments, the heating step comprises increasing the temperature of the solution to about 100° C.

Enzyme

In some embodiments, the enzyme is a cellulase and/or hemicellulase, a mixture thereof. In some embodiments, the enzyme is thermophilic or hyperthermophilic. In some embodiments, the enzyme is any enzyme taught in U.S. Pat. Nos. 9,322,042; 9,376,728; 9,624,482; 9,725,749; 9,803,182; and 9,862,982; and PCT International Patent Application Nos. PCT/US2015/000320, PCT/US2016/063198, PCT/US2017/036438, PCT/US2010/032320, and PCT/US2012/036007 (all of which are incorporated in their entireties by reference).

Microbe

In some embodiments, the microbe is any prokaryotic or eukaryotic cell, with any genetic modifications, taught in U.S. Pat. Nos. 7,985,567; 8,420,833; 8,852,902; 9,109,175; 9,200,298; 9,334,514; 9,376,691; 9,382,553; 9,631,210; 9,951,345; and 10,167,488; and PCT International Patent Application Nos. PCT/US14/48293, PCT/US2018/049609, PCT/US2017/036168, PCT/US2018/029668, PCT/US2008/068833, PCT/US2008/068756, PCT/US2008/068831, PCT/US2009/042132, PCT/US2010/033299, PCT/US2011/053787, PCT/US2011/058660, PCT/US2011/059784, PCT/US2011/061900, PCT/US2012/031025, and PCT/US2013/074214 (all of which are incorporated in their entireties by reference).

Generally, although not necessarily, the microbe is a yeast or a bacterium. In some embodiments, the microbe is *Rhodosporidium toruloides* or *Pseudomonas putida*. In some embodiments, the microbe is a Gram negative bacterium. In some embodiments, the microbe is of the phylum Proteobactera. In some embodiments, the microbe is of the class Gammaproteobacteria. In some embodiments, the microbe is of the order Enterobacteriales. In some embodiments, the microbe is of the family Enterobacteriaceae. Examples of suitable bacteria include, without limitation, those species assigned to the *Escherichia, Enterobacter, Azotobacter, Erwinia, Bacillus, Pseudomonas, Klebsielia, Proteus, Salmonella, Serratia, Shigella, Rhizobia, Vitreoscilla*, and *Paracoccus* taxonomical classes. Suitable eukaryotic microbes include, but are not limited to, fungal cells. Suitable fungal cells are yeast cells, such as yeast cells of the *Saccharomyces* genus.

Yeasts suitable for the invention include, but are not limited to, *Yarrowia, Candida, Bebaromyces, Saccharomyces, Schizosaccharomyces* and *Pichia* cells. In some embodiments, the yeast is *Saccharomyces cerevisae*. In some embodiments, the yeast is a species of *Candida*, including but not limited to *C. tropicalis, C. maltosa, C. apicola, C. paratropicalis, C. albicans, C. cloacae, C. guillermondii, C. intermedia, C. lipolytica*, C. panapsilosis and C. zeylenoides. In some embodiments, the yeast is *Candida tropicalis*. In some embodiments, the yeast is a non-oleaginous yeast. In some embodiments, the non-oleaginous yeast is a *Saccharomyces* species. In some embodiments, the *Saccharomyces* species is *Saccharomyces cerevisiae*. In some embodiments, the yeast is an oleaginous yeast. In some embodiments, the oleaginous yeast is a *Rhodosporidium* species. In some embodiments, the *Rhodosporidium* species is *Rhodosporidium toruloides*.

In some embodiments the microbe is a bacterium. Bacterial host cells suitable for the invention include, but are not limited to, *Escherichia, Corynebacterium, Pseudomonas, Streptomyces*, and *Bacillus*. In some embodiments, the *Escherichia* cell is an *E. coli, E. albertii, E. fergusonii, E. hermanii, E. marmotae*, or *E. vulneris*. In some embodiments, the *Corynebacterium* cell is *Corynebacterium glutamicum, Corynebacterium kroppenstedtii, Corynebacterium alimapuense, Corynebacterium amycolatum, Corynebacterium diphtheriae, Corynebacterium efficiens, Corynebacterium jeikeium, Corynebacterium macginleyi, Corynebacterium matruchotii, Corynebacterium minutissimum, Corynebacterium renale, Corynebacterium striatum, Corynebacterium ulcerans, Corynebacterium urealyticum*, or *Corynebacterium* uropygiale. In some embodiments, the *Pseudomonas* cell is a *P. putida, P. aeruginosa, P. chlororaphis, P. fluorescens, P. pertucinogena, P. stutzeri, P. syringae, P. cremoricolorata, P. entomophila, P. fulva, P. monteilii, P. mosselii, P. oryzihabitans, P. parafluva*, or *P. plecoglossicida*. In some embodiments, the *Streptomyces* cell is a *S. coelicolor, S. lividans, S. venezuelae, S. ambofaciens, S. avermitilis, S. albus*, or *S. scabies*. In some embodiments, the *Bacillus* cell is a *B. subtilis, B. megaterium, B. licheniformis, B. anthracis, B. amyloliquefaciens*, or *B. pumilus*.

Biofuel

In some embodiments, the biofuel produced is ethanol, or any other organic molecule, described produced in a cell taught in U.S. Pat. Nos. 7,985,567; 8,420,833; 8,852,902; 9,109,175; 9,200,298; 9,334,514; 9,376,691; 9,382,553; 9,631,210; 9,951,345; and 10,167,488; and PCT International Patent Application Nos. PCT/US14/48293, PCT/US2018/049609, PCT/US2017/036168, PCT/US2018/029668, PCT/US2008/068833, PCT/US2008/068756, PCT/US2008/068831, PCT/US2009/042132, PCT/US2010/033299, PCT/US2011/053787, PCT/US2011/058660, PCT/US2011/059784, PCT/US2011/061900, PCT/US2012/031025, and PCT/US2013/074214 (all of which are incorporated in their entireties by reference).

Biomass

The biomass can be obtained from one or more feedstock, such as softwood feedstock, hardwood feedstock, grass feedstock, and/or agricultural feedstock, or a mixture thereof. In some embodiments, the biomass is a lignocellulosic biomass comprising cellulose, hemicellulose, and lignin in various ratios (depending on the biomass source). The cellulose, hemicellulose, and lignin are held together by covalent and strong hydrogen bonds forming a complex matrix recalcitrant to facile depolymerization.

Softwood feedstocks include, but are not limited to, *Araucaria* (e.g. *A. cunninghamii, A. angustifolia, A. araucana*); softwood Cedar (e.g. *Juniperus virginiana, Thuja plicata, Thuja occidentalis, Chamaecyparis thyoides Callitropsis nootkatensis*); Cypress (e.g. *Chamaecyparis, Cupressus Taxodium, Cupressus arizonica, Taxodium distichum, Chamaecyparis obtusa, Chamaecyparis lawsoniana, Cupressus* sempviren); Rocky Mountain Douglas fir; European Yew; Fir (e.g. *Abies balsamea, Abies alba, Abies procera, Abies amabilis*); Hemlock (e.g. *Tsuga canadensis, Tsuga mertensiana, Tsuga heterophylla*); Kauri; Kaya; Larch (e.g. *Larix decidua, Larix kaempferi, Larix laricina, Larix occidentalis*); Pine (e.g. *Pinus nigra, Pinus banksiana, Pinus contorta, Pinus radiata, Pinus ponderosa, Pinus resinosa, Pinus sylvestris, Pinus strobus, Pinus monticola, Pinus lambertiana, Pinus taeda, Pinus palustris, Pinus rigida, Pinus echinata*); Redwood; *Rimu*; Spruce (e.g. *Picea abies, Picea mariana, Picea rubens, Picea sitchensis, Picea glauca*); Sugi; and combinations/hybrids thereof.

For example, softwood feedstocks which may be used herein include cedar; fir; pine; spruce; and combinations thereof. The softwood feedstocks for the present invention may be selected from loblolly pine (*Pinus taeda*), radiata pine, jack pine, spruce (e.g., white, interior, black), Douglas fir, *Pinus silvestris, Picea abies*, and combinations/hybrids thereof. The softwood feedstocks for the present invention may be selected from pine (e.g. *Pinus radiata, Pinus taeda*); spruce; and combinations/hybrids thereof.

Hardwood feedstocks include, but are not limited to, *Acacia; Afzelia; Synsepalum* duloificum; *Albizia*; Alder (e.g. *Alnus glutinosa, Alnus rubra*); Applewood; *Arbutus*; Ash (e.g. *F. nigra, F. quadrangulata, F. excelsior, F. pennsylvanica lanceolata, F. latifolia, F. profunda, F. americana*); Aspen (e.g. *P. grandidentata, P. tremula, P. tremuloides*); Australian Red Cedar (*Toona ciliata*); Ayna (*Distemonanthus benthamianus*); Balsa (*Ochroma pyramidale*); Basswood (e.g. *T. americana, T. heterophylla*); Beech (e.g. *F. sylvatica, F. grandifolia*); Birch; (e.g. *Betula populifolia, B. nigra, B. papyrifera, B. lenta, B. alleghaniensis/B. lutea, B. pendula, B. pubescens*); Blackbean; Blackwood; Bocote; Boxelder; Boxwood; Brazilwood; Bubing a; Buckeye (e.g. *Aesculus hippocastanum, Aesculus glabra, Aesculus flava/Aesculus octandra*); Butternut; *Catalpa*; Chemy (e.g. *Prunus serotina, Prunus pennsylvanica, Prunus avium*); Crabwood; Chestnut; Coachwood; Cocobolo; Corkwood; Cottonwood (e.g. *Populus balsamifera, Populus deltoides, Populus sargentii, Populus heterophylla*); Cucumbertree; Dogwood (e.g. *Cornus florida, Cornus nuttallii*); Ebony (e.g. *Diospyros kurzii, Diospyros melanida, Diospyros crassiflora*); Elm (e.g. *Ulmus americana, Ulmus procera, Ulmus thomasii, Ulmus rubra, Ulmus glabra*); *Eucalyptus*; Greenheart; Grenadilla; Gum (e.g. *Nyssa sylvatica, Eucalyptus globulus, Liquidambar styraciflua, Nyssa aquatica*); Hickory (e.g. *Carya alba, Carya glabra, Carya ovata, Carya laciniosa*); Hornbeam; Hophornbeam; *Ipe; Iroko*; Ironwood (e.g. Bangkirai, *Carpinus caroliniana, Casuarina equisetifolia*, Choricbangarpia *subargentea, Copaifera* spp., *Eusideroxylon zwageri*, Guajacum *officinale*, Guajacum *sanctum*, Hopea *odorata, Ipe*, Krugiodendronferreum, *Lyonothamnus lyonii* (*L. floribundus*), *Mesua ferrea, Olea* spp., *Olneya tesota, Ostrya virginiana, Parrotia persica, Tabebuia serratifolia*); Jacaranda; Jotoba; Lacewood; *Laurel; Limba; Lignum vitae*; Locust (e.g. *Robinia pseudacacia, Gleditsia triacanthos*); Mahogany; Maple (e.g. *Acer saccharum, Acer nigrum, Acer negundo, Acer rubrum, Acer saccharinum, Acer pseudoplatanus*); Meranti; Mpingo; Oak (e.g. *Quercus macrocarpa, Quercus alba, Quercus stellata, Quercus bicolor, Quercus virginiana, Quercus michauxii, Quercus prinus, Quercus muhlenbergii, Quercus chrysolepis, Quercus lyrata, Quercus robur, Quercus petraea, Quercus rubra, Quercus velutina, Quercus laurifolia, Quercus falcata, Quercus nigra, Quercus phellos, Quercus texana*); Obeche; Okoumé; Oregon Myrtle; California Bay *Laurel*; Pear; Poplar (e.g. *P. balsamifera, P. nigra*, Hybrid Poplar (Populusxcanadensis)); Ramin; Red cedar; Rosewood; Sal; Sandalwood; *Sassafras*; Satinwood; Silky Oak; Silver Wattle; Snakewood; Sourwood; Spanish cedar; American sycamore; Teak; Walnut (e.g. *Juglans nigra, Juglans regia*); Willow (e.g. *Salix nigra, Salix alba*); Yellow poplar (*Liriodendron tulipifera*); Bamboo; Palmwood; and combinations/hybrids thereof.

For example, hardwood feedstocks for the present invention may be selected from *Acacia*, Aspen, Beech, *Eucalyptus*, Maple, Birch, Gum, Oak, Poplar, and combinations/hybrids thereof. The hardwood feedstocks for the present invention may be selected from *Populus* spp. (e.g. *Populus tremuloides*), *Eucalyptus* spp. (e.g. *Eucalyptus globulus*), *Acacia* spp. (e.g. *Acacia dealbata*), and combinations thereof.

Grass feedstocks include, but are not limited to, $C_4$ or $C_3$ grasses, e.g. Switchgrass, Indiangrass, Big Bluestem, Little Bluestem, Canada Wildrye, Virginia Wildrye, and Goldenrod wildflowers, etc, amongst other species known in the art.

Agricultural feedstocks include, but are not limited to, agricultural byproducts such as husks, stovers, foliage, and the like. Such agricultural byproducts can be derived from crops for human consumption, animal consumption, or other non-consumption purposes. Such crops can be corps such as corn, wheat, sorghum, rice, soybeans, hay, potatoes, cotton, or sugarcane. The feedstock can arise from the harvesting of crops from the following practices: intercropping, mixed intercropping, row cropping, relay cropping, and the like.

In some embodiments, the biomass is an ensiled biomass. In some embodiment, the biomass is ensiled by placing the biomass in an enclosed container or room, such as a silo, or by piling it in a heap covered by an airproof layer, such as a plastic film. The biomass undergoing the ensiling, known as the silage, goes through a bacterial fermentation process resulting in production of volatile fatty acids. In some embodiment, the ensiling comprises adding ensiling agents such as sugars, lactic acid or inoculants. In some embodiments, the ensiled biomass comprises one or more toxic compounds. In some embodiments, when ensiled biomass comprises one or more toxic compounds, the microbe is resistant to the one or more toxic compounds.

EXAMPLE 1

Method Section:
mDES Synthesis mDES is prepared by mixing ethylene glycol or glycerol and zinc chloride in a molar ratio of 4:1, followed by heating the mixture with constant stirring at 110±2° C. for 2 h in an oil bath until a transparent solution is achieved.

mDES is prepared by mixing choline chloride and metal phosphate in various molar ratios, followed by heating the mixture with constant stirring at 120±2° C. for 16 h in an oil bath.

3 component mDES is prepared by mixing choline chloride, polyol/phenol and metal phosphate in various molar ratios, followed by heating the mixture with constant stirring at 120±2° C. for 16 h in an oil bath.

Biomass Pretreatment (Washing Method)

All pretreatment reactions were conducted in duplicate. 2 mm biomass and mDESs were mixed in a various ratio (w/w) to afford a biomass loading of 10-50 wt % in a 15 mL capped glass pressure tube and pretreated for 0.5-5 h in an oil bath heated at 100-160° C. After pretreatment, samples were removed from the oil bath and allowed to cool. 10 mL ethanol (or water) was slowly added to the slurry and mixed well. The mixture was transferred to 50 mL Falcon tubes and centrifuged at high speed (4000 rpm) to separate solids and remove any residual mDESs. Recovered solid is further washed with a mixture of ethanol and water (1:1) to remove residual mDES and freeze-dried for further analysis.

Pretreatment Optimization

Pretreatment of 10-50% (w/w) slurry is prepared by mixing 1-5 g of biomass with 9-5 g of mDES in a 25 mL glass tube reactor. Followed by heating the tube reactors in an oil bath at 100-160±2° C. for 0.5-5 h. Post pretreatment, 25 mL of ethanol (or water) are added to the slurry before being transferred to 50 ml Falcon tubes and centrifuged at 4500 rpm to separate solids form liquid. Recovered solid is further washed with a mixture of ethanol and water (1:1) to remove residual mDES and freeze-dried for further analysis. A central composite design (CCD; table 1) is used to optimize the effect of temperature (° C.), time (h) and solid loading (%) on glucose and xylose release, lignin removal, and solid recovered using JMP Pro 14 (SAS Institute, Inc., Cary, N.C.). Low and high levels of the independent variable is coded as −1 and +1 and axial points are located at (±α, 0, 0), (0, ±α, 0) and (0, 0, ±α) where a is the distance of the axial point and makes the design rotatable. In this study, α value is fixed at 1.682 (rotatable). The experimental sequence is randomized to minimize the effects of uncontrolled errors. The response variable glucose ($Y_1$), xylose ($Y_2$), lignin yield ($Y_3$), and Solid recovered ($Y_4$), are used to develop an empirical model using the three independent variables via a second-degree polynomial equation as given below:

$$\hat{Y} = \beta_0 + \sum_{i}^{n} \beta_i x_i + \sum_{ii}^{n} \beta_{ii} x_i^2 + \sum_{i=1}^{n-1} \sum_{j=i+1}^{n} \beta_{ij} x_i x_j$$

Where $\hat{Y}$ is the predicted response, $\beta_0$ the constant coefficient, $\beta_i$ the linear coefficients, $\beta_{ij}$ the interaction coefficients, $\beta_{ii}$ the quadratic coefficients and $x_i$, $x_j$ are the coded independent variables. All the experiments are performed in duplicates.

Enzymatic Hydrolysis

Enzymatic hydrolysis of the untreated and pretreated sorghum biomass is carried out by following the NREL laboratory analytical procedure (Selig et al., 2008). The cellulase (CTec3, Novozymes Inc.) and hemicellulose (HTec3, Novozymes Inc.) enzymes are premixed at a 9:1 v/v ratio. The saccharification is performed at 50° C. for 72 h at an enzyme loading of 10 mg enzyme protein/g starting biomass at 48 rpm in a rotary incubator (Enviro-Genie, Scientific Industries, Inc.). After hydrolysis, liquid samples are collected and centrifuged at 12,000 rpm for 2 minutes and the supernatant is filtered using 0.45 μm centrifuge filters before performing sugar analysis. Monomeric sugars (glucose and xylose) are determined by HPLC using an Agilent 1200 series instrument equipped with a refractive index detector and Bio-Rad Aminex HPX-87H column, coupled with a guard column assembly. Product separation is obtained at 60° C. with 4 mM $H_2SO_4$ as mobile phase at a flow rate of 0.6 mL/min.

Analytical Methods

Compositional analysis of the untreated and pretreated sorghum is performed to determine the glucan, xylan, and klason lignin following the two-step acid hydrolysis procedure described by NREL. In summary, 300 mg of the dry biomass is exposed to 72% w/w $H_2SO_4$ at 30° C. for 1 hour, followed by secondary hydrolysis at 4% w/w $H_2SO_4$ at 121° C. for 1 hour. After the two-step acid hydrolysis, acid-insoluble lignin is obtained by filtering the hydrolysates through filter crucibles. Monomeric sugars (glucose and xylose) are determined by HPLC, as described above. Mason lignin is determined by subtracting the weight of air-dried residual solids and the ash content.

Molecular weight analysis of the pretreated biomass and ethanol wash were analyzed using gel permeation chromatography equipped with UV and RI detectors and a PLgel mixed column coupled with a guard column assembly. Product separation is obtained at 40° C. with tetrahydrofuran as mobile phase at a flow rate of 1.0 mL/min.

ATR FT-IR spectra are obtained from untreated, pretreated, and CEL samples between 4000 $cm^{-1}$ and 800 $cm^{-1}$ with 64 scans and a resolution of 4 $cm^{-1}$ on a Bruker spectrometer VERTEX 70 with reflection ATR cell (Bruker Platinum diamond ATR) coupled with a room temperature HTS-XT detector, working a 10 KHz. Baseline correction and atmospheric compensation are corrected by OPUS 7.2 software algorithm.

Powder X-ray diffraction (XRD) measurements are performed on a PANalytical Empyrean system equipped with a PIXcel3D detector. The Bragg-Brentano geometry comprises a Cu X-ray tube (operated at 45 kV and 40 mA; λ=1.5418 Å), incident beam optics with a 1/8° fixed divergence, and a 1/4° antiscatter slit as well as a 0.04 rad soller slit and receiving optics which include another 0.04 rad soller slit, a Ni Kβ filter, and the PIXcel3D detector in scanning mode. A reflection-transmission spinner is used as a sample holder and the spinning rate is set at 8 rpm throughout the experiment. The patterns are collected in the 2θ range of 5–50° with a step size of 0.026° and an exposure time of 300 s.

Enzyme Inhibition

All enzymatic inhibition tests were conducted in duplicate. Enzymatic inhibition was carried out using commercially available enzymes, Cellic® Ctec3 from Novozymes on microcrystalline cellulose (MCC), at 50° C. in a rotary incubator (Enviro-Genie, Scientific Industries, Inc.). All reactions were performed at 5 wt % MCC loading and 0-5 wt % AlP in a 15 mL centrifuge tube. The pH of the mixture was adjusted to 5 with either HCl or NaOH. The total reaction volume included a total protein content of 10 mg per g MCC. The amount of sugars released was measured by HPLC as described previously.

Microbial Toxicity

Tryptic soy broth was mixed with 5 wt % (w/w) mDES and pH was adjusted to 7. The top fraction was collected, filtered and used to prepare dilutions with fresh media. Microbes were first cultivated in tubes containing 10 mL of tryptic soy broth from freshly streaked plates and incubated at 30° C. and 200 rpm for 24 hours. To start the experiment, 5 μL of the seed cultures were combined with 145 μL of the filtered hydrolysates or fresh tryptic soy broth as a control in a lidded 96-well plate and incubated at 30° C. with shaking using a DTX880 multiplate reader (Beckton-Coulter, USA). The optical density at 595 nm was measured each 5 minutes for 48 hours and used to obtain the average maximum cell biomass (the highest OD 595 nm value) and the average growth rate (the slope of growth curves during the exponential phase, after plotting the natural logarithm of OD values versus time) from each condition. The cultivations were performed by triplicate.

Result Section

Effect of mDES on sorghum biomass fractionation to fermentable sugar released is shown in FIG. 1. Enzymatic saccharification of untreated sorghum biomass resulted in 19.5% glucose and 17.3% of xylose yield. As a baseline, pretreatment with ethylene glycol and aqueous $ZnCl_2$ is evaluated to test the efficacy of mDES at temperature of 140° C., time 3 h, and solid loading of 10%. Result indicate that glucose yield of 59.1% and 68.8% are obtained for ethylene glycol and aqueous $ZnCl_2$, respectively. Similarly, a xylose yield of 32.5% and 69.8% are obtained for ethylene glycol and aqueous $ZnCl_2$, respectively. To improve the sugar yields sorghum biomass is pretreated with $EG:ZnCl_2$ and $glycerol:ZnCl_2$. Result show a glucose and xylose yield of 82.9% and 76.5%, respectively when treated with $glycerol:ZnCl_2$. Further increase of glucose (96.4%) and xylose (82.9%) yield are obtained when pretreated with $EG:ZnCl_2$. Clearly, $EG:ZnCl_2$ performed better than $glycerol:ZnCl_2$ in pretreating sorghum, further experiments are performed to optimize the efficacy of $EG:ZnCl_2$. To better understand the impact of individual components of $EG:ZnCl_2$. Central composite design is used to optimize glucose and xylose yield for the $EG:ZnCl_2$ pretreatment (FIGS. 2A, 2B, 2C, 3A, 3B, and 3C). Optimized glucose yield of 96.1% is obtained at temperature of 155° C., time 2.2 h, and solid loading of 20%, while an optimized xylose yield of 95.9% is obtained at temperature of 140° C., time 2.2 h, and solid loading of 20%.

FIGS. 4A, 4B, 4C, 5A, 5B, and 5C show the response surface plots for lignin removal and solid recovered after pretreatment of sorghum with $EG:ZnCl_2$. Under optimized conditions (glucose released) lignin removal yield and solid recovered yield is 35% and 60%, respectively.

Figure 6:
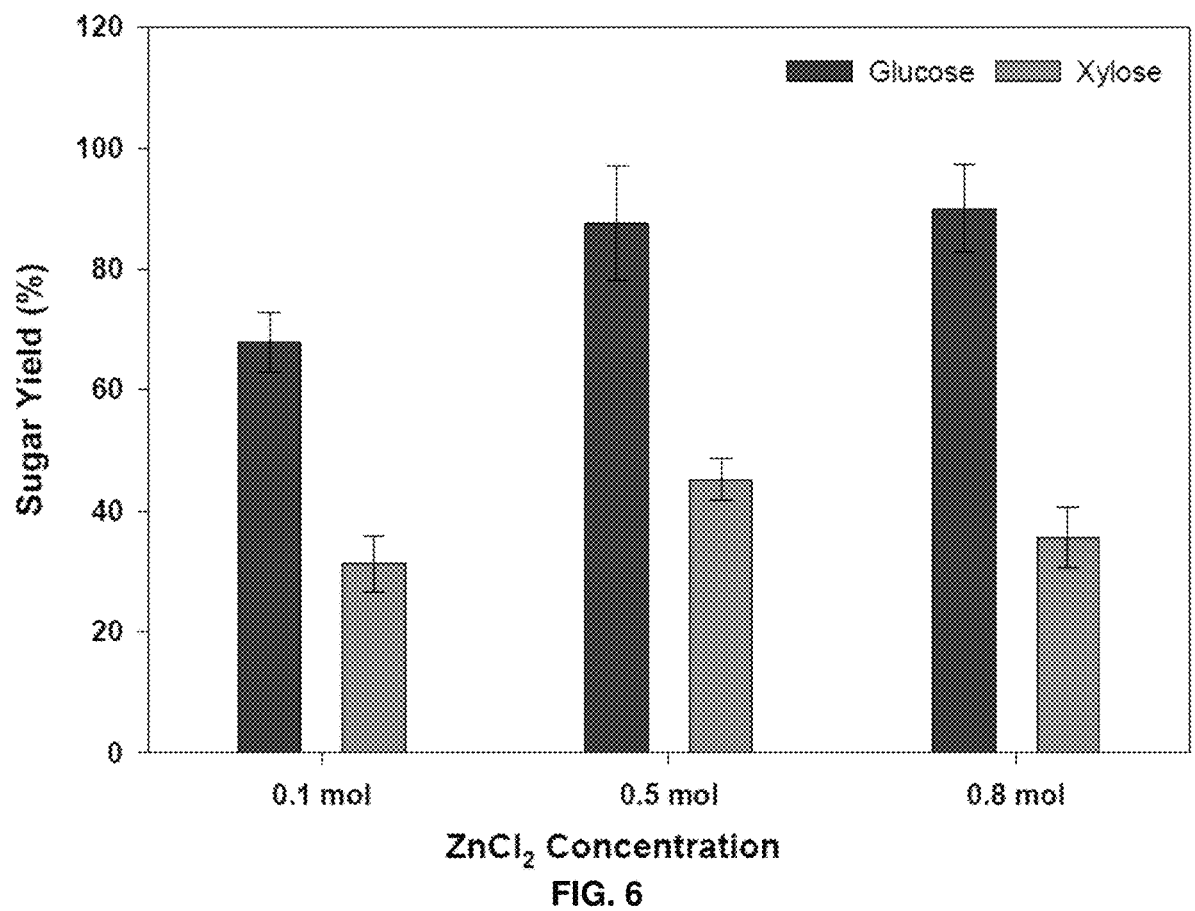
FIG. 6: Glucose and Xylose yield from different $ZnCl_2$ concentrations in mDES at temperature of 155° C., 2 h reaction time, and 20% solid loading.

Impact of $ZnCl_2$ concentration on sorghum pretreatment is investigated by synthesizing mDES with different molar ratio of $ZnCl_2$. FIG. 6 shows the decreasing $ZnCl_2$ concentration from 1 mole to 0.1 mole lead to the decrease in fermentable sugar release.

Figure 7:
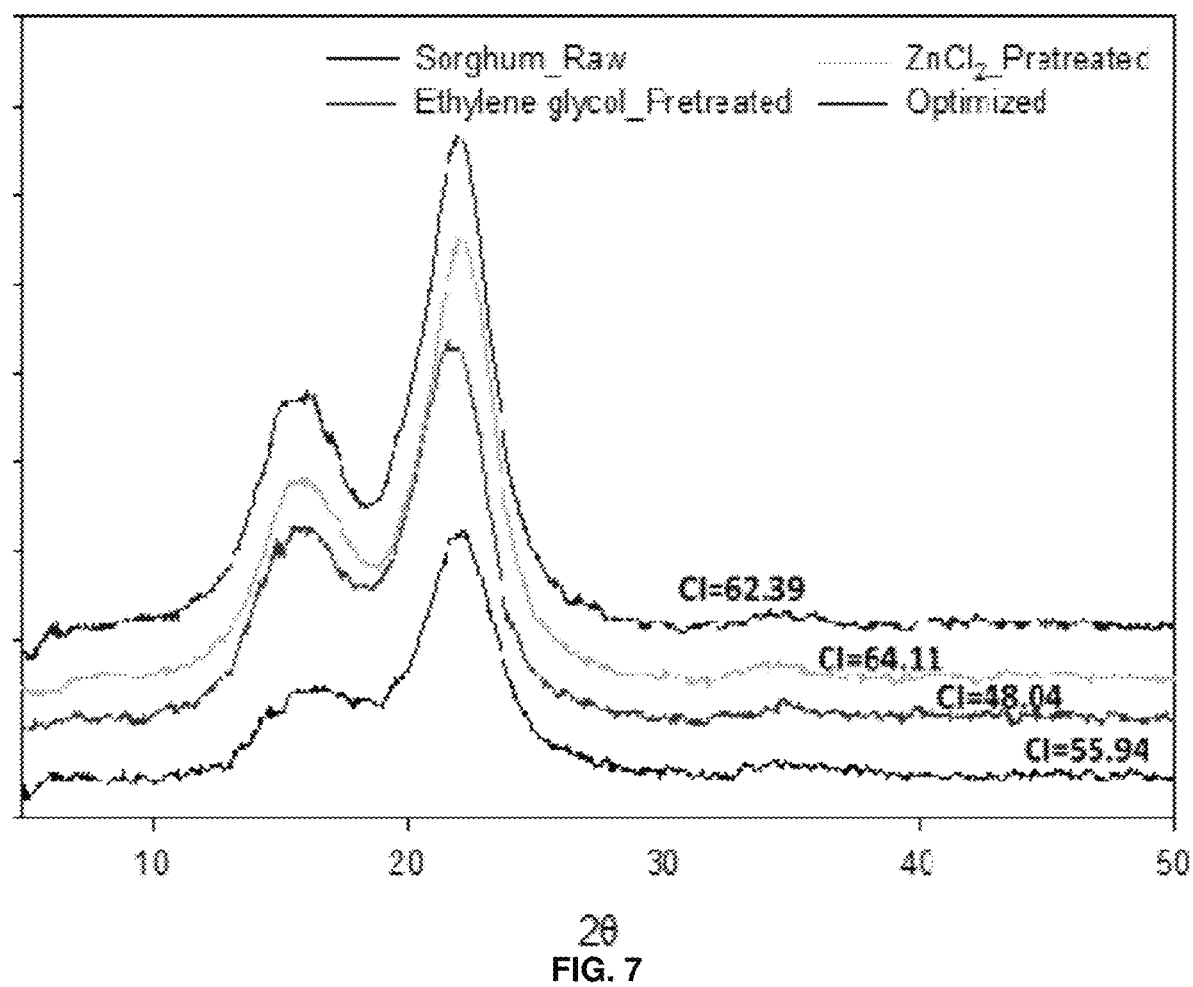
FIG. 7: X-ray powder diffraction (XRD) patterns of untreated and pretreated sorghum samples with their corresponding crystallinity index.
Figure 8:
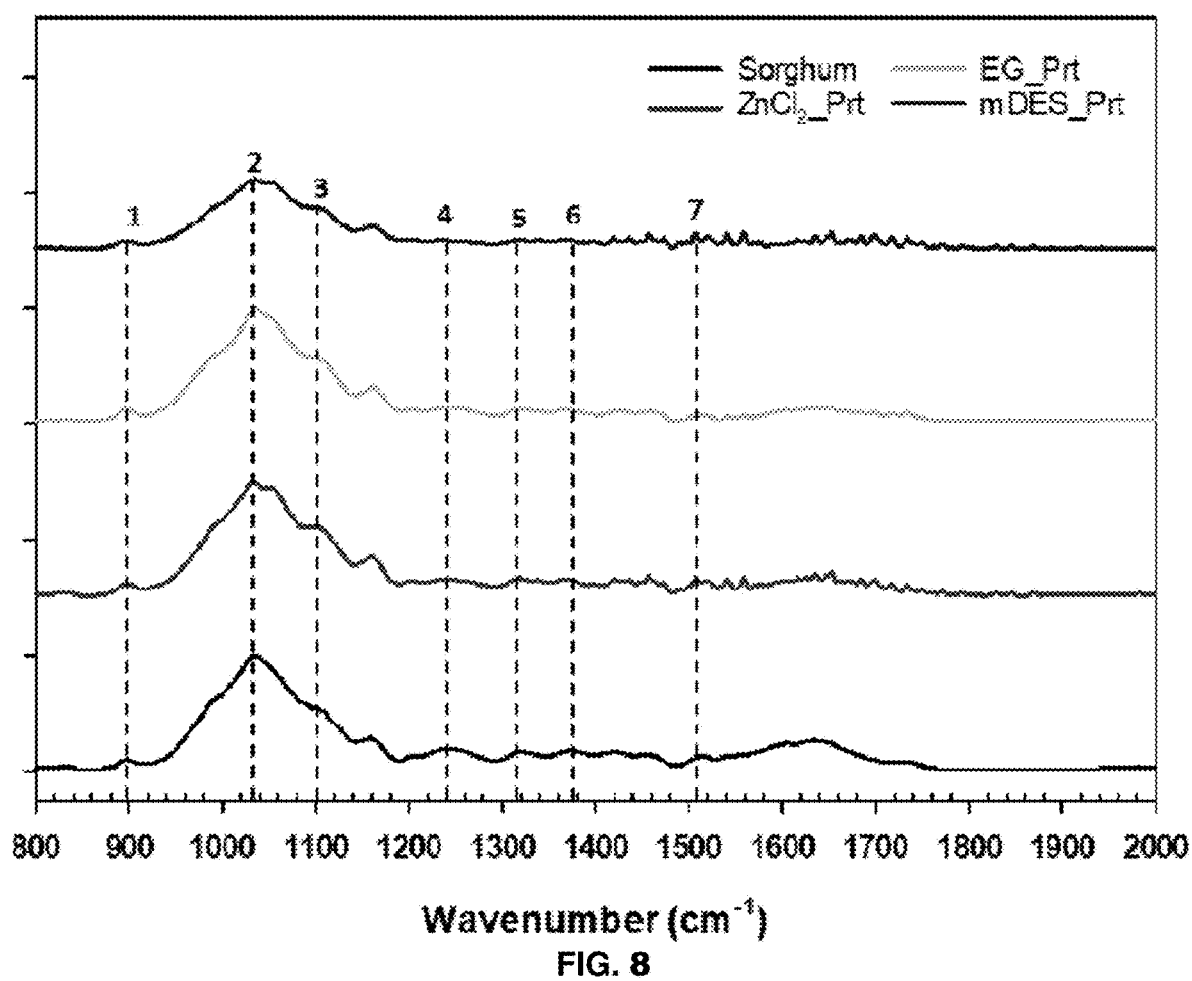
FIG. 8: FTIR spectra for untreated and pretreated sorghum.

XRD (FIG. 7) is used to measure the crystalline index, while FTIR (FIG. 8) is employed to investigate the structural changes and chemical variations of the different types of sorghum under different pretreatment methods.

Figure 9:
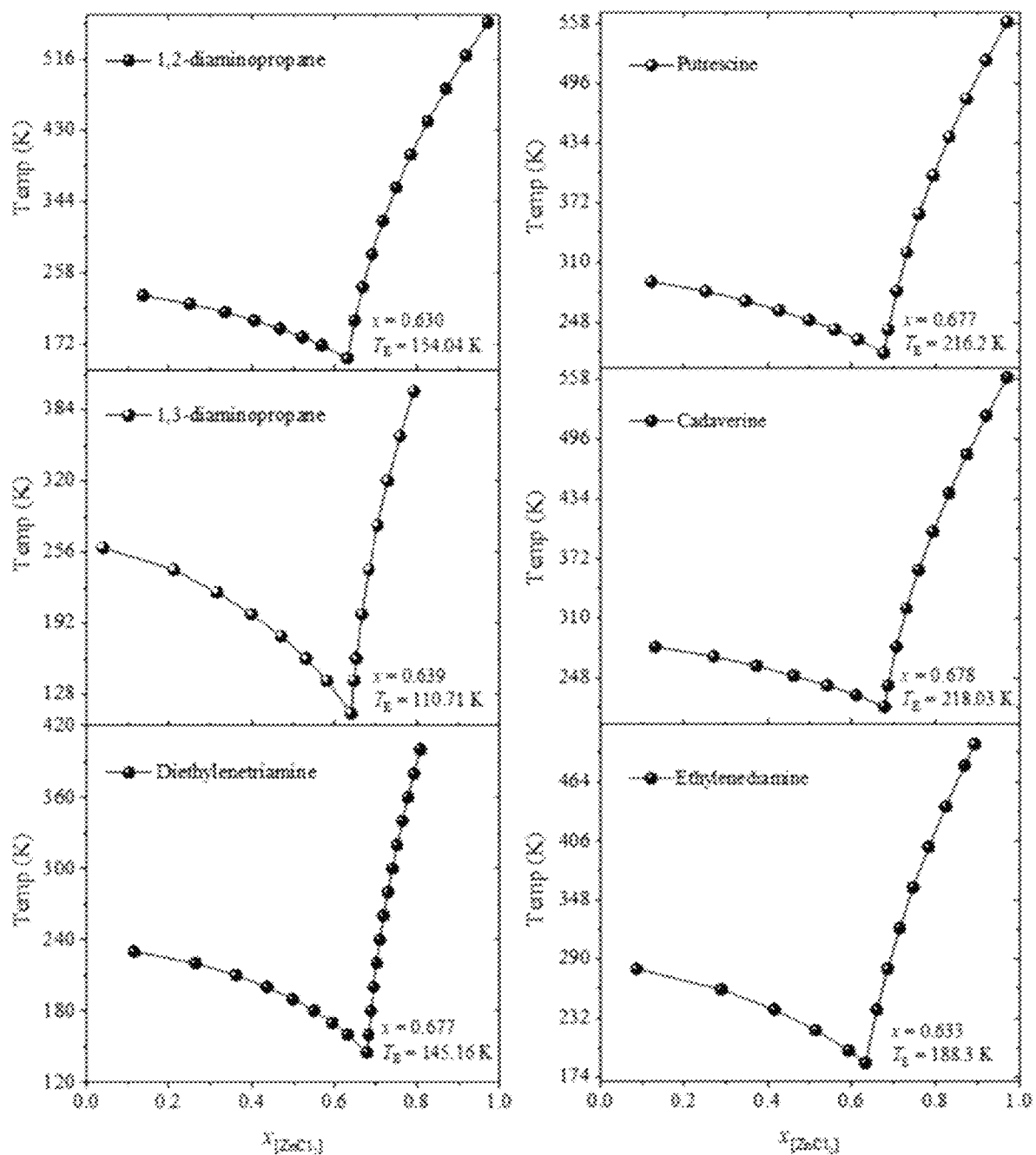
FIG. 9: COSMO-RS Predicted eutectic point composition of zinc chloride with different amines.
Figure 9:
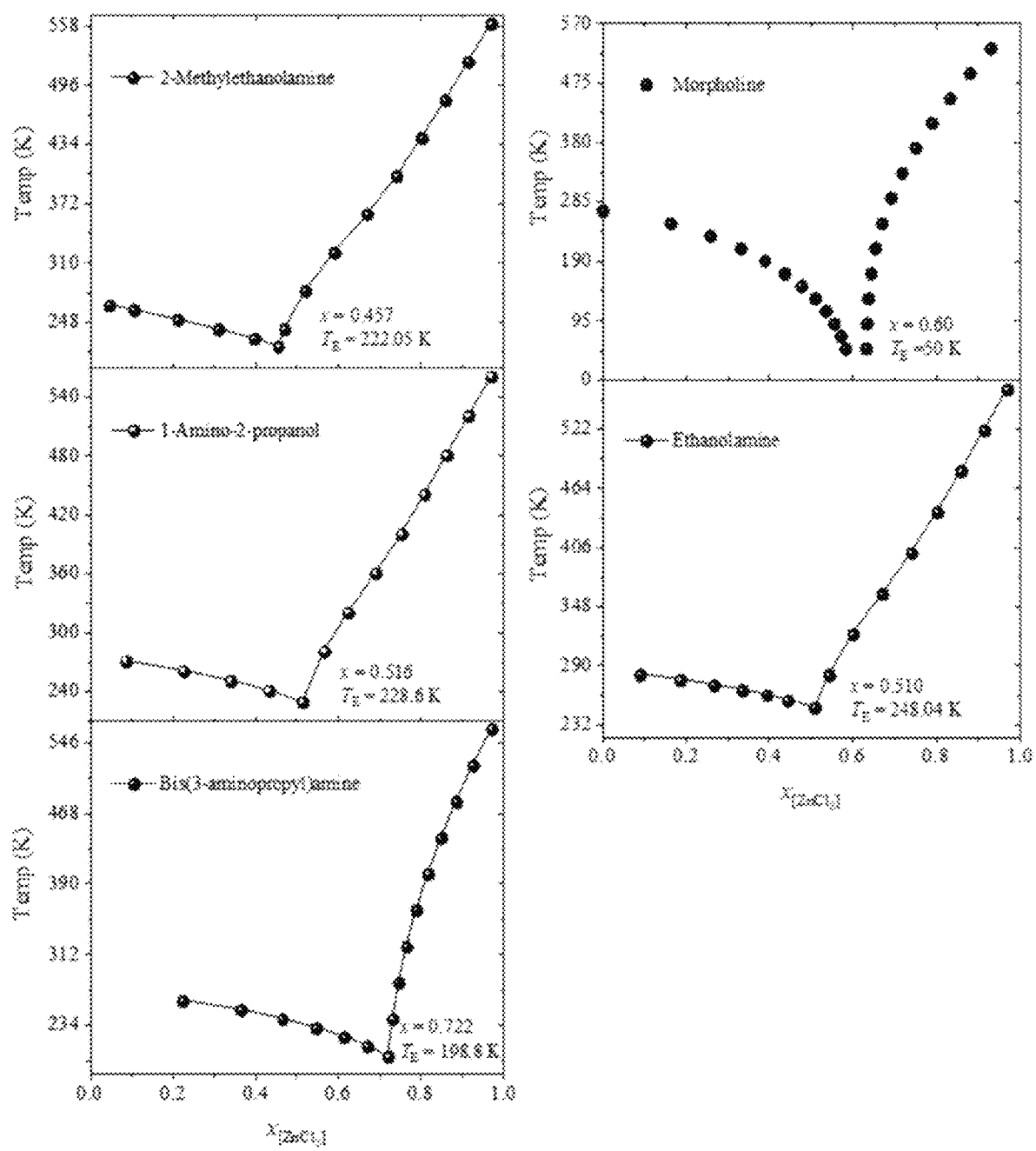
Figure 9:
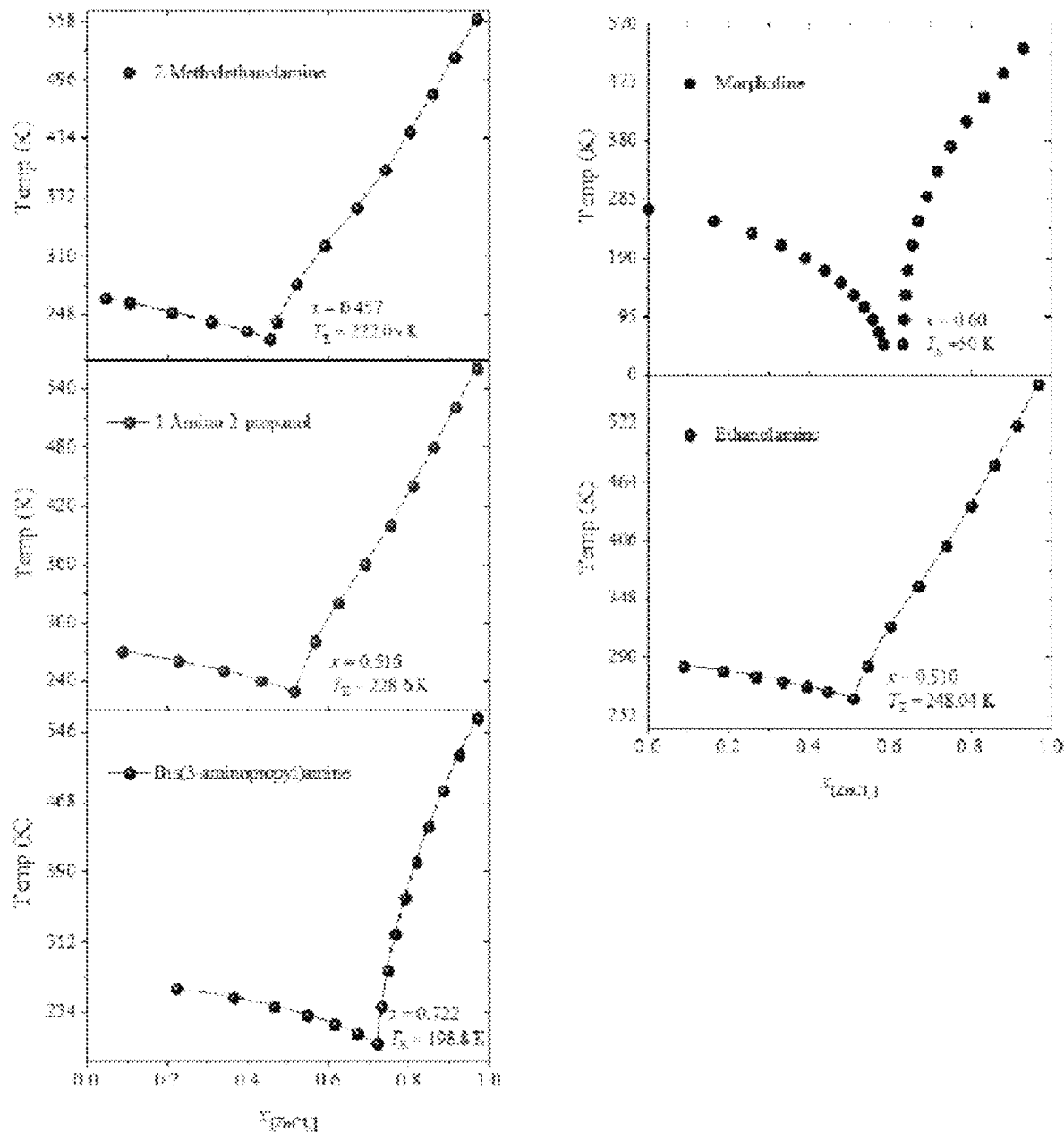

Besides $ZnCl_2$, most of the transition metal chlorides can be used to make DES. Mainly, $CuCl_2$, $FeCl_3$, $CoCl_2$, $NbCl_5$, $AlCl_3$, $NiCl_2$, and $CrCl_3$ are potential metal halides. mDES can also be made from amines. The eutectic points (FIG. 9) for different zinc chloride:amine based DESs has been predicted.

A central composite design of experiment (Table 1) is performed to optimize the reaction temperature. Effect of temperature on mDES pretreatment efficacy is tested in the range of 120-160° C.

TABLE 1

Experimental Design matrix.

| Factors | Code | Coded variable levels | | | | |
| --- | --- | --- | --- | --- | --- | --- |
| | | $-\alpha$ | $-1$ | 0 | 1 | $+\alpha$ |
| Temperature (° C.) | $X_1$ | 106.36 | 120 | 140 | 160 | 173.64 |
| Time (h) | $X_2$ | 0.32 | 1 | 2 | 3 | 3.68 |
| Solid loading (%) | $X_3$ | 3.18 | 10 | 20 | 30 | 36.82 |

Figure 10:
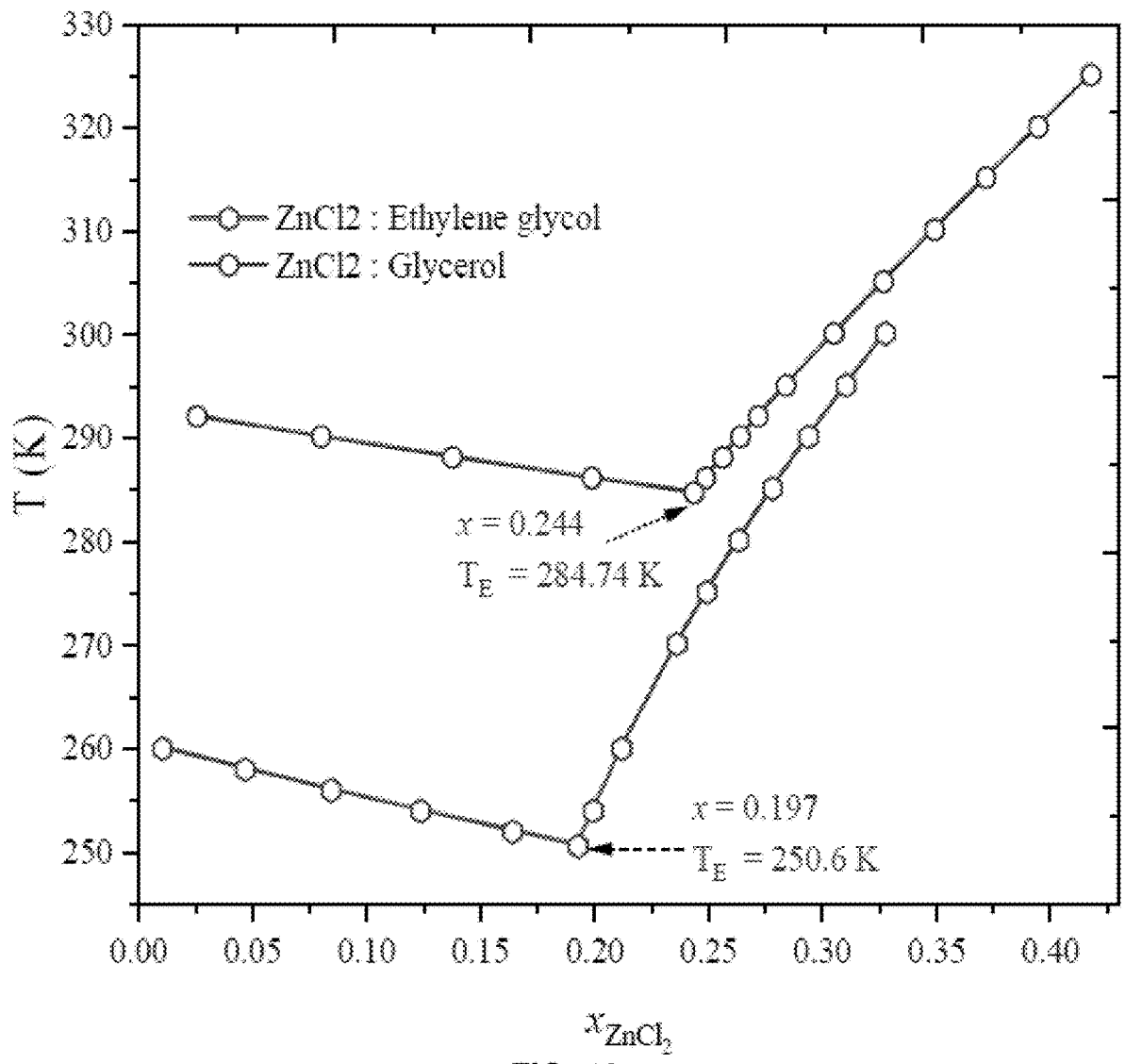
FIG. 10: COSMO-RS Predicted eutectic point composition of DES composed of zinc chloride with ethylene glycol and glycerol.

Molar ratio for $EG:ZnCl_2$ (4:1) and $glycerol:ZnCl_2$ (4:1) are same. Eutectic points for mDES is predicted using COSMO-RS model (FIG. 10), followed by experimental validation.

Pretreatment

Pretreatment of 10-50% (w/w) slurry (or 10-30% (w/w) slurry) is prepared by mixing 1-5 g of biomass (1-3 g of biomass) with 5-9 g of mDES (or 7-9 g of mDES) in a 25 mL glass tube reactor. Followed by heating the tube reactors in an oil bath at 100-160±2° C. (120-160±2° C.). Post pretreatment, 25 mL of ethanol (water, or a mixture of ethanol and water) are added to the slurry before being transferred to 50 ml Falcon tubes and centrifuged at 4500 rpm to separate solids form liquid. Recovered solid is further washed with a mixture of ethanol and water (1:1) to remove residual mDES and freeze-dried for further analysis.

Enzymatic Hydrolysis

Enzymatic hydrolysis of the untreated and pretreated sorghum biomass is carried out by following the NREL laboratory analytical procedure (Selig et al., 2008). The cellulase (CTec3, Novozymes Inc.) and hemicellulose (HTec3, Novozymes Inc.) enzymes are premixed at a 9:1 v/v ratio. The saccharification is performed at 50° C. for 72 h at an enzyme loading of 10 mg enzyme protein/g starting biomass at 48 rpm in a rotary incubator (Enviro-Genie, Scientific Industries, Inc.). After hydrolysis, liquid samples are collected and centrifuged at 12,000 rpm for 2 minutes and the supernatant is filtered using 0.45 μm centrifuge filters before performing sugar analysis.

Percentage Range of $ZnCl_2$ in mDES and Biomass

The optimum molar ratio of $EG:ZnCl_2$ to form a eutectic point is 4:1, which accounts for 20% $ZnCl_2$ in the mDES. However, it is demonstrated that mDES can be formed by varying the $ZnCl_2$ concentration from 0.1-1 moles (2.44-20%). Amount of $ZnCl_2$ with respect to biomass can vary form (2-16%). FIG. 6 shows the decreasing $ZnCl_2$ concentration from 1 mole to 0.1 mole lead to the decrease in fermentable sugar release.

Figure 11:
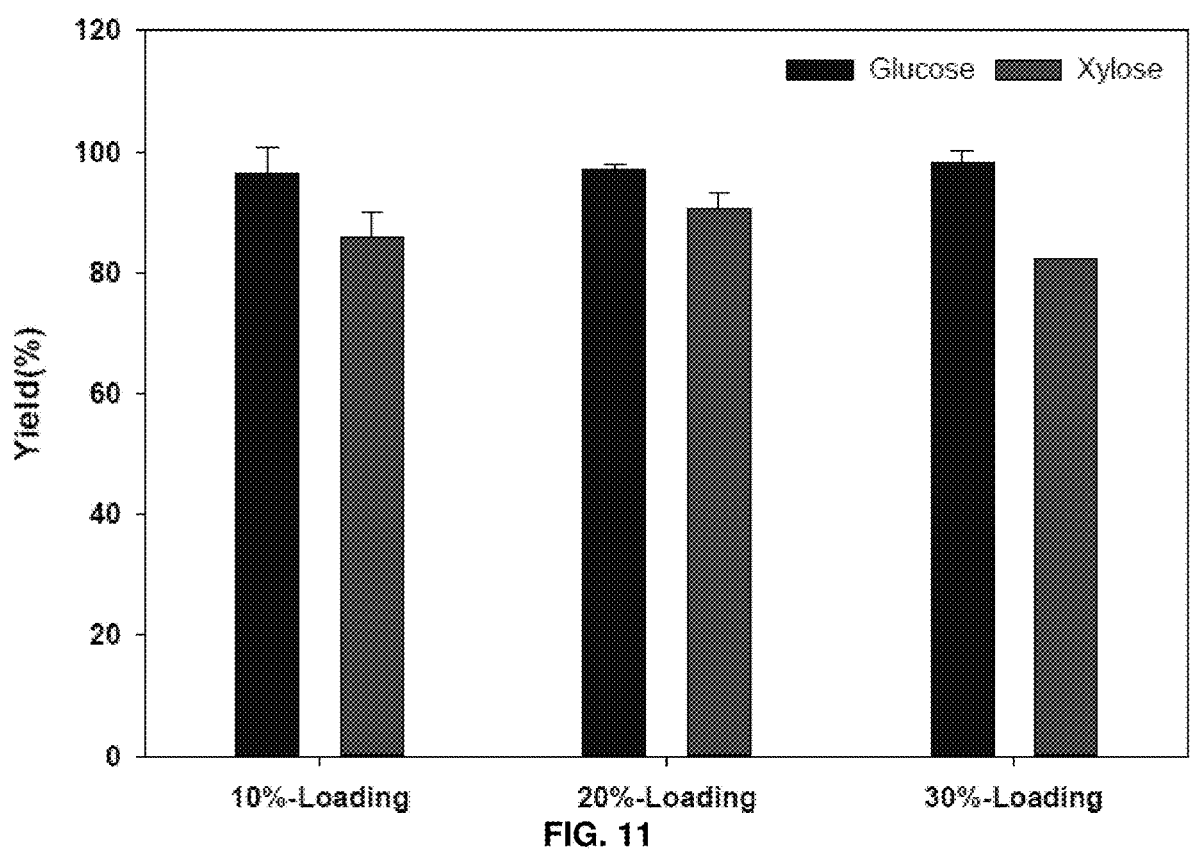
FIG. 11. Fermentable sugar yields using EG:$ZnCl_2$.
Figure 12:
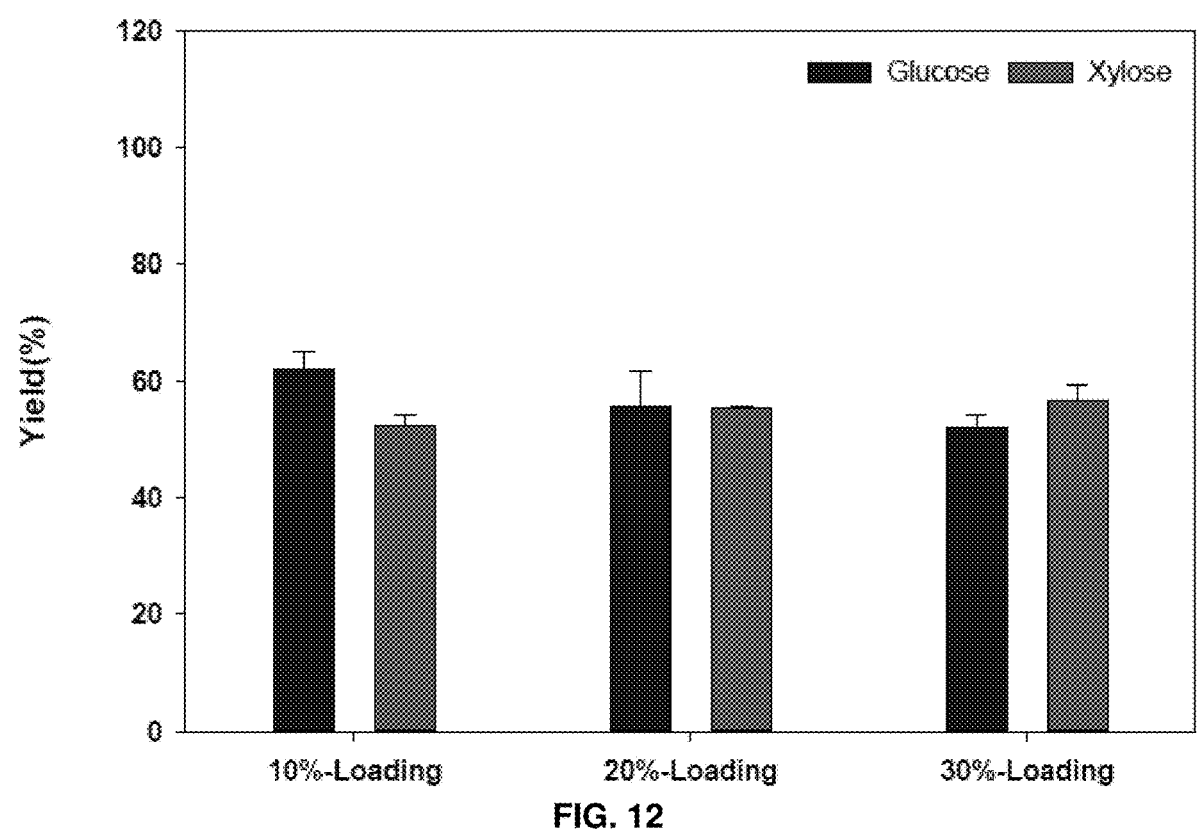
FIG. 12. Fermentable sugar yields using Glycerol:$ZnCl_2$.
Figure 13A:
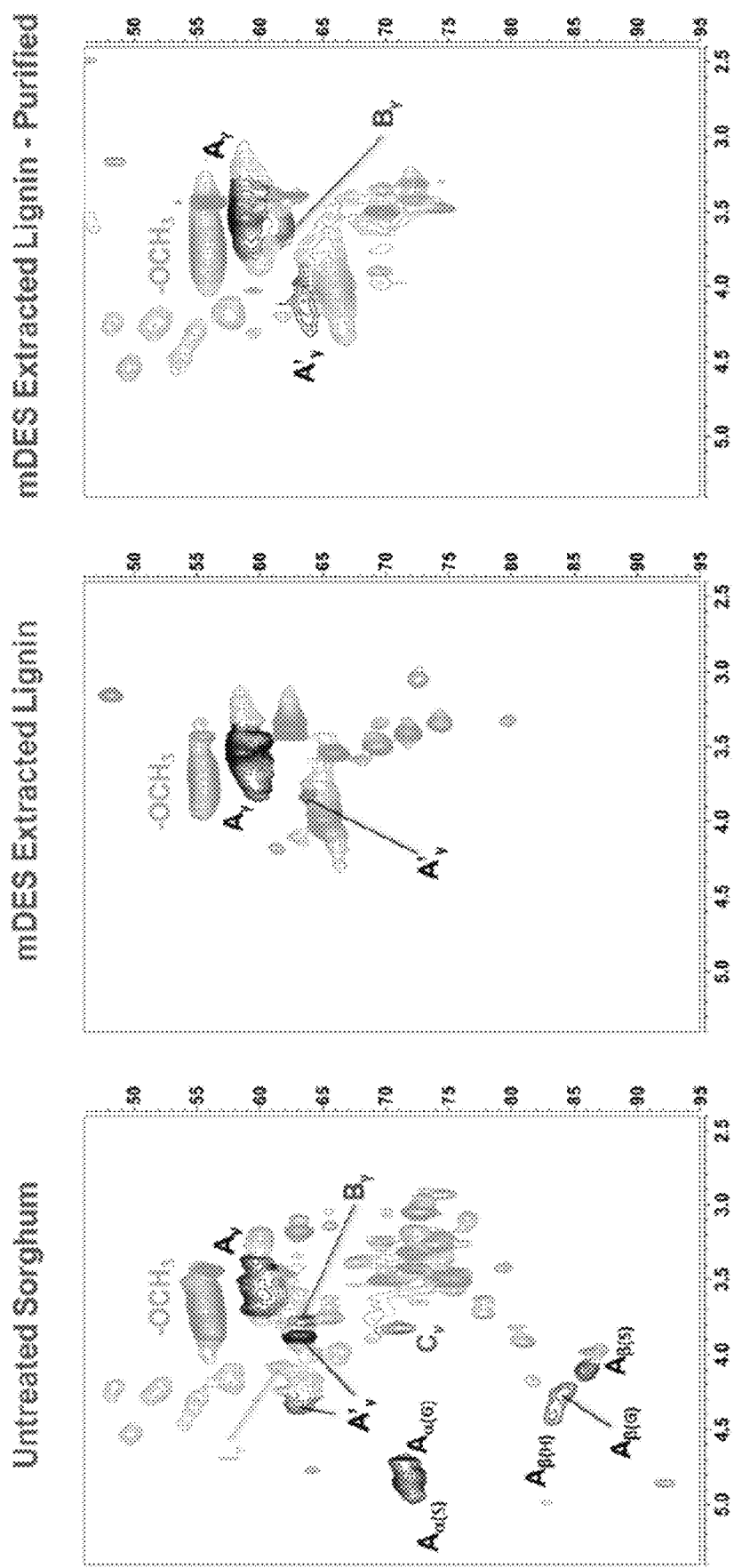
FIG. 13A. NMR for lignin obtained using $ZnCl_2$-EG mDES: Aliphatic region.
Figure 13B:
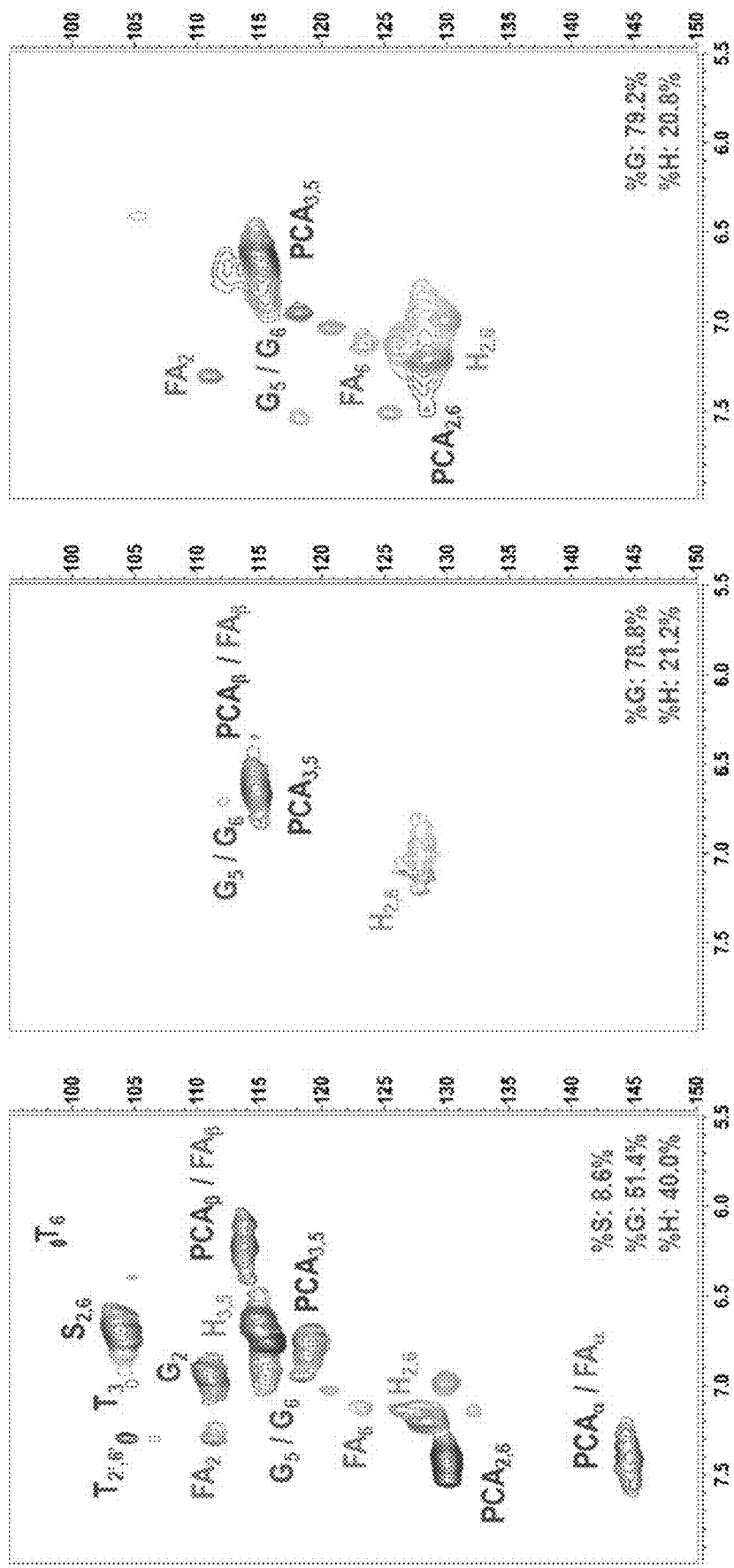
FIG. 13B. NMR for lignin obtained using $ZnCl_2$-EG mDES: Aromatic region.
Figure 13C:
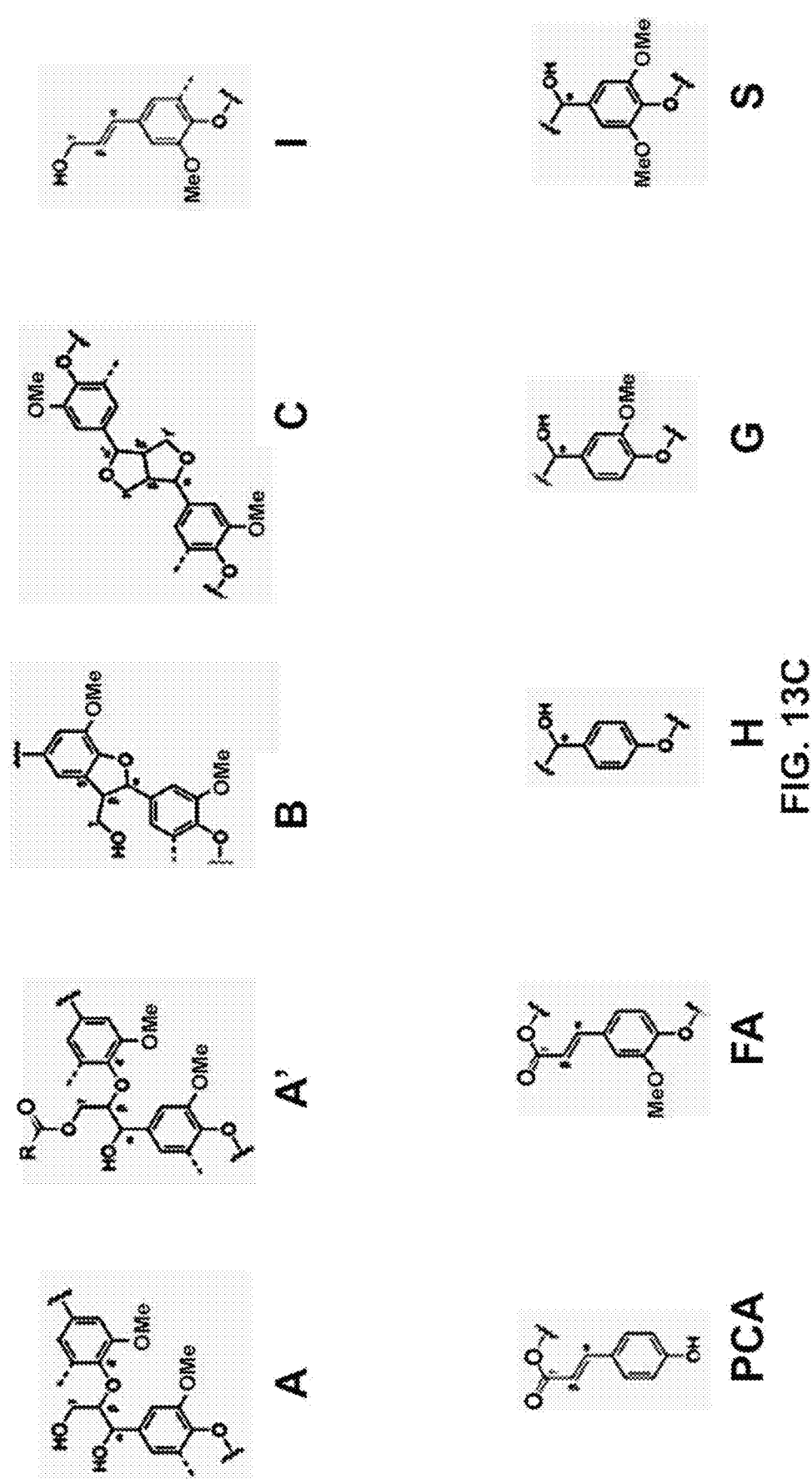
FIG. 13C. Structural unit assignment.
Figure 14:
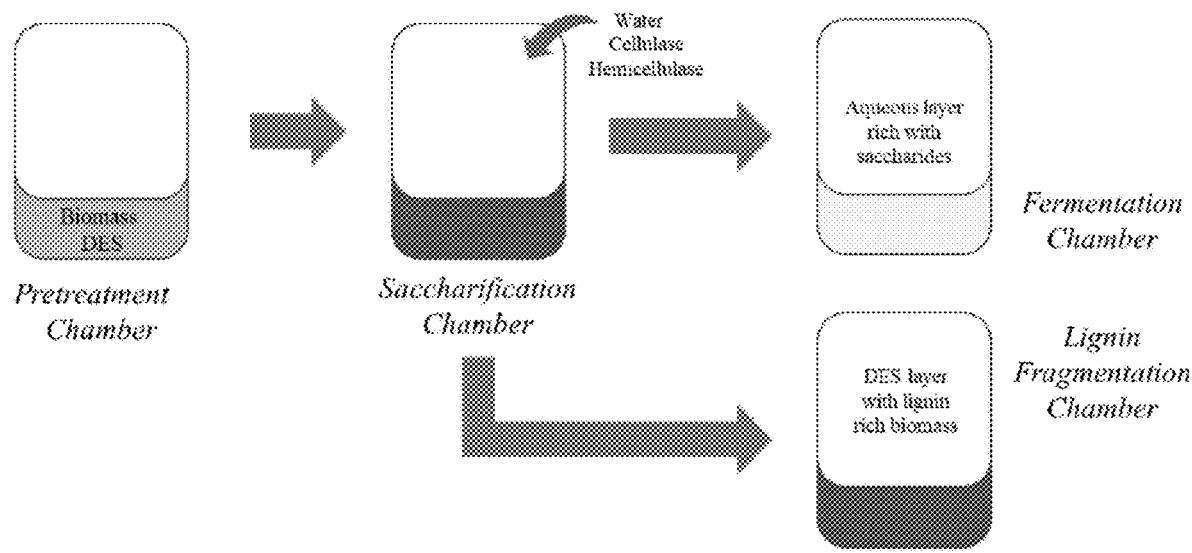
FIG. 14. mDES-based bio-refinery concept.

FIGS. 11 and 12 show the fermentable sugar yields using $EG:ZnCl_2$ or $glycerol:ZnCl_2$. The pretreatment for FIG. 11 comprises DES 30-10 wt %, 3 hours, about 140° C. After pretreatment, there is a solid/liquid separation and ethanol: water (1:1) washing. The enzymatic hydrolysis is at 2% solid, 0.05 M sodium citrate buffer (pH 5), CTec3Htec3 (20 mg protein/g glucan), at 50° C. for 72 hours. The pretreatment for FIG. 12 comprises DES 30-10 wt %, 3 hours, about 140° C. After pretreatment, there is a solid/liquid separation and ethanol:water (1:1) washing. The enzymatic hydrolysis is at 2% solid, 0.05 M sodium citrate buffer (pH 5), CTec3Htec3 (20 mg protein/g glucan), at 50° C. for 72 hours. FIGS. 13A to 13C show NMR for lignin obtained using $ZnCl_2$-EG mDES: Aliphatic region, Aromatic region, and structural unit assignment.

mDES-based Biorefinery is depicted in FIG. 14 where the oligomeric and polymeric water insoluble lignin component along with mDES is carried over to the lignin fragmentation chamber after biomass pretreatment and saccharification. The generation of water insoluble mDES could be beneficial.

EXAMPLE 2

Figure 15:
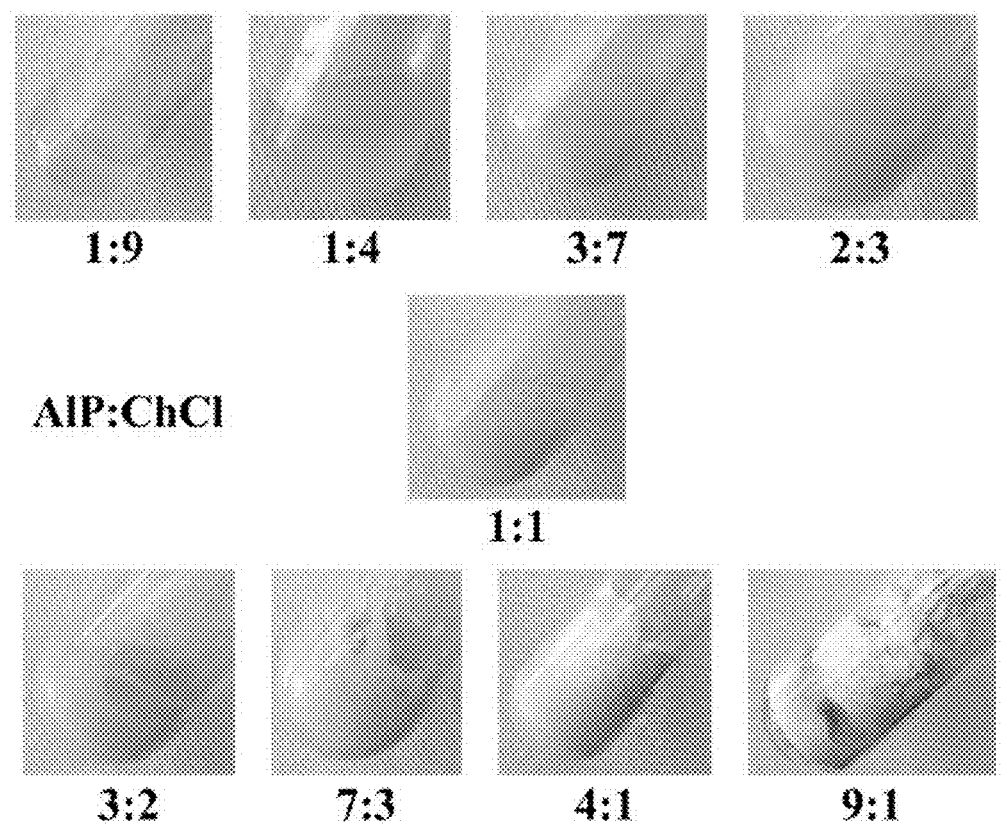
FIG. 15. Visuals of aluminum phosphate with choline chloride in various molar ratios.

Metal phosphates with the advantages of abundance, environmental friendliness and low cost along with the insolubility in water are attractive in this aspect. Considering the case of aluminum phosphate, metal phosphate DESs synthesis were attempted in combination with choline chloride in various ratios. As shown in FIG. 15, higher ratio of choline chloride formed a liquid mixture with AlP after stirring it at 120° C. overnight. This is to be noted that both AlP and ChCl melts at temperatures above 300 C. A molar ratio of 1:4 AlP:ChCl was found to be form the eutectic mixture.

EXAMPLE 3

Figure 16:
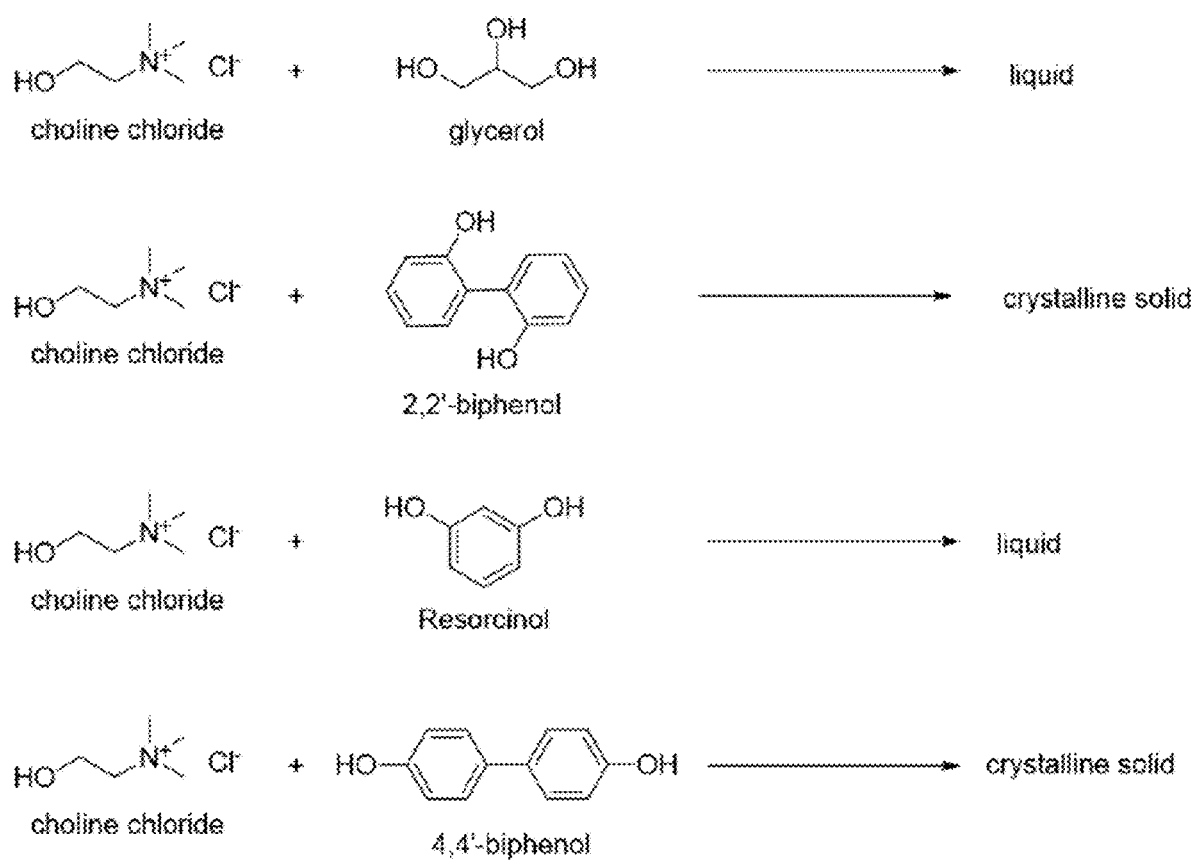
FIG. 16. Choline chloride based DESs for synthesis of mDESs.

The metal phosphate DESs' synthesis was extended beyond two-component to three-component including choline chloride, polyol/phenol system such as glycerol, resorcinol, 2,2'-biphenol, or 4,4'-biphenol in combination with metal phosphates such as aluminum and zinc phosphate. This has been enlisted in Table 2 and FIG. 16.

TABLE 2

Three component mDES synthesis.

| Metal Phosphate | Choline Chloride | Glycerol | |
|---|---|---|---|
| AlP | 2 eq | 2 eq | |
| 1 eq | 2 eq | 4 eq | Opaque colloidal |
|  | 4 eq | 2 eq |  |
|  | 4 eq | 4 eq |  |
|  | 4 eq | 8 eq |  |
| ZnP | 4 eq | 8 eq | Partial ppt observed |
| 1 eq |  |  |  |
| — | 1 eq | 2 eq | clear | heated at 120 C. overnight

AlP was found to form stable mDES compared to zinc phosphate at the attempted ratios of various hydrogen bond donor and acceptor ratios.

Figure 17:
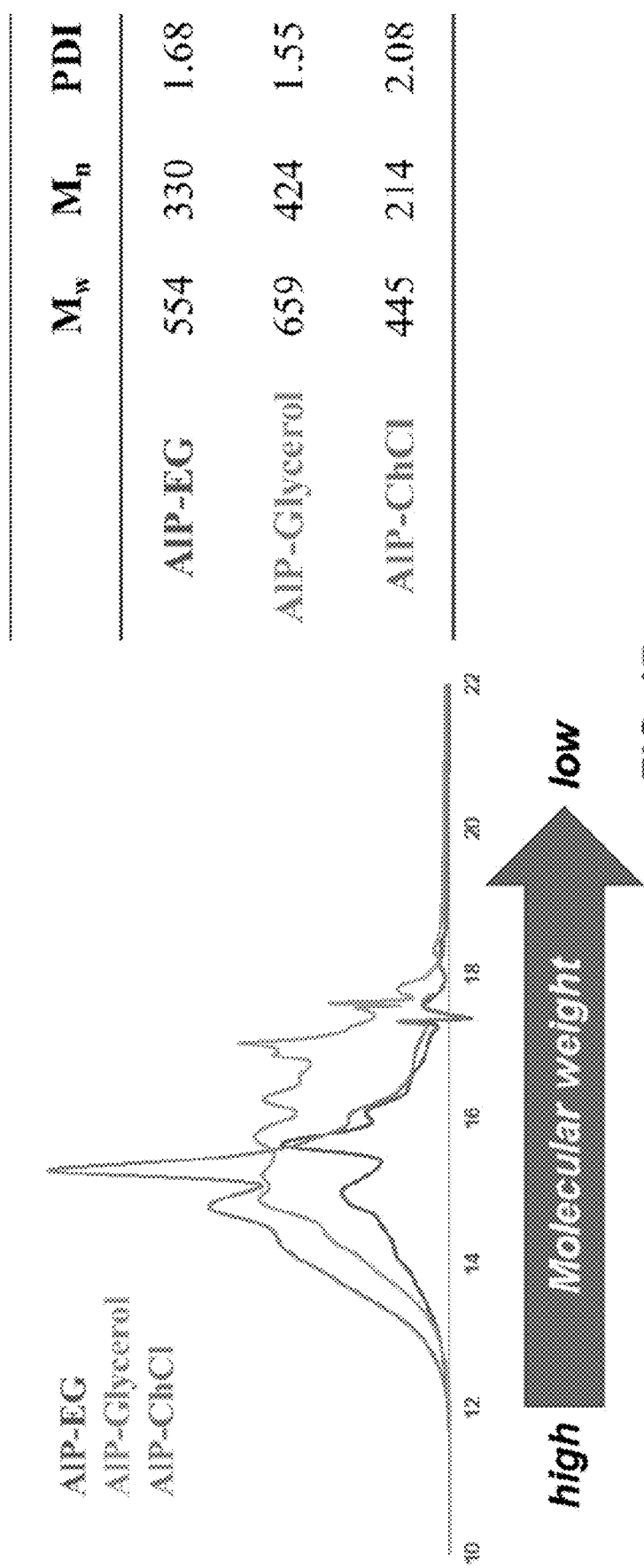
FIG. 17. Gel permeation chromatography (GPC) of ethanol wash after pretreatment.

Pretreatment of 10-50% (w/w) slurry is prepared by mixing 1-5 g of biomass with 9-5 g of mDES in a 25 mL glass tube reactor. Followed by heating the tube reactors in an oil bath at 100-160±2° C. Post pretreatment, 25 mL of ethanol (or water) are added to the slurry before being transferred to 50 ml Falcon tubes and centrifuged at 4500 rpm to separate solids form liquid. The first wash is collected and analyzed to note the changes in the biomass. Recovered solid is further washed with a mixture of ethanol and water (1:1) to remove residual mDES and freeze-dried for further analysis.

mDES formed using AlP—ChCl was most effective in generating lignin with lower molecular weight compared to AlP-glycerol (AlP-Gly) and AlP-ethylene glycol (AlP-EG) as shown in the FIG. 17.

Figure 18:
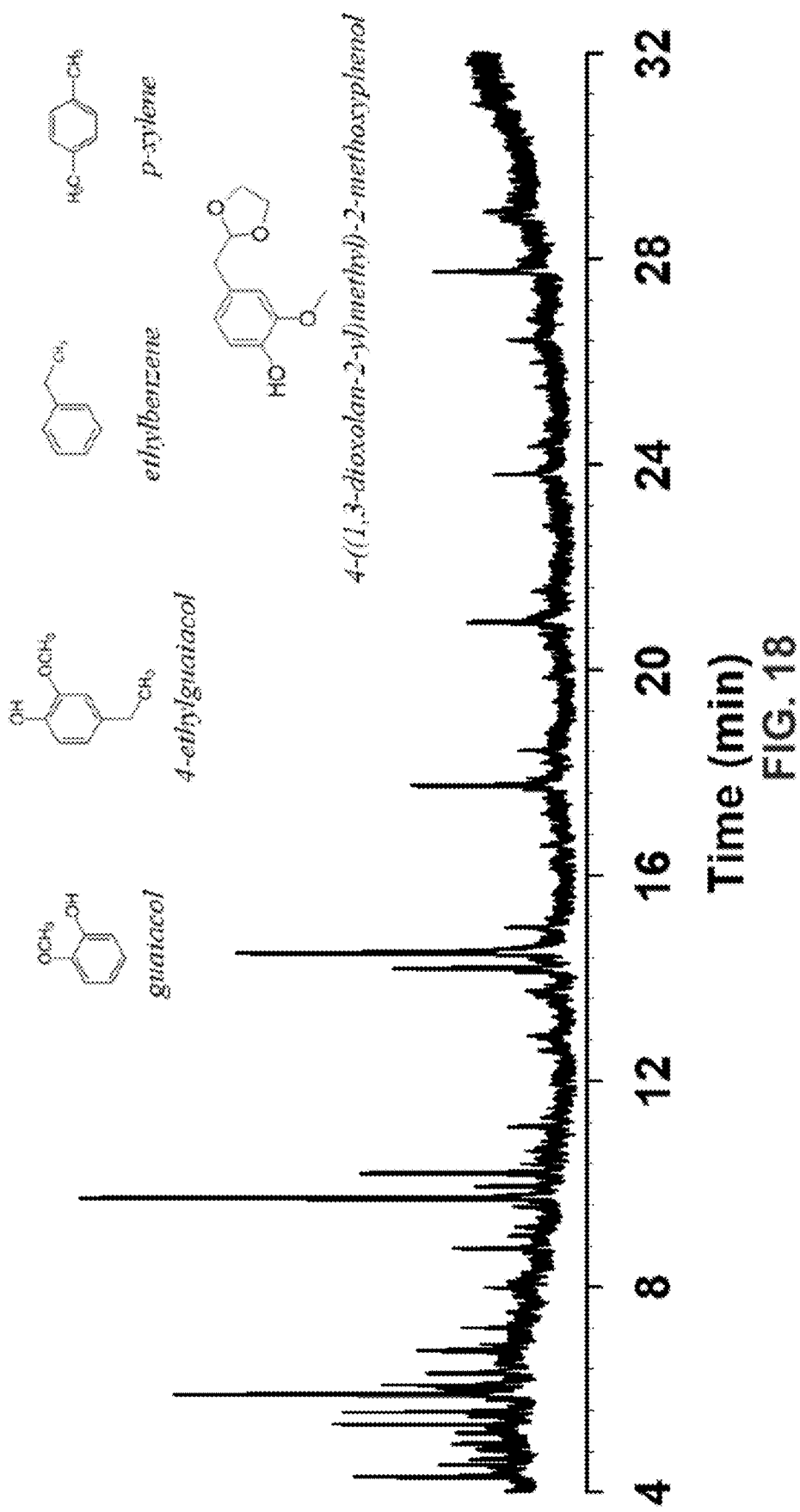
FIG. 18. GC-MS of ethanol layer after pretreatment using AlP—ChCl mDES.

Ethanol layer after pretreatment of biomass was subjected to GC-MS to reveal the depolymerization of the lignin to afford phenols such as guaiacol, 4-ethylguaiacol, 4-((1,3-dioxolan-2-yl)methyl)-2-methoxyphenol and hydrocarbons, such as ethylbenzene and xylenes as major products as shown in FIG. 18.

Table 3 summarizes pretreatment experiments with various 3-component mDESs and the use of water or ethanol as the washing solvent.

TABLE 3

Summary involving three-component DESs/mDESs.

| DES and loading | Additives and loading | Washing solver |
|---|---|---|
| ChCl-Glycerol (80 wt %) | — | Water |
| ChCl-Glycerol (79 wt %) | AlP (1 wt %) | Water |
| ChCl-Glycerol (80 wt %) | — | Ethanol |
| ChCl-Glycerol (79 wt %) | AlP (1 wt %) | Ethanol |
| ChCl-Resorcinol (80 wt %) | — | Water |
| ChCl-Resorcinol (79 wt %) | AlP (1 wt %) | Water |
| ChCl-Resorcinol (80 wt %) | — | Ethanol |
| ChCl-Resorcinol (79 wt %) | AlP (1 wt %) | Ethanol |
| ChCl-2,2'-biphenol (80 wt %) | — | Water |
| ChCl-2,2'-biphenol (79 wt %) | AlP (1 wt %) | Water |
| ChCl-2,2'-biphenol (80 wt %) | — | Ethanol |
| ChCl-2,2'-biphenol (79 wt %) | AlP (1 wt %) | Ethanol |
| ChCl-4,4'-biphenol (80 wt %) | — | Water |
| ChCl-4,4'-biphenol (79 wt %) | AlP (1 wt %) | Water |
| ChCl-4,4'-biphenol (80 wt %) | — | Ethanol |
| ChCl-4,4'-biphenol (79 wt %) | AlP (1 wt %) | Ethanol |

Figure 19:
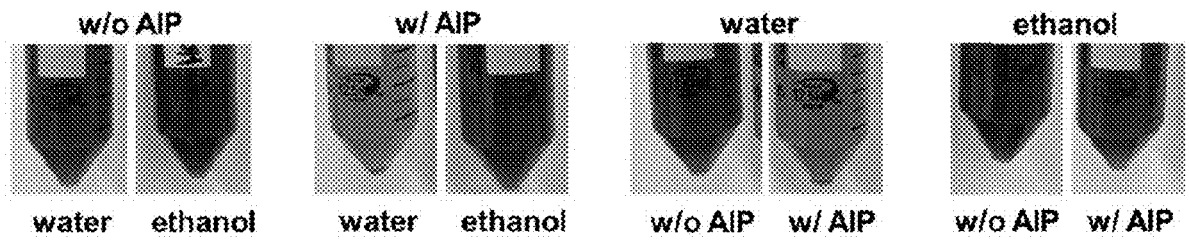
FIG. 19. Aqueous or ethanol wash layer pretreatment with ChCl-resorcinol DES/mDES system. Washed layers after pretreatment with ChCl-resorcinol DES system.
Figure 20:
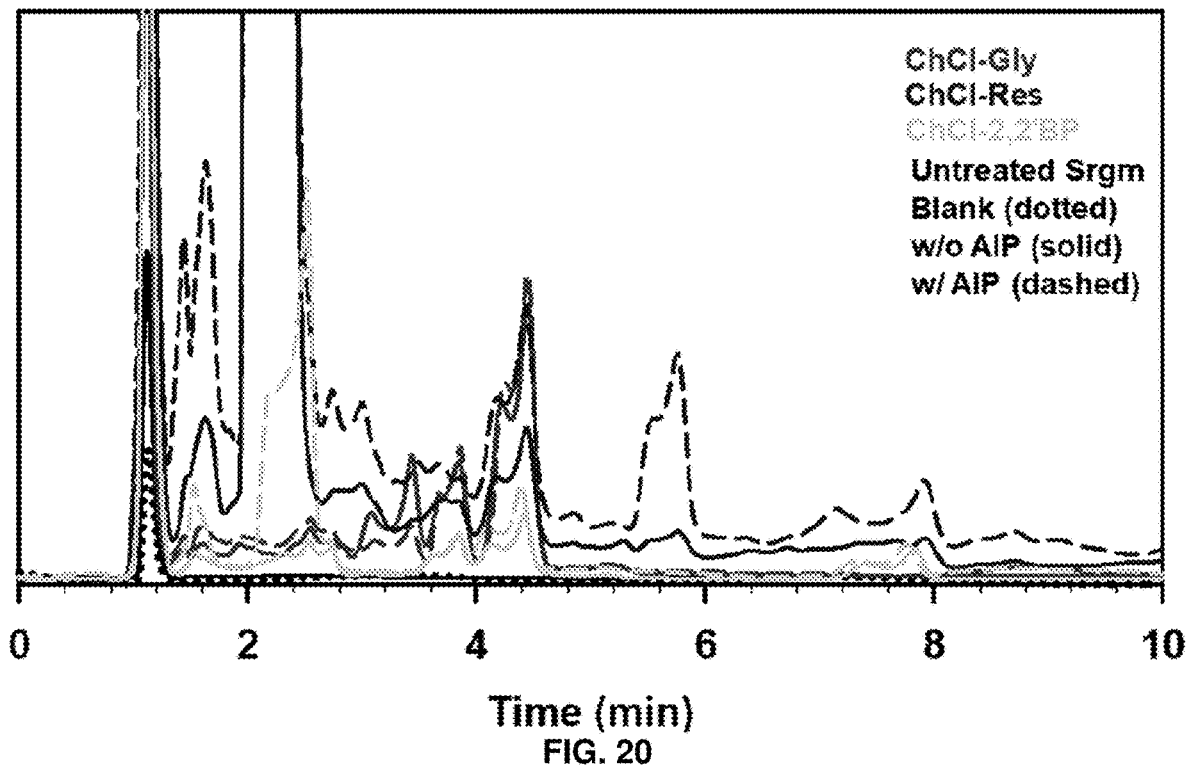
FIG. 20. HPLC chromatogram of ethanol wash layers obtained after pretreating biomass with three-component DESs/mDESs.

FIGS. 19 and 20 illustrates the impact of the solvent chosen to wash along with the metal phosphate such as aluminum phosphate for the ChCl-resorcinol based DES system. Based on the HPLC profile, ChCl-Res system with and without AlP afforded more signals. Blank and untreated sorghum on the other hand had no signals the than solvent peak.

Most effective was the ChCl-resorcinol system (solid blue) where the activity is further enhanced in the presence of metal phosphate such as AlP (dashed blue) to yield aromatic acids and/or phenolic compounds.

FIGS. 21 through 25 summarize the sugar release efficacy from the biomass after pretreatment with these mDESs.

Figure 21:
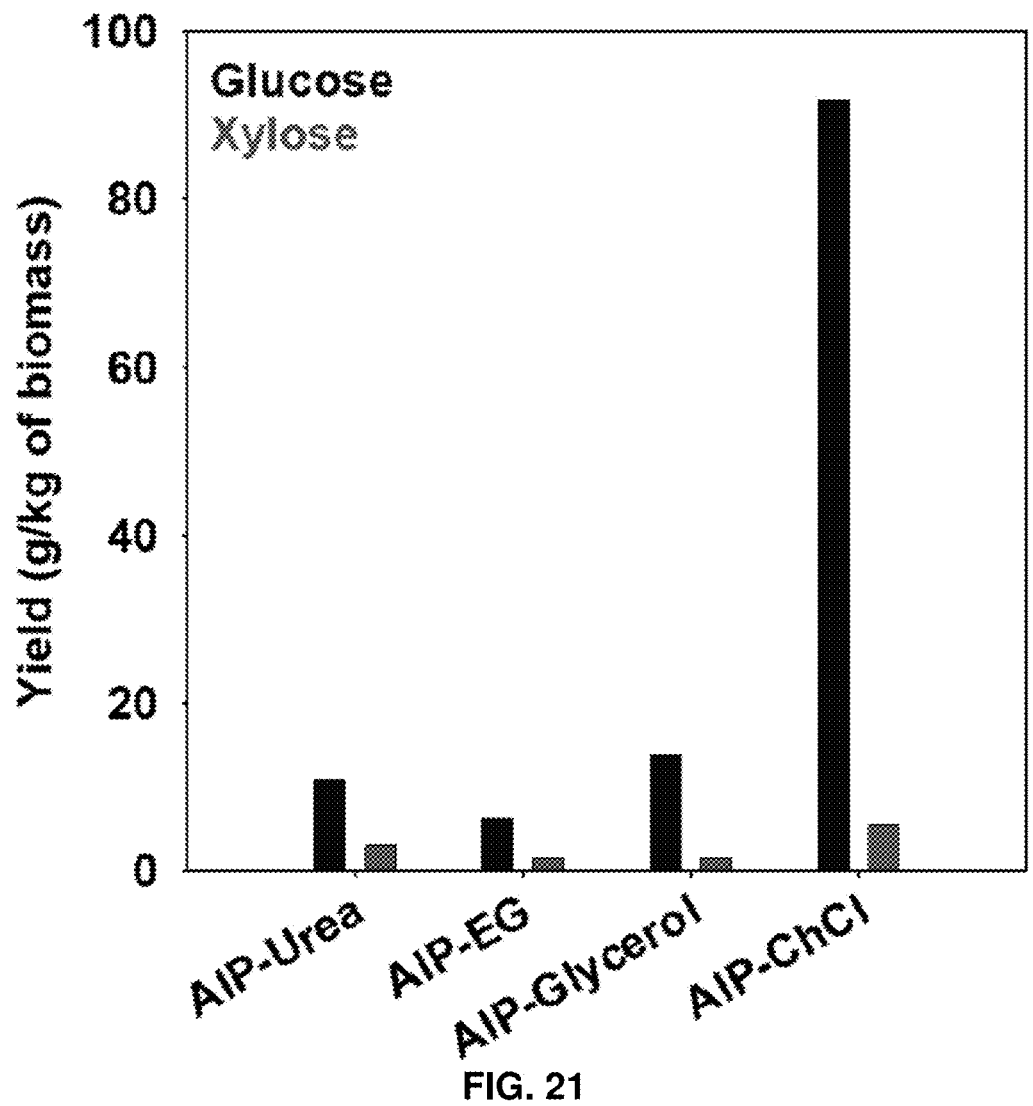
FIG. 21. Sugar release using AlP-based mDESs. Pretreatment conditions: 50 wt % biomass; 50 wt % DES; 140° C.; 5 hr; washed after pretreatment.

Among the various AlP-based DESs namely, AlP-Gly, AlP-Urea, AlP-EG, and AlP—ChCl, AlP—ChCl had the highest sugar release at 50 wt % biomass loading at 140° C. as shown in FIG. 21.

Figure 22:
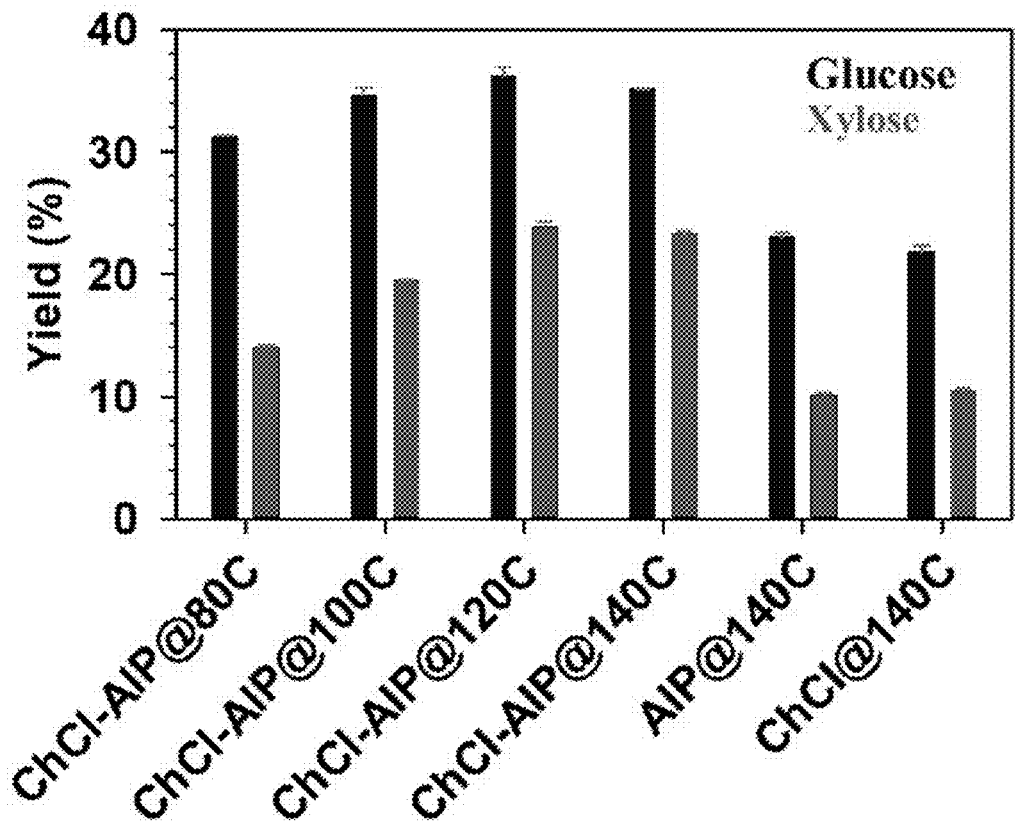
FIG. 22. Screening with AlP—ChCl mDES: effect of temperature. Pretreatment conditions: 50 wt % biomass; 1 hr. Saccharification: 10 mg protein/g biomass; 50° C.; 72 hr.
Figure 23:
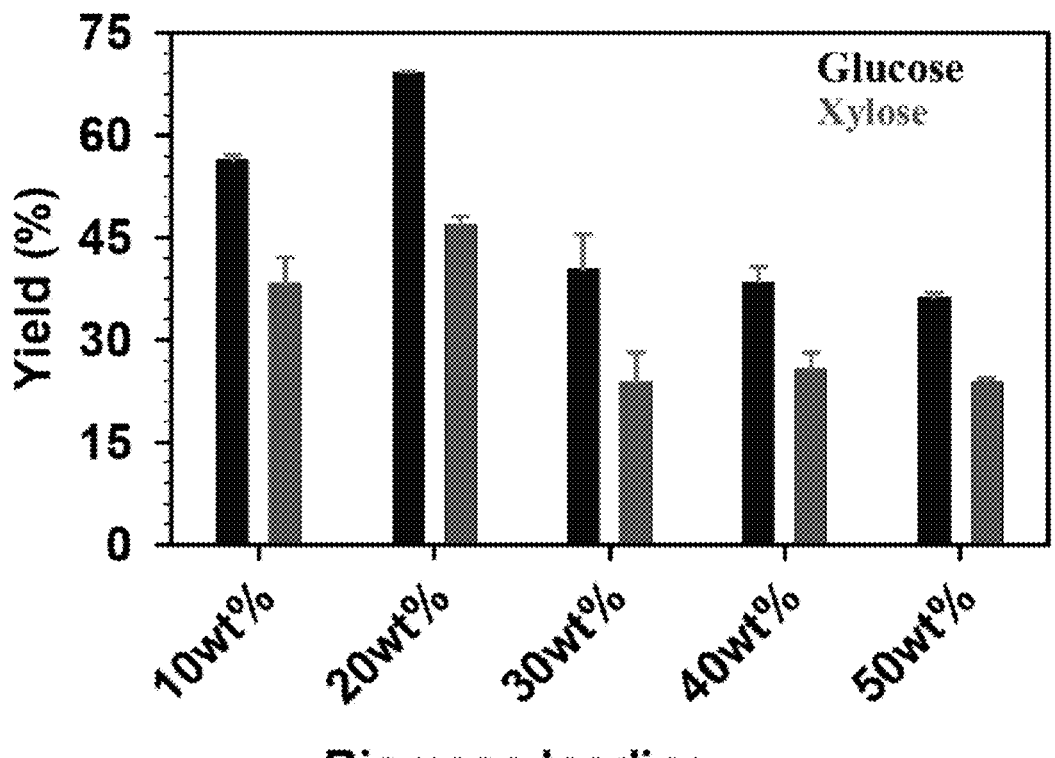
FIG. 23. Screening with AlP—ChCl mDES: effect of biomass loading. Pretreatment conditions: AlP—ChCl DES; 120° C.; 1 hr. Saccharification: 10 mg protein/g biomass; 50° C.; 72 hr.

Higher sugar release up to 73% glucose and 46% xylose were achieved by reducing the severity of the reaction process that is by pretreating 20 wt % biomass at 120° C. for an hour as shown in FIGS. 22 and 23.

Figure 24:
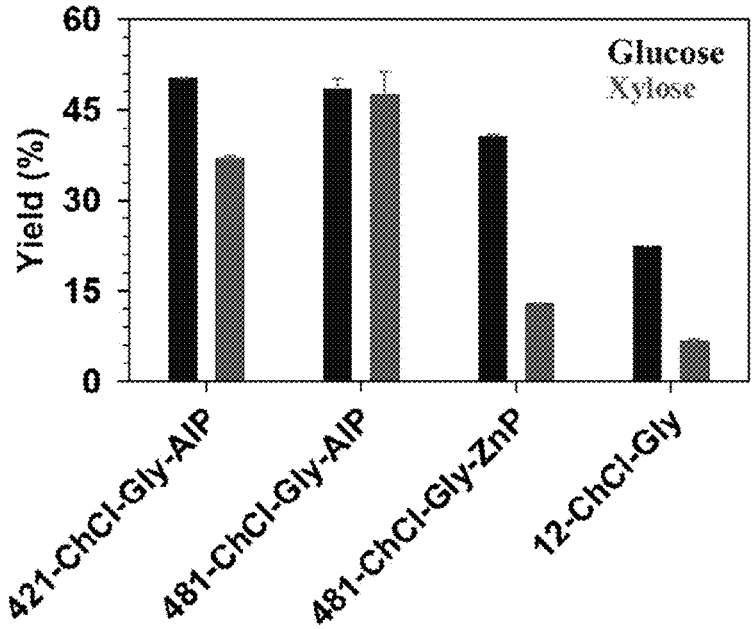
FIG. 24. Sugar release using three-component mDESs. Pretreatment conditions: 20 wt % biomass; 120° C.; 1 hr. Saccharification: 10 mg protein/g biomass; 50° C.; 72 hr.

A third component such as glycerol in the AlP—ChCl DES system was also found to be effective in releasing at least half of the sugars from the biomass under unoptimized conditions. Higher ratio of glycerol in the system improved the xylose release as shown in FIG. 24.

Figure 25:
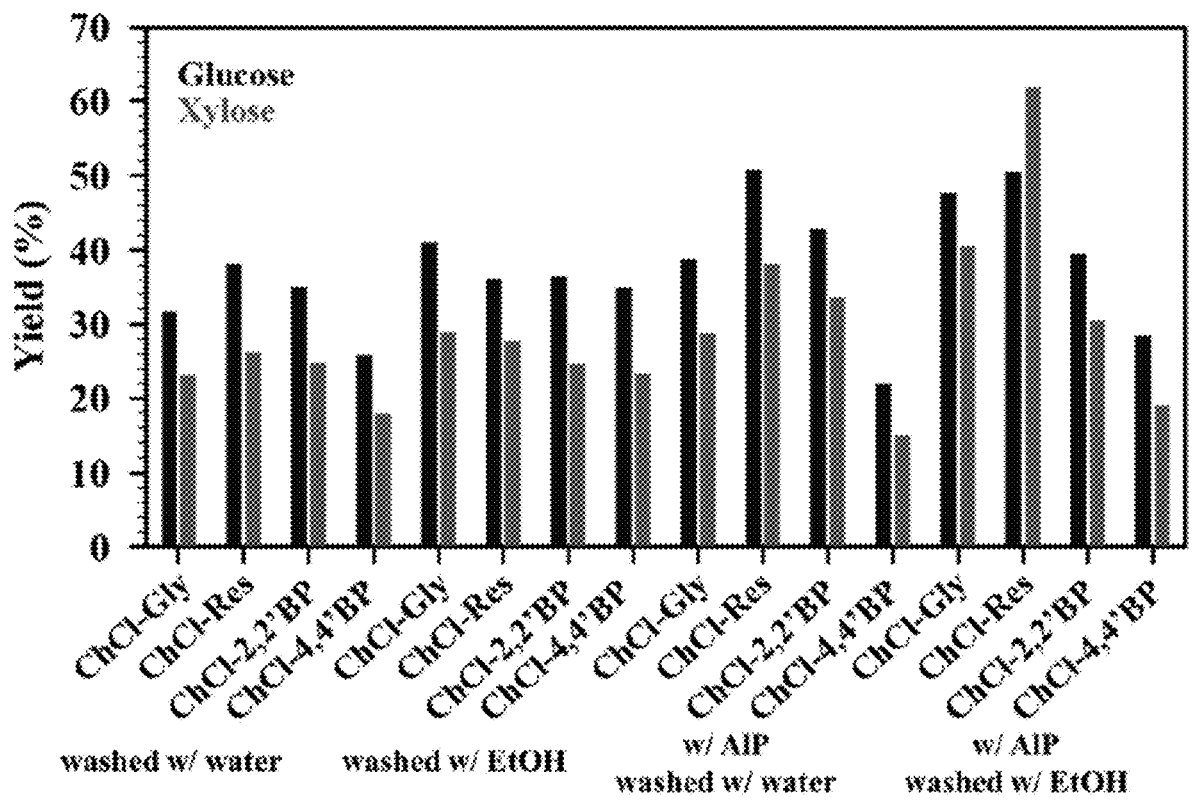
FIG. 25. Effect of washing and content of AlP. Pretreatment conditions: INL sorghum (20 wt %); DES (79-80 wt %); AlP (0-1 wt %); 140° C.; 3 hr. Washed after pretreatment. Saccharification: 5 wt % biomass loading; 10 mg protein/g biomass; 50° C.; 72 hr.

Among various third component namely, glycerol, resorcinol, 2,2'-biphenol, and 4,4'-biphenol, resorcinol in combination with ChCl and AlP afforded highest glucose and xylose yields as in FIG. 25. It was also seen that washing solvent had a crucial impact on the amount of sugar released after enzymatic hydrolysis. It is probably due to the loss of sugars during water washing after pretreatment step.

Figure 26:
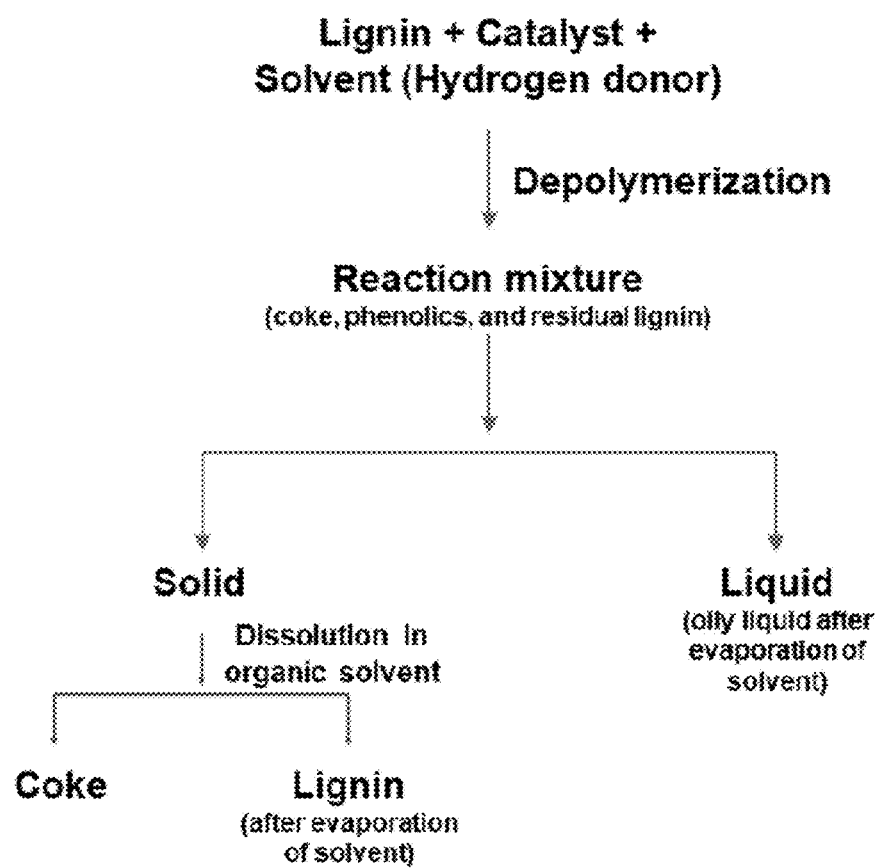
FIG. 26. Experimental flow chart.

The HPLC profile of the wash layer after biomass pretreatment (FIG. 20) indicated the lignin depolymerization under pretreatment conditions. To verify the lignin depolymerization experiments over mDESs with commercial lignin sources such as organosolv lignin were designed as the starting point. Experimental flow is shown in FIG. 26.

Both AlP and zirconium phosphate (ZrP) were employed along with ChCl and Glycerol as second and third component of the mDESs. Control experiments with only AlP, ZrP, ChCl-Gly were also performed. Table 4 summarizes the conversion efficiency of these various catalysts and compares with the commercial Pd/C catalyst. ZrP-based mDES had the highest conversion efficiency with only 18% of the solids recovered. On the other hand, 49% and about 47.6% solids were recovered with AlP-based DES and Pd/C catalysts, respectively.

TABLE 4

Conversion efficiency of various mDESs.

| DES/Catalyst | % Solid Recovered |
|---|---|
| ChCl-Gly | 63.73 |
| AlP | 49.03 |
| ChCl-Gly-AlP | 42.11 |
| ZrP | 54.23 |
| ChCl-Gly-ZrP | 18.83 |
| Pd/C | 47.59 |

Organosolv Lignin, Catalyst (5 wt % based on lignin), Ethanol: Toluene (1:4), 220 C., 5h, $N_2$ (20 bar).

The oil obtained from the lignin depolymerization after evaporation of reaction solvent was analyzed using NMR, GPC, and LC/LC-MS.

Figure 27:
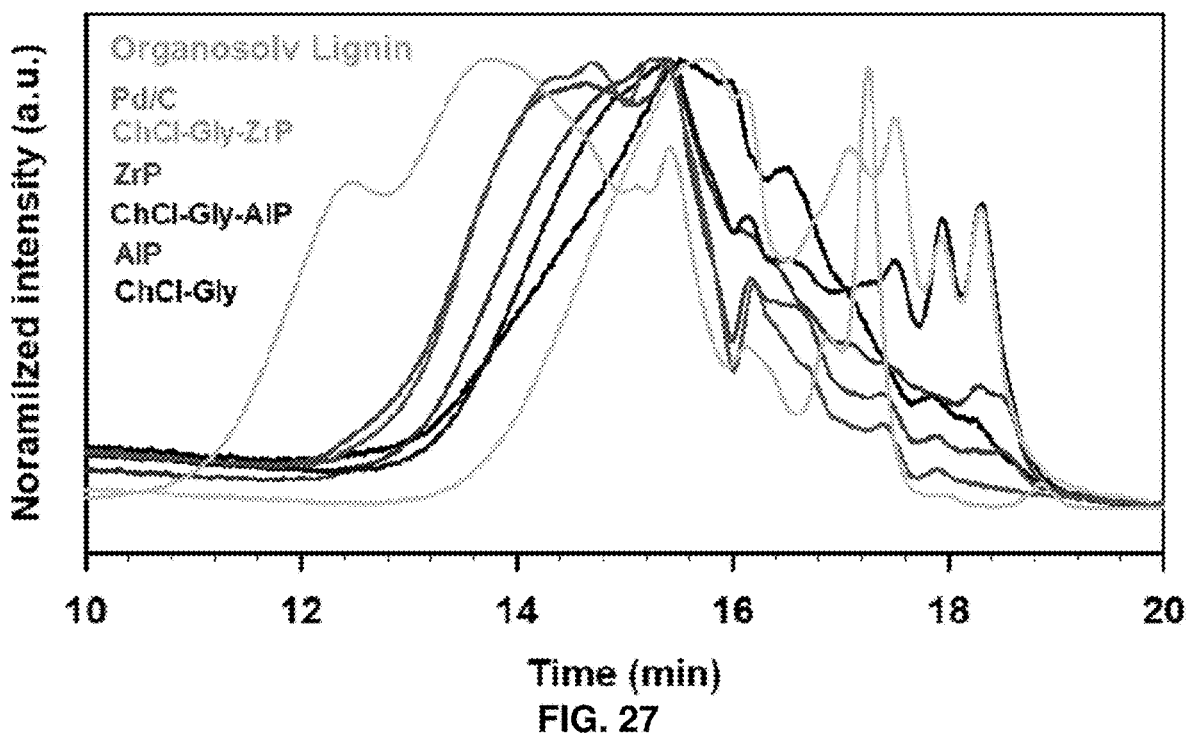
FIG. 27. GPC of oil obtained after lignin depolymerization.

In strong agreement to the yields/conversion values, ZrP-DES was most effective in producing lower MW fractions with a Mw of 306 Da. Organosolv lignin, starting material, has a Mw of about 10K Da. AlP-DES also afforded the oil with Mw of 424 Da. Only ZrP and Pd/C had a similar effect on the depolymerization of organosolv lignin. Molecular weight distribution of these oil is plotted as FIG. 27 and is summarized in Table 5.

TABLE 5

Molecular weight distribution.

| | Mn | Mw | PDI |
|---|---|---|---|
| OrgnSlv Lgnn | 331 | 10244 | 30.993 |
| ChCl-Gly | 128 | 793 | 6.179 |
| AlP | 145 | 539 | 3.729 |
| ChCl-Gly-AlP | 145 | 424 | 2.916 |
| ZrP | 162 | 678 | 4.186 |
| ChCl-Gly-ZrP | 43 | 306 | 7.035 |
| Pd/C | 204 | 698 | 3.415 |

Figure 28:
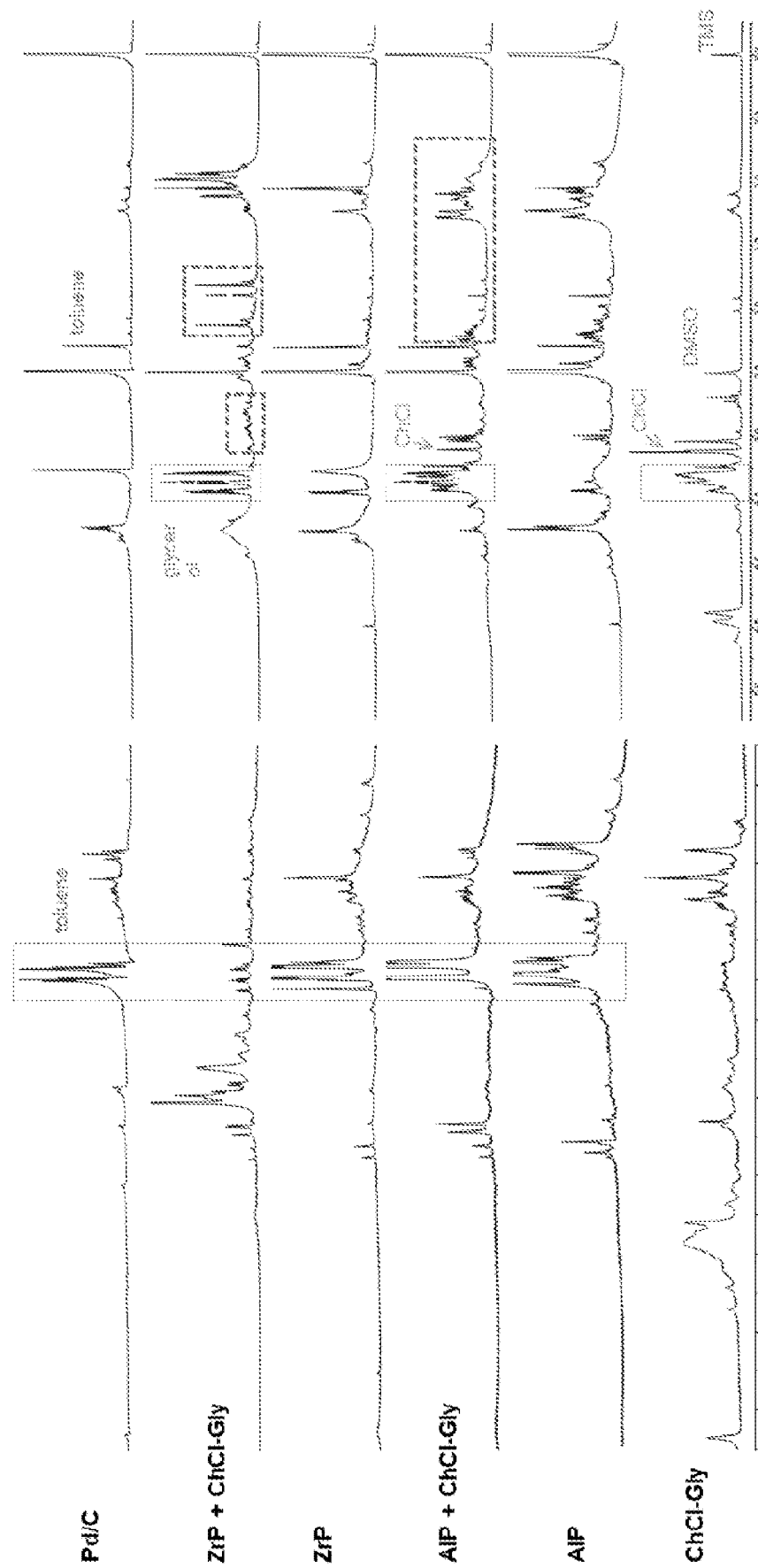
FIG. 28. 1H NMR of oil obtained after lignin depolymerization.

1H NMR of the oil recorded in DMSO-d6 as the lock solvent supplemented with TMS as an internal standard is shown in FIG. 28. Peaks corresponding to the aliphatic carbons appear in metal phosphates and DES system. Less signals were observed in the C—O region indicating cleavage of ether bonds of lignin units. Also, peaks corresponding to the olefinic region dominates along with signals in the aromatic region. The protons on the carbon attached to either olefins or aromatic ring explains the origin of peaks around 2 ppm in the aliphatic region. The peaks within the region of 6.5-7 ppm indicates the presence of methoxy groups attached to the ring.

Figure 29:
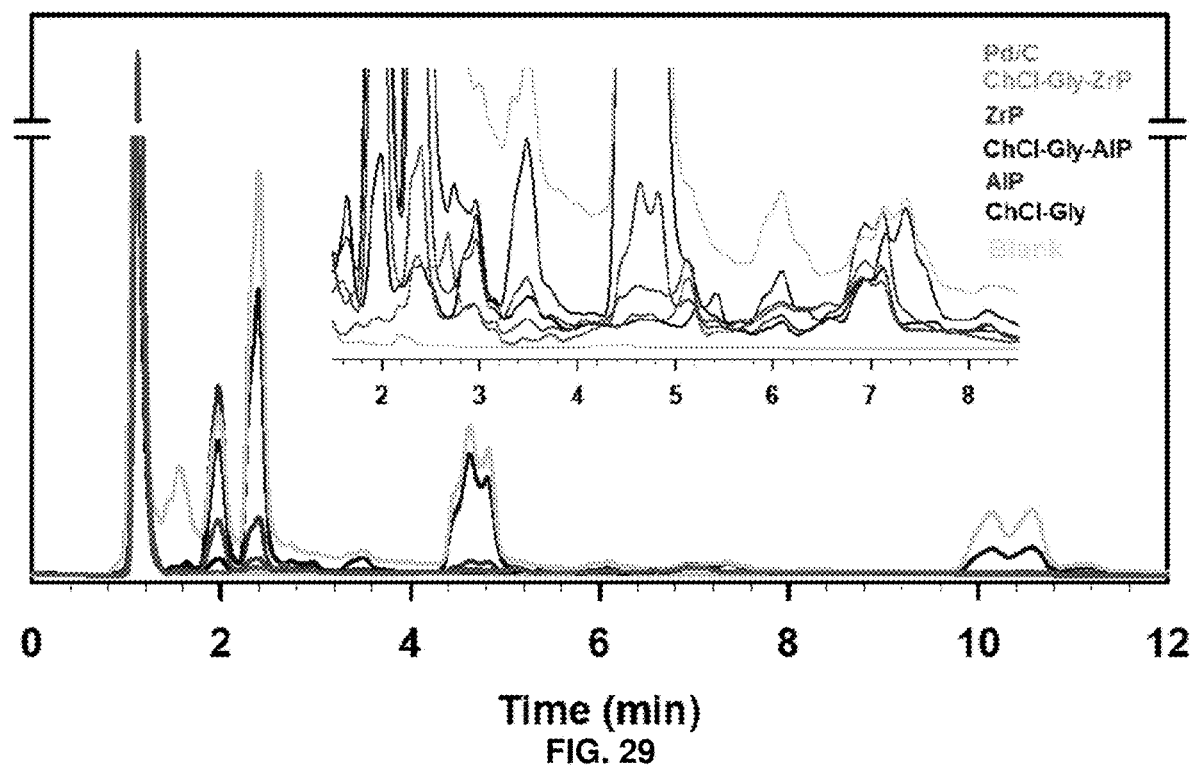
FIG. 29. HPLC chromatogram of oil obtained after lignin depolymerization.
Figure 30:
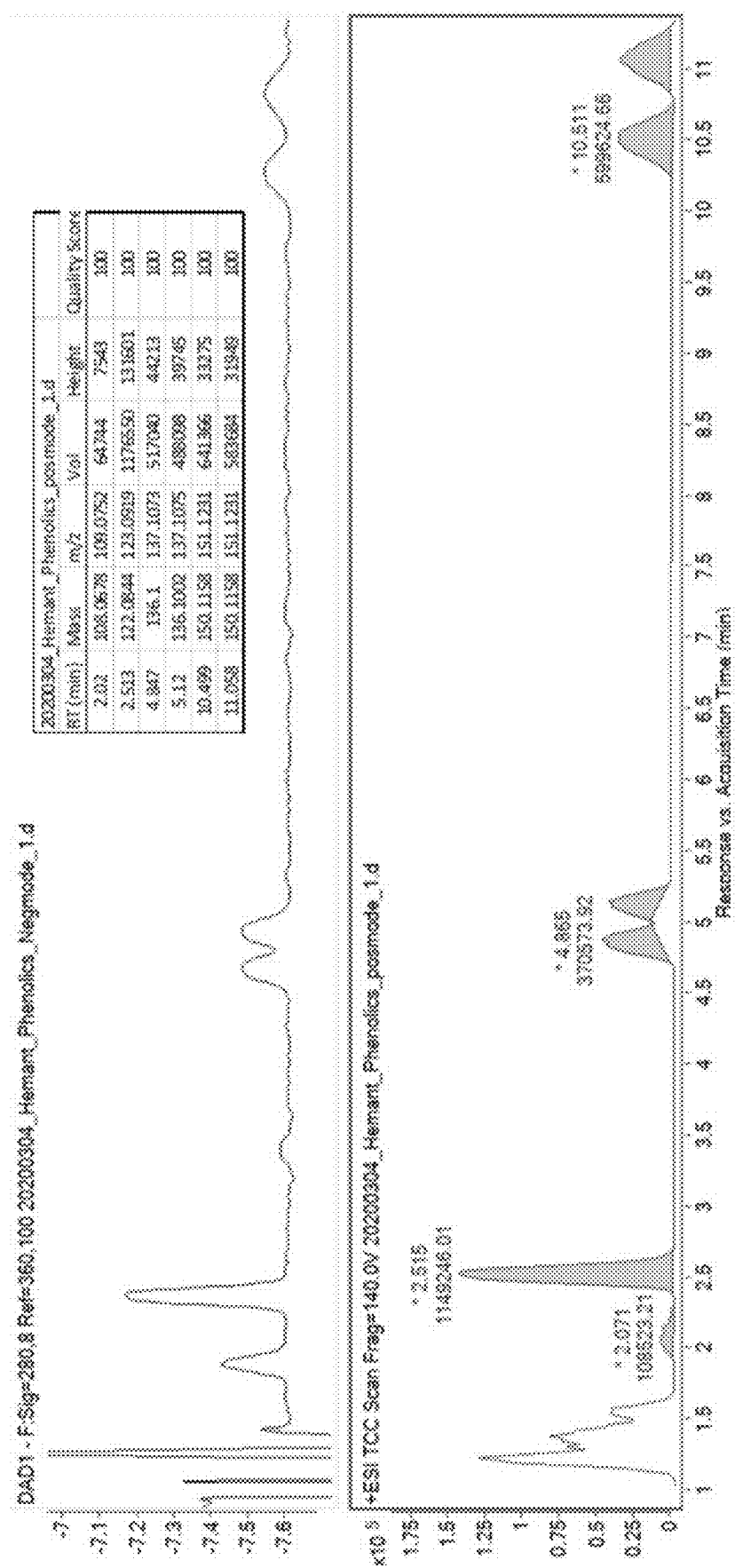
FIG. 30. LC-MS analysis of oil obtained after lignin depolymerization.

Peaks corresponding to monomer, dimer and trimer units were observed in the HPLC profile with metal phosphate DESs after lignin depolymerization as shown in FIGS. 29 and 30. At 280 nm and positive mode at least 6 unique peaks were observed with 4 base peaks.

Figure 31:
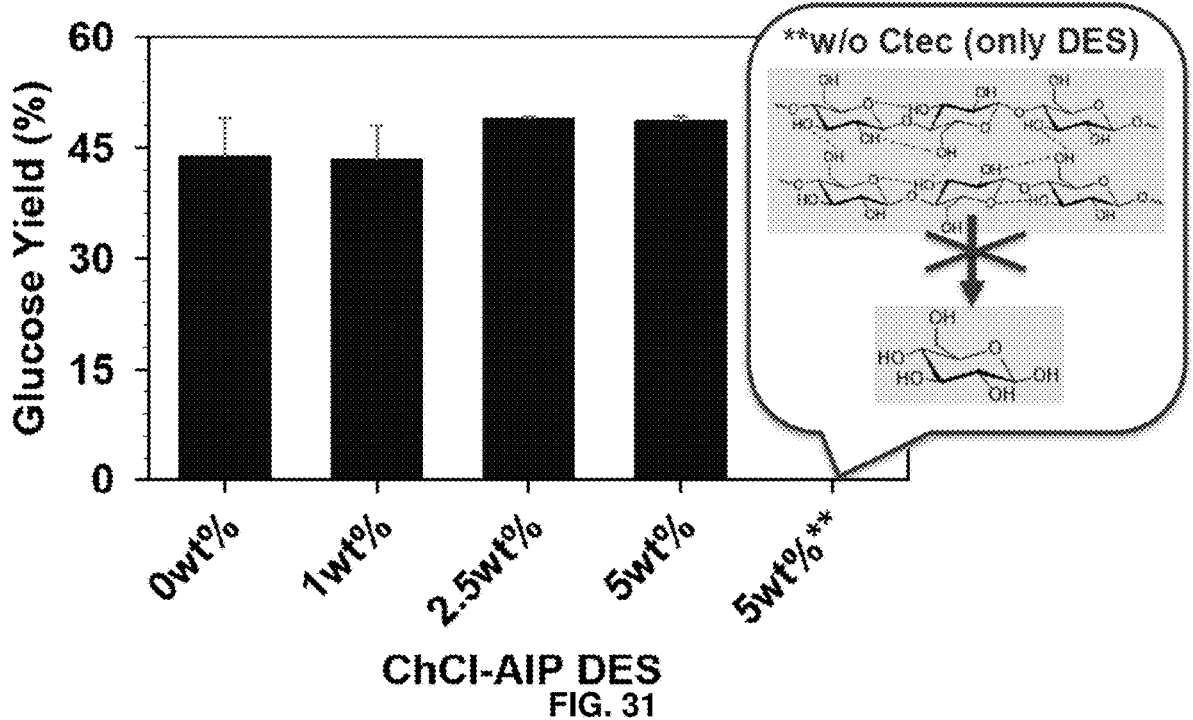
FIG. 31. Screening with AlP—ChCl DES: Enzyme inhibition. Microcrystalline cellulose, ALP-ChCl DES; CTec3; 50° C.; 24 hr.

FIG. 31 establishes that metal phosphate DESs are non-inhibitory to enzymes at least up to 5 wt %. Control experiment with no enzyme also confirmed that AlP-DES does not hydrolyze microcrystalline cellulose at 50° C.

Figure 32:
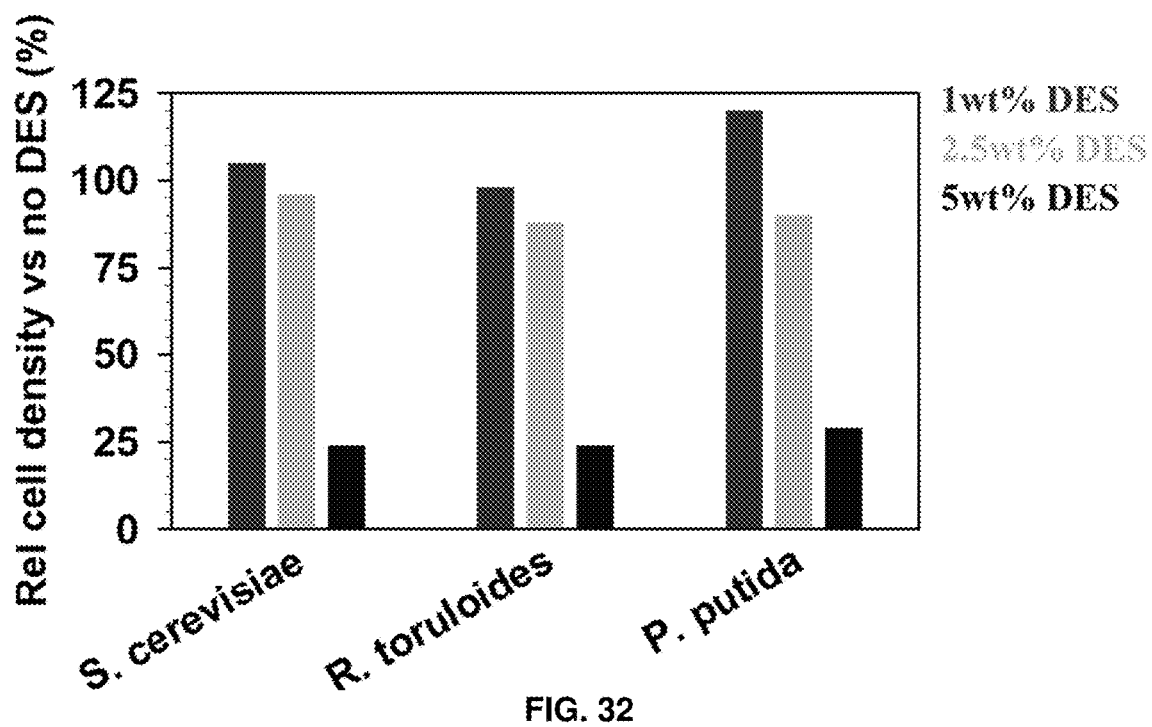
FIG. 32. Screening with AlP—ChCl DES: Microbial toxicity.

Also, metal phosphate DESs were found to be non-toxic to microbes namely, S. cerevisiae, R. toruloides, and P. putida at least up to a concentration of 2.5 wt % as shown in FIG. 32. This was attributed to the limited aqueous solubility of metal phosphate DESs.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method to produce a biofuel or chemical compound from a biomass, the method comprising: (a) introducing a biomass and a metal-based deep eutectic solvent (mDES), or mixture thereof, into a vessel to form a composition, wherein the biomass forms 20% to 50% solid loading of the composition and the mDES, or mixture thereof, solubilizes the biomass; and, (b) introducing a cellulase to the composition to release a sugar from the solubilized biomass; wherein the introducing step (b) produces a sugar yield of about 90% or more.

2. The method of claim 1, wherein the mDES further comprises: (a) a metal halide; and, (b) a polyol or amine.

3. The method of claim 2, wherein the metal halide is a metal chloride.

4. The method of claim 3, wherein the metal halide is a transition metal chloride.

5. The method of claim 4, wherein the transition metal chloride is $ZnCl_2$, $CuCl_2$, $FeCl_3$, $CoCl_2$, $NbCl_5$, $AlCl_3$, $NiCl_2$, or $CrCl_3$.

6. The method of claim 2, wherein the polyol is a glycol.

7. The method of claim 6, wherein the glycol is ethylene glycol.

8. The method of claim 2, wherein the amine is 1,2-diaminopropane, 1,3-diaminopropane, diethylenetriamine, putrescine, cadaverine, ethylenediamine, 2-methylethanolamine, 1-amino-2-propanol, bis(3-aminopropyl)amine, morpholine, or ethanolamine.

9. The method of claim 2, wherein the mDES comprises a 1:4 molar ratio of $ZnCl_2$:ethylene glycol.

10. The method of claim 2, wherein the mDES comprises a 1:4 molar ratio of $ZnCl_2$:glycerol.

11. The method of claim 2, wherein the mDES comprises a $ZnCl_2$ molar concentration having a range from 2.44% to 20%.

12. The method of claim 2, wherein the biomass and mDES composition of step (a) comprises a $ZnCl_2$ molar concentration having a range from 2% to 16%.

13. The method of claim 1, wherein the composition of step (a) has a temperature of from about 100° C. to about 212° C.

14. The method of claim 1, the method further comprising: (c) introducing a microbe to the composition such that the microbe consumes the sugar released from the introducing step (b) to produce a biofuel or chemical compound, and (d) the biofuel or chemical compound is separated from the composition.

15. The method of claim 1, wherein the introducing step (a) results in formation of an aqueous layer comprising the sugar and an mDES layer comprising lignin; and the method further comprises: (c) separating the aqueous layer from the mDES layer.

16. The method of claim 1, wherein the biomass forms 20% to 35% solid loading of the composition.

* * * * *